United States Patent [19]

Rorabaugh et al.

[11] Patent Number: 5,035,500
[45] Date of Patent: Jul. 30, 1991

[54] AUTOMATED OCULAR PERIMETRY, PARTICULARLY KINETIC PERIMETRY

[76] Inventors: Dale A. Rorabaugh, P.O. Box 1864, Rancho Santa Fe, Calif. 92067; Neil Davis, 3092 Hendricks Hill Dr., Eugene, Oreg. 97403; George A. Mansfield, Jr., 5543 Barkla, San Diego, Calif. 92122; Vince Brancaccio, 3092 Hendricks Hill Dr., Eugene, Oreg. 97403

[21] Appl. No.: 503,116

[22] Filed: Mar. 26, 1990

Related U.S. Application Data

[63] Continuation of Ser. No. 231,764, Aug. 12, 1988, abandoned.

[51] Int. Cl.⁵ .............................................. A61B 3/02
[52] U.S. Cl. ................................... 351/226; 351/224
[58] Field of Search ..................... 351/224, 225, 226

[56] References Cited

U.S. PATENT DOCUMENTS 4,260,227  4/1981  Munnerlyn et al. ............... 351/226
4,490,023  12/1984  Ludwig ............................. 351/226

Primary Examiner—Paul M. Dzierzynski
Attorney, Agent, or Firm—William C. Fuess

[57] ABSTRACT

A first light is moved and illuminated by an x-y plotter mechanism on a rear projection screen under computer control so as to be continuously fixated by an eye of a test subject. The computer also causes one or ones of fixed-position second lights, typically sixteen in number positioned in a regular array, to momentarily illuminate at various times corresponding to various positions of the moving first light. The test subject indicates detection or non-detection of the momentary illuminations to the computer by voicing the numbers "1", "2", "3", etc. From successive illuminations and test subject responses the computer is able to survey the entire visual field of each subject's eye in all directions. The surveyed visual field is plotted on graph paper with the same x-y plotter mechanism that is otherwise and at other times used for moving the first light source.

61 Claims, 21 Drawing Sheets

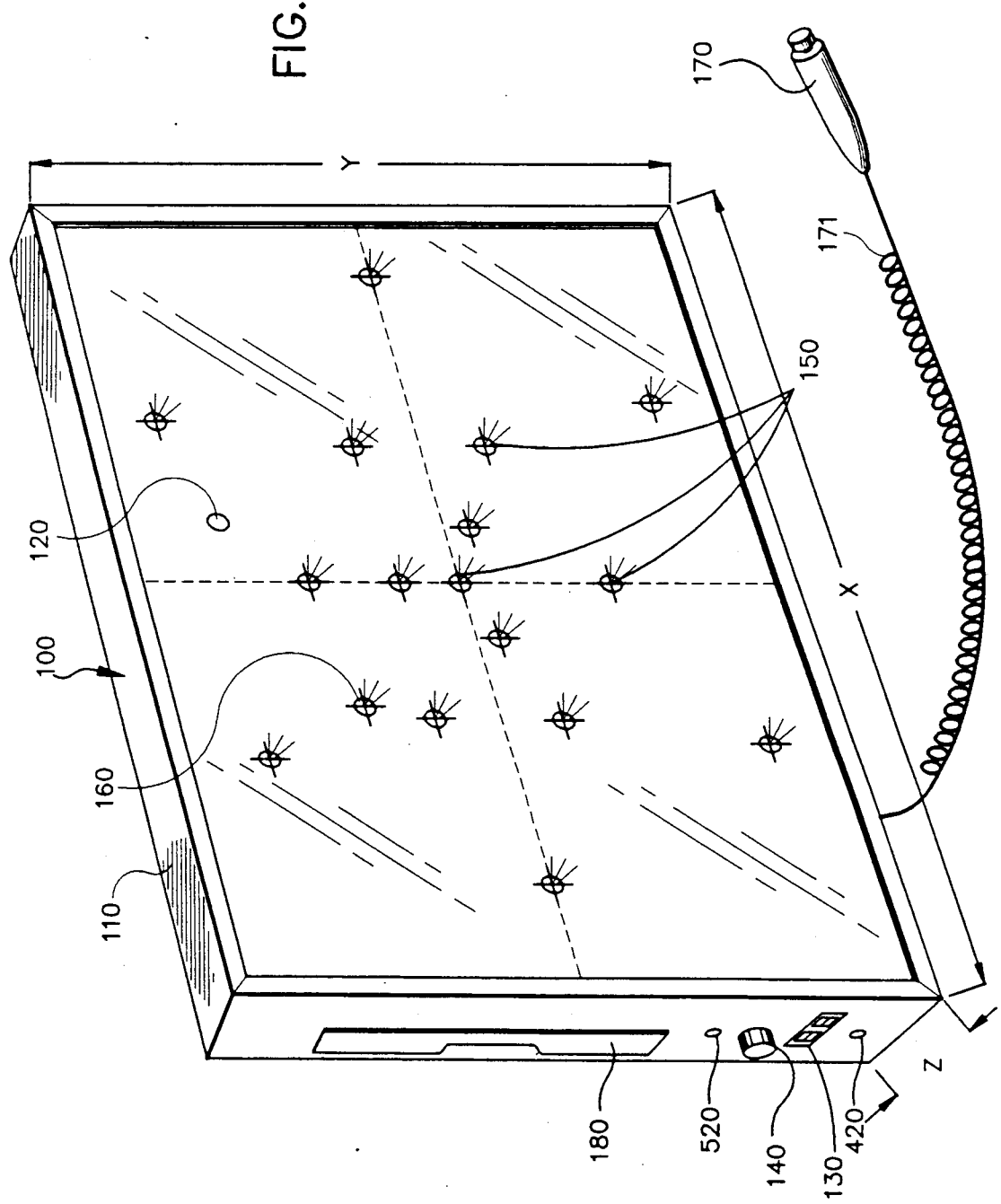

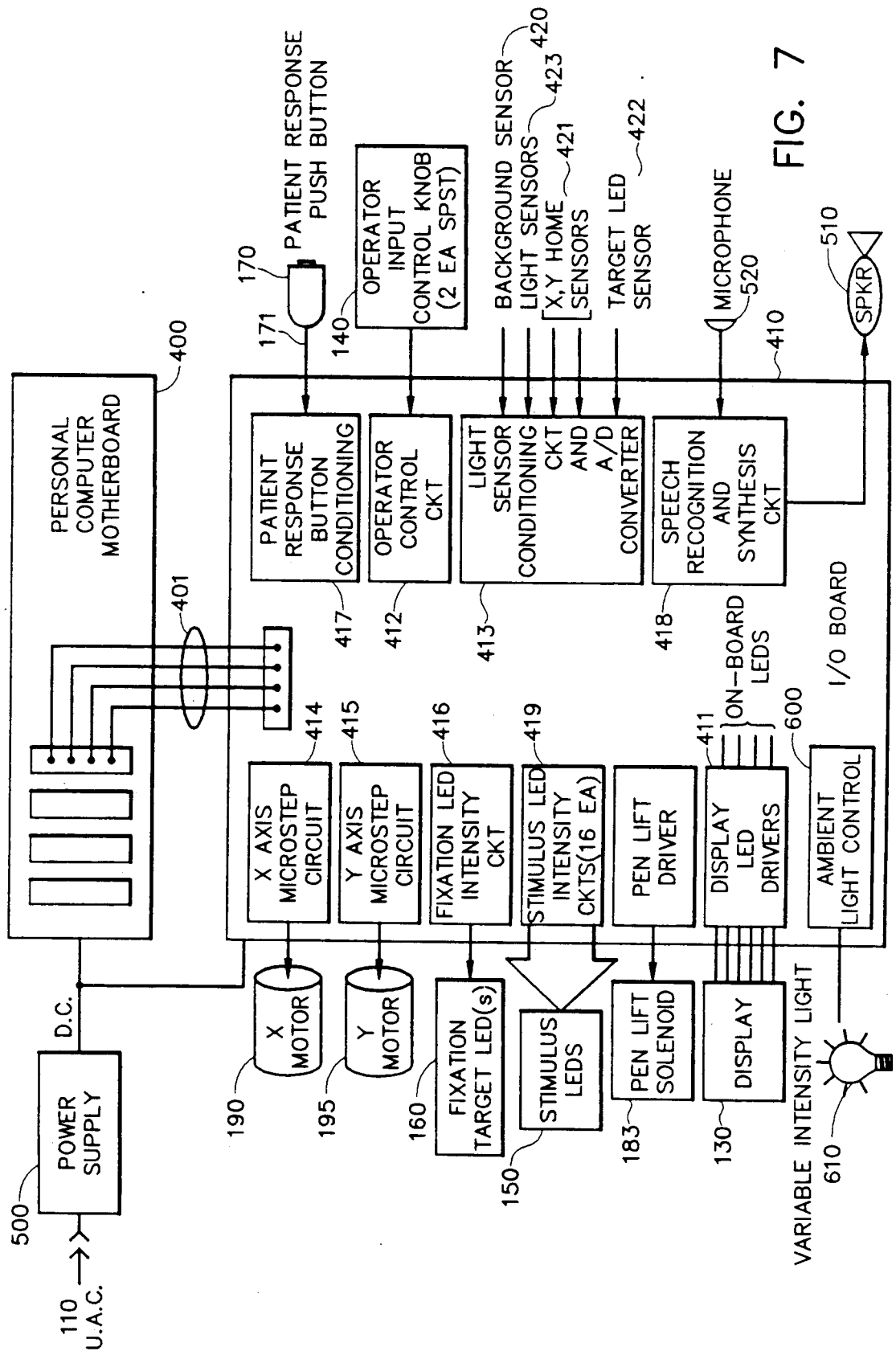

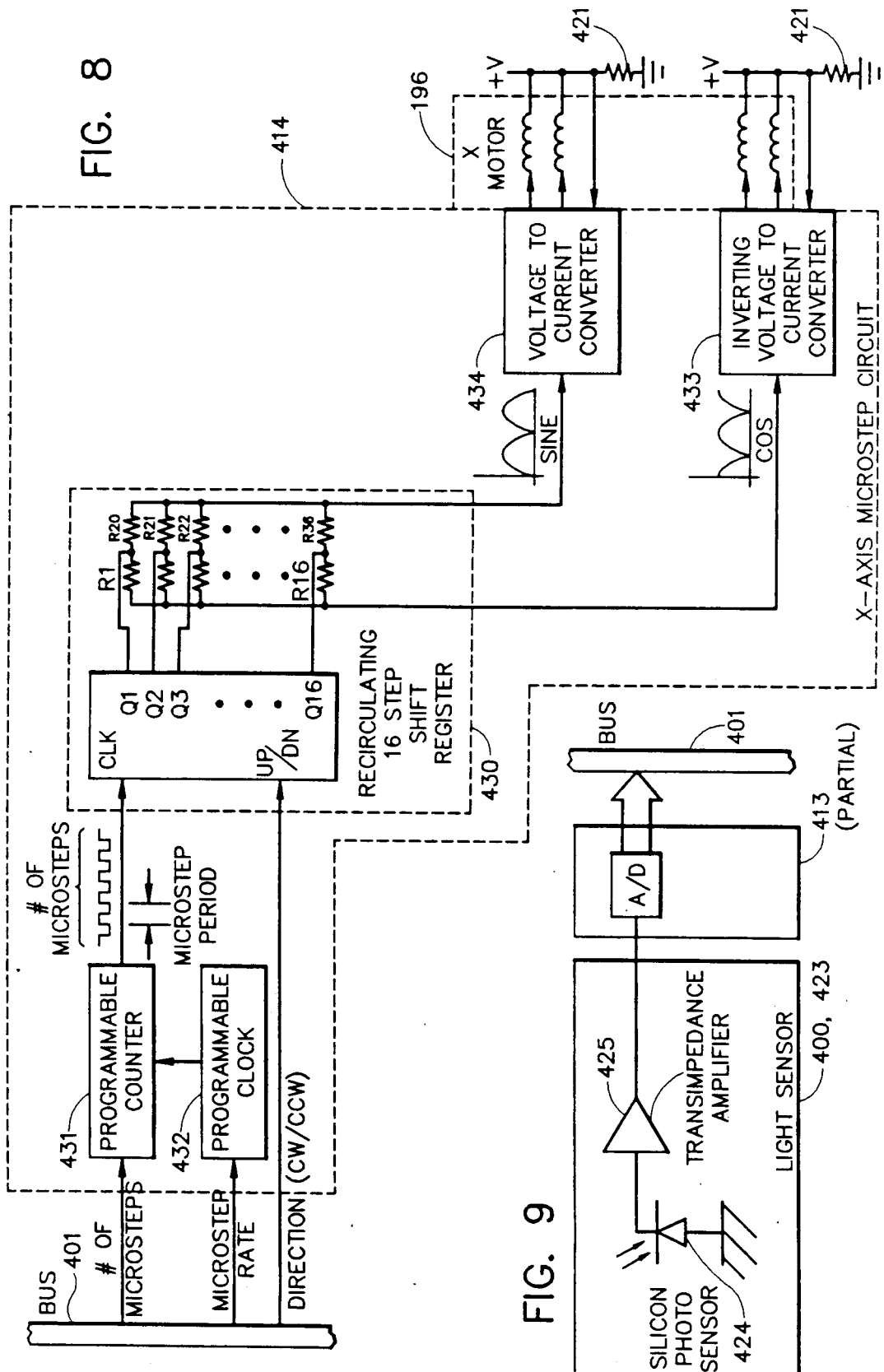

AUTOMATED OCULAR PERIMETRY, PARTICULARLY KINETIC PERIMETRY

This is a continuation of application Ser. No. 07/231,764 filed on Aug. 12, 1988 now abandoned.

TABLE OF CONTENTS

BACKGROUND OF THE INVENTION

1. Field of the Invention
2. Background of the Invention
    2.1 The Physiological Basis of Optical Perimetry
    2.2 Previous Methods of Surveying the Visual Field
    2.3 General Previous Instrumentation for Optical Perimetry
    2.4 General Performance of Previous Instrumentation for Optical Perimetry
    2.5 Specific Previous Instrumentation for Optical Perimetry
    2.6 General Requirements for an Improved Optical Perimeter
    2.7 Two Specific Requirements for an Improved Optical Perimeter

SUMMARY OF THE INVENTION

1. Purposes of the Invention
2. Perimeter Apparatus of the Invention
3. Reverse Kinetic Perimetry Method of the Invention
4. Modified Reverse Kinetic Perimetry Method of the Invention
5. Modified Threshold Perimetry Method of the Present Invention
6. Summary Advantages of the Present Invention

BRIEF DESCRIPTIONS OF THE DRAWINGS

DESCRIPTION OF THE PREFERRED EMBODIMENTS

1. Surveying the Visual Field
2. The Preferred Embodiment of an Ocular Kinetic Perimetry Instrument in Accordance With the Present Invention
3. Construction Details of the Ocular Kinetic Perimetry Instrument in Accordance with the Present Invention

CLAIMS

ABSTRACT

APPENDIX 1

APPENDIX 2

APPENDIX 3

BACKGROUND OF THE INVENTION

1. Field of the Invention

The present invention concerns measurement of the visual field of a patient's eye. The present invention concerns visual field testing wherein the patient's eye fixates on a moving point and the administration of test stimuli, and the recovery of patient response data, is automatic.

2. Background of the Invention

The present invention is concerned with a method of visual field testing, and with automated test instrumentation for performing the method. As background to the invention, the physiological basis of ocular perimetry, and the pathological conditions diagnosable by ocular perimetry, will be discussed in abbreviated form. Next, the prior art methods of surveying the visual field will be reviewed. Next, certain specific prior art instrumentation will be summarized. Finally, the problems with existing ocular perimetry measurement instrumentation, and the requirements for improved instrumentation, will be discussed.

2.1 The Physiological Basis of Ocular Perimetry

The optical system of the human eye projects a visual image onto the retina, just as the lens of a camera focuses an image on film. The retina transcribes the visual image into a neural code that is transmitted through nerve pathways to the visual cortex of the brain.

The human visual system is specialized into two broad divisions: (i) central or macular vision which is capable of resolving small detail and detecting color, and (ii) peripheral vision that can detect images in a panoramic as wide as 180° in the horizontal extent. An imaginary line of sight, the visual axis, connects the point of an eye's visual fixation on any given visual image to the fovea centralis. The fovea centralis is a small depression in the center of a retina area known as the macula lutea. The macula lutea is a highly specialized portion of the retina that can resolve details smaller than one minute of arc. The resolving capability of the macula outside of the fovea is less, and decreases with increasing distance from the fovea.

The receiving area for all macular fibers occupies about half of the total primary receiving area for visually afferent fibers. The remaining visual fibers projecting from areas of the retina that are peripheral to the macula are highly sensitive to light stimuli (when adapted to darkness) but their capacity for seeing fine details (visual acuity) is low.

This physiological structure of the human eye creates a vision field which is sometimes called an "island of vision", or a "hill of vision". The "island of vision" represents visual contrast sensitivity. It rises out of a surrounding "sea of blindness". The island shows a tall, narrow peak at its center. The peak, the point of visual fixation and highest visual acuity, represents the fovea, or retinal area of greatest resolution of visual stimuli. The size, or horizontal dimension, of the island is a measure of the extent of vision. The vertical height of the island is a measure of contrast sensitivity. The height of the island diminishes with distance from the peak (the point of visual fixation representing the fovea) just as the sensitivity of the extra-foveal retina diminishes. Beyond the edges of the island, or "shoreline", there is no sight because there are no rod or cone retinal receptors. No stimulus, no matter how strong, can be seen beyond the "shoreline" of the island of vision.

Pathologic conditions of the eye and/or brain, and the corresponding topography of the island of vision, may exhibit two types of defects: general and focal. A general defect in the island of vision is characterized by an overall diminution in visual sensitivity, or a reduced height profile of the island. This phenomenon occurs most commonly because the brightness or the clarity of an image is diminished at the retina. It may be due to (i) reduction of light entering the eye due to small pupillary opening; (ii) impaired media transparency due to corneal, lens or vitreous opacities; (iii) unfocused retinal image due to uncorrected refractive error, or (iv) reduced retinal sensitivity due to advanced age or high myopia.

Focal defects in the island of vision are characterized by deformities in its landscape. They are generally produced by disease in the neural portion of the visual pathway extending from the retina to the visual cortex.

There are two major types of focal defects: depressions and scotomas. A depression is an indentation of the surface of the island of vision. It shows up as a deformation of an isopter, or closed curve of equal contrast sensitivity derived as a horizontal slice through the island of vision.

On a horizontal slice, or isopter, through the island of vision a depression appears as an inward shift of a portion of that isopter—a warpage of the normal contour of that isopter. On a vertical slice through the island of vision the equivalent portion of the meridional profile will show a downward sagging.

A scotoma, or dark spot, is a pit, or well, in the island of vision. It is represented on a kinetic map as an area in which one or more targets are not perceived. It has a limiting border, which encircles and defines the defect on all sides. On static maps a scotoma appears as a trough in the profile.

The value of visual field testing of the eye is that it permits identification and localization of the responsible pathological condition. The localization of the pathological condition to a particular portion of the visual pathway is accomplished by a two step process: (i) identifying the relative attributes of the focal defects, and (ii) interpreting the meaning of these attributes in accordance with a knowledge of visual pathway anatomy.

A focal defect is defined by its location, shape, depth, and by the slope of its margins. The visual field of each eye is plotted on a chart that represents the visual space as the patient sees it. A commonly used combined chart shows the visual field seen by the patient's left eye upon the chart's left-hand side and the visual field seen by the patient's right eye upon the chart's right-hand side.

For each eye's chart section, perpendicular horizontal and vertical meridians that intersect at the central point of fixation conveniently divide the visual field of each eye into four quadrants. Coordinates in these quadrants are established both by radial meridians (defined by distance in degrees from the horizontal fixation meridian (0°–180°), and by circles of eccentricity (defined by the distance in angular degrees of their circumferences from the point of fixation).

Visual field testing plots the island of vision, including defects located therein, upon coordinate charts. When the plotted defects are studied as to location, shape, depth, and slope of margins, then the underlying pathological conditions giving rise to such defects may be diagnosed, and appropriate therapy applied.

2.2 Previous Methods of Surveying the Visual Field

Three methods are commonly used to survey the island of vision landscape, and to search for contour irregularities indicating visual defects. These visual test methods used to survey and map the visual landscape, or field of vision, are commonly called the (i) kinetic, (ii) static threshold, and (iii) static suprathreshold methods.

In kinetic perimetry a moving, kinetic, visual test target is advanced from a non-seen area outside the visual field radially into the visual field until it is first detected by the patient. The test target is of fixed stimulus characteristics, which stimulus characteristics represent a fixed height on the island of vision. Each time the test target is radially advanced toward the center of the visual field from a different direction a visual threshold point is mapped for the stimulus presented by that particular target. The joining of the visual threshold points so mapped forms a line of equal contrast sensitivity called an isopter.

Altering the brightness or size of the test target is equivalent to altering the altitude at which the island of vision is examined. For each different target brightness or size a different isopter will be mapped. In effect, the kinetic method of surveying the island of vision maps a series of horizontal slices through the island of vision. The outermost contour so mapped, beyond which even the brightest and largest test targets cannot be seen, represents the shoreline of the island of vision. Other isopters map the topological contours of the island of vision.

It will later be seen that at least two different adaptions of this previous kinetic perimetry method of surveying the island of vision are realized by the apparatus and method of the present invention. These adaptations will be called (i) reverse kinetic perimetry and (ii) modified reverse kinetic perimetry. They respectively represent the second and first preferred operational modes of the present invention.

A second previous method of surveying the island of vision landscape is the static threshold method. The static threshold method of surveying the island of vision probes various single points in the visual field with a static, or stationary, stimulus that is increased in brightness or size until the patient is first able to perceive it. The magnitude of the stimulus that evokes the first perception of the test target at any point defines the visual threshold at that exact point in the visual field. When this method is successively applied to a number of points, usually along a single meridian, then it creates a two-dimensional profile of the visual field which is equivalent to a vertical slice through the island of vision. This static threshold method is the most common previous method of automated testing of the visual field by computerized instruments.

A previous modification, being a simplification, of the previous static method of visual testing is the static suprathreshold method. In mapping visual fields by this previous method, the target's stimulus magnitude is set suprathreshold, or brighter than the normal expected threshold for each point upon the island of vision to be tested. If a suprathreshold level target is not seen, especially after repeated presentations, then the visual field at this point is presumed to be subnormal threshold, and abnormal. Static suprathreshold method testing is, therefore, not quantitative. It is primarily useful only to make a threshold determination that contrast sensitivity at a particular point in the visual field is either normal or abnormal.

It will later be seen that the static methods are not normally implemented by the visual field test apparatus of the present invention. However, it will later be seen that the apparatus in accordance with the present invention is fully capable of conducting complete, quantitative, static threshold perimetry and also static suprathreshold perimetry. Indeed, it is improved for conducting both. Particularly, in accordance with the present invention the method of conducting static perimetry (of either the static threshold or static suprathreshold types) will be modified. This (iii) modified static threshold and suprathreshold perimetry consists of the (static) presentation of stimuli at successive approximations, both sub- and supra-threshold, to the actual visual sensitivity at a point upon the island of vision. This conduct of modified static perimetry is not a preferred operational mode of the present invention.

As might be expected from an apparatus in accordance with the present invention that will be found to be sufficiently versatile so as to perform (i) reverse kinetic perimetry, (ii) modified reverse kinetic perimetry, and (iii) modified static threshold and suprathreshold perimetry, the apparatus will also be found to be capable of optionally performing, as still yet another method in accordance with the present invention. This method will be seen to employ some of the concepts of threshold/suprathreshold static perimetry in combination with (ii) modified reverse kinetic perimetry. This perimetry will be called (iv) modified reverse kinetic perimetry with successive approximations to points on the island of vision.

The pertinent point of all these methods (i) through (iv) is simply that the apparatus and methods of the present invention, while transcending conventional perimetry apparatus and methods, have a relationship to such prior apparatus and methods. The present invention thus requires an understanding of such prior apparatus and methods and their limitations.

2.3 General Previous Instrumentation for Optical Perimetry

Ocular perimetry testing is performed with test instrumentation. The earliest visual field test instrument is the tangent screen. Von Graefe first described the plotting of "indirect vision" on a blackboard in 1855. In 1889, Bjerrum popularized perimetry as part of the standard clinical examination using a two meter by two meter, flat plane, black velvet "tangent screen". The tangent screen has served as a standard backdrop for visual field examination ever since.

The tangent screen has been increasingly displaced since the middle of the twentieth century by the bowl perimeter introduced by Hans Goldmann. In bowl perimetry a patient views a target projected onto a hemispheric bowl while the perimetrist introduces stimuli manually and records visual thresholds. The advantage of the bowl perimeter is that it allows measurement of the full extent of the visual field under highly controlled and reproducible testing conditions. Available stimuli vary widely in size and intensity and can be quickly turned on and off. Background illumination is strictly calibrated. The featureless white interior of the bowl minimizes distractions. The fixation of the patient's eye may be monitored by telescopic view. The stimulus can be introduced more easily than with tangent screen examination, and the recording of points is more convenient.

Comparative disadvantages of the bowl apparatus, and advantages of the tangent screen apparatus, include that only one testing distance is available (approximately one-third meter) with the bowl apparatus. Further, the size of the central field measurable by a bowl apparatus may be less than the size obtained with the standard tangent screen.

Conversely, the previous tangent screen apparatus also exhibits disadvantages. However, there is nothing intrinsically inferior with the tangent screen apparatus if its disadvantages can be overcome. (Insofar as the perimeter in accordance with the present invention resembles a tangent screen, it will later be seen that these disadvantages are substantially overcome.) One disadvantage with the previous tangent screen apparatus has been that (i) the ambient lighting, (ii) the stimulus intensities, and (iii) the rate of target movement were not truly uniform from one examination to another or from one test room to another. The apparatus in accordance with the present invention will later be seen to be used in a room of controlled ambient light intensity level, and to support the proper setting of this ambient light intensity. Moreover, it will be seen that during administration of testing in accordance with the present invention both stimulus intensity and rate of target movement will be strictly controlled and repeatable.

It should be noted that previous tangent screen devices of the type that use projected stimuli have also been able to accurately and repeatably control the rate of target movement in order to cause the appearance and disappearance of these targets within the field of vision. However, projected stimuli tangent screen devices lack standardized background and stimulus illumination, and they do not examine the entire peripheral visual field. These limitations will later be seen to be overcome by the apparatus in accordance with the present invention.

Another problem with use of the previous tangent screen apparatus has been that the examiner remains in full view of the patient and serves as a distraction to the patient's required maintenance of focus fixation. It will later be seen that the distraction of examiner is eliminated in the apparatus and methods in accordance with the present invention. Moreover, the problem with patient focus fixation, and with the monitoring of patient focus fixation, will also be seen to be substantially eliminated in the apparatus and methods in accordance with the present invention.

2.4 General Performance of Previous Instrumentation for Optical Perimetry

Automated and semi-automated visual field testers have been used in clinical practice since approximately 1970. Stimuli in these devices are not introduced by hand, but are instead introduced by displaying charts marked with fluorescent spots, or by turning on lights, or by projecting white spots on a screen or bowl. In some cases a computer directs the program of stimulus presentation (the test regimen). The particular test regimen may be, in some cases, directed to the detailed analysis of a specific suspected pathological condition of the eye.

Commercially available "automated" visual field instruments fall into general categories. Certain non-computerized instruments, available at relatively lower prices of a few thousand dollars, enable the performance of the static suprathreshold and the static threshold methods in an approximate test time of four minutes per eye. One computer-assisted instrument only serves to guide a manual examination, via threshold kinetic and static suprathreshold stimuli, in a normal visual examination lasting 20–40 minutes per eye.

Next, fully computerized suprathreshold visual field instruments, available at the cost of many thousands of dollars, perform static suprathreshold visual field testing at an approximate elapsed time of seven minutes per eye.

Finally, computerized static threshold visual field instruments are by far the most expensive, having prices ranging to $25,000. These instruments allow the performance of static and kinetic threshold tests at a test time of approximately 40 minutes per eye.

Curiously, data regarding instrument cost versus the test time for visual field instruments generally indicates a positive correlation, with increasing instrument cost resulting in increasing test time. This is contrary to the desired relationship. Administrators of visual field testing would seemingly be willing to pay more for an instrument that conducts visual field testing more efficiently in a shorter time.

The obvious explanation for the present positive correlation of instrument cost versus test time is that the more expensive instruments, and longer test times, perform visual field testing in a more thorough and exact manner. This is despite the fact that an initial, threshold, screening of the normalcy and acuity of the visual field could in many cases be conducted relatively quickly if a visual field test instrument were to be sufficiently effective in supporting this simple threshold screening. A mere seventy (70) data points on the landscape of the island of vision suffice for thorough threshold screening for visual defects. This simple concept deserves to be well considered. To repeat, seventy (70) accurate data points suffice for testing the human visual field sufficiently so as to identify the existence or non-existence of pathological conditions.

Yet previous threshold testing of visual acuity requires (i) skilled personnel, (ii) expensive instrumentation and (iii) up to forty (40) minutes to make this identification of the existence or non-existence of pathological conditions. There is obviously a problem in the previous apparatus and methods in getting the data on the requisite seventy (70) points. This problem is fundamentally rooted in the previous test regimens (as discussed in previous section 2.3) and in the instruments supporting these regimens (as discussed in this section). The test regimen of the present invention will be seen to be much better optimized and efficient in surveying the visual field. It will be seen to allow automated derivation of eighty (80) points in under four (4) minutes by employing new test regimens administered by new test instrumentation.

Of course if a defect(s) is(are) preliminarily detected during threshold screening, then it (they) may need to be further localized, quantified, and mapped with great precision —implying a continuing comprehensive and exacting testing at least in the local area(s) of the perceived defect(s). An apparatus supporting visual field testing would optimally be very quick and efficient in some operational mode for simple threshold screening for visual defects. Meanwhile the apparatus would also, when operated in another mode(s) which might differ in any of the type, duration, regimen, or number of data points in the test, be capable of the most detailed and exacting testing directed to analysis of a particular defect and associated pathological condition. The perimeter device in accordance with the present invention will be seen to so function.

2.5 Specific Previous Instrumentation for Optical Perimetry

Only one known prior art instrument provides computerized kinetic threshold perimetry that is computerized in data acquisition somewhat similarly to the scheme implemented by the present invention. This instrument is the Perimetron TM perimeter that was available from Coherent, Palo Alto, CA, circa 1983, at a 1983 cost of approximately $48,900. It enabled the performance of kinetic threshold and static suprathreshold visual field testing at an approximate test time of forty (40) minutes per eye. The perimetron used a bowl perimeter. It essentially automated the application of stimulus from various positions within the bowl. Although automated, the Perimetron TM perimeter has not, as a bowl-type perimeter, performed the preferred perimetry methods of the present invention.

A successor machine to the Perimetron TM perimeter is the Humphrey Field Analyzer (HFA). This device initially performed static perimetry by steering a light beam (when off) within a bowl perimeter and then turning the light beam on when it is at predetermined fixed locations. An improvement to perform kinetic perimetry in the HFA is announced circa 1988.

Additional prior art perimeters are shown within various U.S. patents. U.S. Pat. No. 4,063,807 to Gelius, et al., discloses a parametric eye examination device having light-emitting diodes (LEDs) which are controllable for brightness. This device uses a hemispherical inner surface holding the lights. The instrument has a stationary fixation point which the patient stares at. One of one hundred and twenty-seven (127) LEDs is randomly presented to the patient. The patient indicates whether or not he/she has seen the illuminated LED by depressing a button. The test may be repeated with lights at different levels of brightness.

U.S. Pat. No. 4,421,393 to Cohen, et al., describes a visual field perimetry device where the patient is seated in front of a semi-circular light bar having a plurality of LEDs located around the inner circumference. Pairs of the LEDs are randomly energized. The patient manipulates a force-control stick that provides a nulling signal for illuminating various pairs of LEDs. The patient's head is secured in a helmet rigidly fixed to the back of the seat to prevent side-to-side head movement.

U.S. Pat. No. 4,346,968 to Melin, et al., discloses a conventional visual field testing system having a center light at which the patent is instructed to look with one eye during the examination. Other lights or series of lights are illuminated during the test and the patient indicates which of the lights he sees.

U.S. Pat. No. 4,059,348 to Jernigan discloses an instrument which includes a mirror that positions a target beam of light sequentially at selected locations on a board. In one embodiment, a Polaroid photo allows immediate inspection after a test is made. The patient's eye is to remain fixed on a stationary point. However, movement of the eye is monitored.

U.S. Pat. No. 4,421,392 to Pitts Crick, et al., discloses a perimeter for testing visual field light sensitivity that presents a moving spot or set of fixed spots visually to the patient. The patient fixes on an aperture on a card. A number of patterns having different gradations of density are made to appear. Patterns having gradations of density are used as a means of assessing contrast sensitivity. Again, the patient has to have his eye fixed on a particular point of reference.

U.S. Pat. No. 2,564,794 to Shekels describes a vision plotting device. In operation, the patient fixes on a target and indicates when he sees a beam of light which is intermittently projected through a number of apertures in a backing plate. A recording head positioned over a chart is actuated when the patient holds his finger on a key to print a spot where he sees a dot of light. Thus each time a dot of light appears on the screen which the patient sees, a corresponding dot is printed on the chart. If the patient does not observe a light dot on the screen at any particular point when a light dot is displayed, then there is no record the dot was seen.

U.S. Pat. No. 4,558,933 to Murr discloses a visual field testing device having a concave screen and selectively illuminated LEDs.

U.S. Pat. No. 4,392,725 to Sheingorn discloses a visual field testing device having sequentially illuminated LEDs and a memory unit for recording and displaying test results.

U.S. Pat. No. 4,634,243 to Massof, et al., discloses a glaucoma detection device which has a random dot background field and a movable stimulus pattern. A patient views a video display corresponding to the entire human field of normal vision. A random dot pattern is generated on the display. A smaller fixed stimulus pattern is superimposed on the random pattern. The fixed pattern is then moved in the random pattern and the patient presses a response key to indicate whether or not he sees the fixed pattern. This produces a hard copy printout of the test.

2.6 A Specific Previous Method of Perimetry

A previous method of visual field examination of relevance to the present invention is described by Bertil E. Danato in the paper "Oculokinetic perimetry: a simple visual field test for use in the community" appearing in the British Journal of Ophthalmology, Volume 69 (1985) pp. 927-31. The paper describes a method of visual field examination which enables an unsupervised person to carry out self-assessment using only a paper test chart, a record sheet, and a pencil. It is entitled 'oculokinetic perimetry' because it is the subject's eye that moves and not the test target. However, the subject's eye moves only because the subject is told to move his/her eye, essentially by looking at and reading aloud a series of numbers, typically from 1 to 100, that are printed in a particular pattern somewhat like a starburst. As the subject looks at, and reads, each number he/she is also supposed to himself/herself note the detection or disappearance of an unmoving central test stimulus, normally a simple dot, by recording a record sheet. The record sheet typically presents numbers in respective positions as are the numbers upon the oculokinetic visual field test chart. The subject is directed to indicate that a central stimuli is not seen while the subject is (ostensibly) looking at a number by crossing out the corresponding number on the record sheet.

This self-administered test is very, inexpensive. It is alleged to provide non-ophthalmic health care workers with a simple means of performing perimetry in the community, and to allow susceptible people to carry out self-assessment of the visual fields at home. The test is intended to facilitate the detection and management of glaucoma, especially in underdeveloped countries.

Unfortunately for the simplicity and low cost of oculokinetic perimetry, it is extremely difficult for even intelligent, motivated, diligent, and well-instructed people to perform correctly. It is exceedingly difficult for a person to consciously look only in one place—the target number—located amongst many equally visually detectable equally enticing like places—the other target numbers—while supposedly determining as to whether or not still another place —a none too distinctive constantly visible central dot stimuli—is visibly detectable in the peripheral field of a one eye's vision. The instinct, and showing, of the paper—that an alternative method of visual field examination wherein it is the eye, and not the test stimulus, that moves would be of good value—is indisputably correct. The implementation solely by presentation of a test chart and delivery of directions for use has not, however, proven successful in realizing this potential value.

2.7 General Requirements for an Improved Optical Perimeter

An improved perimeter for measurement of the human visual field will preferably satisfy a number of requirements substantially unrelated to the test regimen administered. The perimeter instrument should be fully automated with respect to both the presentation of stimuli and the monitoring of patient response. The entire visual field testing should be performed without technician involvement, such as being automated by a microprocessor. The perimeter in accordance with the present invention will be seen to be fully automated.

If a tangent screen, as opposed to a perimeter bowl, is employed then certain deficiencies in the tangent screen should be addressed. With a tangent screen it is generally difficult to have the background illumination even and calibrated; the screen instead exhibiting "hot spots" and dark areas. Since perception of a stimulus depends on the difference between target and background illumination, an even and known illumination throughout the field is critical. This problem can be, however, obviously overcome if the background illumination is precisely maintained, and if the stimuli illumination is calibrated. The calibration of the stimuli should preferably be done automatically. The perimeter in accordance with the present invention will be seen to sense and display background illumination. It will also be seen to automatically calibrate illumination stimuli.

Next, a tangent screen generally tests only the central field of vision as opposed to supporting testing of the total field of vision (such as may be performed with a bowl perimeter). A few eye diseases impair vision only in the peripheral visual field. The evaluation of this field is correspondingly necessary. It is possible to test the entire limits of a patient's field of vision with a tangent screen, but (i) the screen must be appropriately large, (ii) and the presentations upon such screen must be appropriately extensive, and (iii) the fixation point must be moved from its normal dead-ahead position. What is possible is, in practice, extremely uncommon. Particularly, the fixation point is seldom displaced from its reference position during performance of kinetic perimetry upon a tangent screen. Use of a tangent screen to test the far limits of a patient's field of vision is usually entered into only after a closer-in visual field detect has been detected, and even then typically only of the far visual field in the direction, or quadrant(s), of such defect.

The perimeter in accordance with the present invention will be seen to test the entire field of vision while simultaneously being of reduced size. Moreover, it will test the entire field to its furthest extent during the routine, high speed, test of the visual field. No special subtests for far field regions will be required, as is common in prior perimetry.

Finally, when a target moves away from the point of fixation on the flat plane of a tangent screen then it becomes further from the patient's eye. This causes it to subtend a smaller visual angle and appear to be less bright. This is to be contrasted with the spherical screen of a bowl perimeter, where the patient's eye is located at the center of the hemispheric bowl and where the distance to targets, and the visual angles subtended by these targets upon the hemisphere of the bowl, is always the same. It should be recalled that the shoreline of the island of vision is defined as that boundary beyond which no visual stimuli, no matter how bright, can be seen. Consequently, if the objective is only to identify the shoreline of the island of vision, then there is no limitation to the use of a bright source moving on a tangent screen in order to do so. Normally, however, the objective is broader: to map the island of vision.

To meet the broader objective of mapping the island of vision by kinetic perimetry performed upon a tangent screen the target must be controlled in size and/or intensity. But this is difficult. A target stimulus on a tangent screen is normally produced by an incandescent lamp. It is hard to controllably repeatably obtain a dynamic range of intensities which is sufficiently large. Consider the vastly different elevations upon the island of vision. The ratio elevations representing visual sensitivity, is on the order of 10,000:1. Then consider where the brightest and most intense target source must be shown. It must be shown at the periphery of the island. Next, consider where the periphery of the island of vision lies on a tangent screen when the eye is fixating straight ahead. The periphery is far off to one side, and/or far off in elevation, and/or far off in depression from the central axis. Finally, consider what happens when a projection light source aligned along a central axis (or substantially along a central axis) is projected so as to produce a target upon the tangent screen in a position far off the central axis. The light reflects from the screen at an oblique angle. Little light returns to the eye. Producing a sufficiently intense target at the periphery of a tangent screen, at least by light projection, is very difficult.

The present invention will be seen to deal with this problem. The perimeter in accordance with the present invention will be seen to adjust the intensity of the test stimuli to compensate both such that should they (i) subtend substantially different visual angles, and (ii) should be presented at different distances from the fixation point. The test stimuli will be seen to be rear projected, and not incandescent. The test stimuli will rather be seen to be light sources that are precisely controllable over a suitably wide range of illumination intensity.

It is a further requirement of automatic test instrumentation for examination of the field of vision that test stimuli at various illumination intensities should be numerous, and should readily occupy all positions necessary in order to accurately profile the island of vision. Generally, a goodly number of targets are required for mapping the island of vision by the static threshold and the static suprathreshold methods. However, in the previous kinetic perimetry method the number of generated optical stimuli, and their respective discreet positions, were required to be, and generally were, even more numerous and dense. The spatial density of targets at appropriate distributions of intensities should particularly always be realizable at levels that exceed the requirements of any particular, directed, test strategies which concentrate examination within certain areas of the field of vision. The perimeter in accordance with the present invention will be seen to be capable of presenting selectable intensity stimuli of essentially infinite numbers at infinite positions at all appropriate intensities. In other words, there is no present or foreseeable future test involving the presentation of visual stimuli to the eye that the perimeter in accordance with the present invention cannot perform.

In accordance with a desired capability to present diverse stimuli at diverse locations, an automated perimetry instrument should be versatile. A variety of (presumably software) programs for directing the presentation of particular stimuli should be available. These programs should execute in a substantially automated manner so that the operator of the perimeter need not learn, and relearn, special techniques of perimetry.

An automated perimetry instrument would preferably store patient response data and enable its retrieval at a later date. The data should be able to be recorded in a permanent record, such as by printing, and should be easily interpretable in such record form. It would optimally be the case that the perimeter itself would aid in the interpretation and reduction of this data. Mainly, the ocular test strategies could have built-in methods for estimating threshold fluctuations and patient reliability. For example, the automated perimeter could have stored in its memory age-standardized data from a large number of normal subjects in order to facilitate comparison of test results. Programs could be available that would permit the statistical comparison of data from tests between different subjects, and at different times upon the same subject.

The perimeter in accordance with the present invention will be seen to be programmable, essentially as easily as a personal computer. Because of its easy programmability, it will be seen to be capable of doing anything with perimetry test data that a personal computer could do, including all sorts of graphical presentations, statistical analysis, comparisons, and/or archiving.

2.8 Two Specific Requirements for an Improved Optical Perimeter

The requirements for an ideal automated perimeter obviously present a spectrum between the more obtainable and the less obtainable, between the more expensive and the more economical. However, at least two crucial specific, requirements appear possible of being addressed in a substantially improved manner.

The first of these requirements is the accuracy, and continuity, of the patient's visual fixation throughout the occasionally lengthy visual examination. Accurate fixation is a fundamental requirement for accurate perimetry. Exactly how accurately it should be expected that the patient should fixate, and continually fixate, is uncertain because little research has been done about the effect on parametric accuracy of tiny shifts in fixation. However, it is well known that fixation is never absolutely steady, even for the most conscientious and well-trained subject, and that some tolerance for small drifts in patient fixation is necessary during measurement of the visual field. In the prior art visual field testing determinations and redeterminations were readily tolerated which deviated by 3° or 4° in the circles of eccentricity from one determination to the next.

The prior art approach to insuring the best possible continuing patient fixation has been to monitor such fixation by one of several methods. The simplest method, although not automatic, was to have the technician view the patient's eye through a telescope or a television monitor. Some instruments use a "blind spot" method to monitor fixation wherein a stimulus is presented in the blind spot of the field of vision at sporadic intervals and, if the patient sees this stimulus, then it is an indication of poor fixation. Of course, it should be remembered that the blind spot itself is approximately 7° by 9° in the visual field. Exotic eye positional monitoring systems, such as those used by pilots in aiming the armament of a fighter plane, are also possible. The present invention will be seen to present a scheme of assuring accurate fixation which substantially alleviates any necessity of monitoring the fixation of the patient's eye. Nonetheless fixation will be seen to be checked in the present invention by presentation of an occasional stimuli in the blind spot—similarly to previous fixation monitoring methods.

Prior art, constant fixation, visual field test methods create a great problem by making a fixation requirement upon the test subject which is demanding under the best of circumstances, which is randomly violated without knowledge of the test administrator and sometimes even without knowledge of the subject, which is highly perturbing to test results, and which is a general source of inaccuracy in visual field determinations. As previously stated, this inaccuracy is on the order of 3° to 4° minimum. Few medical observers of radiograms, CAT scans, sonograms and like medical records that are presented in graphic form would tolerate 3 or 4 degrees random deviations—both within the overall image and at totally random portions thereof—from one observation to the next observation.

Impreciseness in measurement of the visual field may occasionally mask early recognition of subtle ocular pathology conditions, especially at the periphery of the retina. It is highly desirable that, short of tapping into the magnetic emanations of the optic nerve (such as by superconducting quantum interference devices) in response to optical stimuli, that the patient should be administered a visual field testing regimen that (i) can readily and easily be followed, (ii) is not readily subverted by malingering or subterfuge, (iii) is quick and efficient and totally automated, and most importantly, (iv) delivers repeatable results of improved accuracy and consistency. The improved visual field test method and apparatus in accordance with the present invention will be seen to realize these desires.

A second requirement that is susceptible to being addressed with substantial improvement is the initial cost, and life cycle operational cost, of automated perimeter instruments. Some of the most expensive perimeters cost approximately $25,000 and use continuous skilled technician/perimetrist labor during test administration sequences lasting up to 40 minutes per 2 eyes. These costs require that each of 6 patients per day (a nearly continuous usage) must be charged $155 to $160 for the perimeter-owning organization to break even. This budget includes approximately one-third of the test fee amount to pay for the cost of the perimeter instrument and the remaining two-thirds to pay for upkeep, repairs, overhead and technician labor. If the perimeter instrument were to be of substantially lower initial cost and, even more preferably, the requirement for skilled technician labor were to be reduced, then the cost of performing visual field examinations could be considerably reduced.

A perimeter would preferably conduct threshold visual acuity screening very rapidly, and would preferably also conduct detailed surveys of the island of vision (or sections thereof) rapidly. These requirements are in tension with the situation in the prior art where accurate perimetry for either threshold testing or for detailed diagnosis of the visual field requires numerous data points that vary in both spatial displacement and in intensity (especially for kinetic perimetry). These numerous data points have required commensurately lengthy time durations to gather the patient's response to the stimuli at each data point.

Short of sensing electrical impulses on the optic nerve for a fully automated man to perimetry-test-machine interface, the patient cannot be expected to give a response to visual stimuli at rates much higher than once every two seconds. Even if the patient's response is by voice, and even if the response is information-rich by having the patent state numbers "zero", "one", "two", etc. instead of just "yes" or "no", the patient can only give so much information before he/she fatigues, loses interest, or fails to cooperate. The test regimen conducted by the perimeter has to be very well thought out in order to get as much information as is possible as quickly, and as effortlessly to the patient, as is possible. The preferred visual field test regimen in accordance with the present invention will be seen to give, in only four (4) plus eighty (80) quickly derived data points, an excellent quantification of the field of vision.

The rapidity with which the perimeter in accordance with the present invention will extract quality information from the patient is of such a different order from prior perimeters that modern developments in the area of audiological testing should be considered by analogy. The days are past when an audiologist presents a tone at a certain frequency and volume and asks "Can you hear it?". Modern audiological test machines monitor rapid patient pushbutton responses to complex tonal and volume patterns like "dah dit-dit-dit-dit... Dah Dit- Dit-Dit-Dit... DAH DIT-DIT-DIT-DIT... DAH DIT-DIT-DIT-DIT... <u>DAH DIT-DIT-DIT-DIT</u>", etc. Conceptually, the fundamental difference between modern and antiquated audiological testing is the informational transfer rate, or density, at which data is recorded to a machine system regarding the patient's physiological auditory system. The present invention will enhance the efficiency and economy of gathering information regarding the patient's more complex visual system by roughly an order of magnitude over previous approaches, typically making a comprehensive quantitative eye exam roughly as fast and as inexpensive as a hearing test.

Accordingly, new approaches to the methods of performing ocular perimetry, and new automatic perimeter instruments for performing such methods, are desired.

SUMMARY OF THE INVENTION

1. Summary Statement of the Invention

The present invention contemplates moving the visual target to which the (moving) eye is fixated instead of moving the test stimulus. This confers the advantages of (i) permitting the simultaneous presentation of multiple test stimuli for much faster testing and much reduced patient fatigue, and, in the preferred embodiment, (ii) using a common, fully automated, mechanism both to perform the visual field testing and to record the results thereof.

2. Summary Outline of the Apparatus and Principal Methods of the Invention

The present invention is embodied in improved methods, and in a perimeter apparatus, for surveying the visual field of a patient's eye.

The perimeter apparatus of the invention presents visual stimuli on a plane similarly to a tangent screen, but is preferably enclosed in a housing like the enclosure of a bowl perimeter. Extensive test methods, and preferred test regimens in accordance with such methods, are entirely automated under control of a computer. Patient responses upon presentation of visual stimuli are preferably audible, and are spoken into and understood by the perimeter. The perimeter generates hardcopy graphics output of test results for analysis by a trained professional. The perimeter in accordance with the invention could perform any and all of the previous methods of perimetry, and would be of high performance and cost effectiveness in so performing. A coordinate strength of the present invention concerns, however, the new methods of perimetry that are preferably performed by the new perimeter apparatus.

A first, base, method of the present invention is a reverse of kinetic perimetry. A visual stimulus, called the target stimulus, to which the (moving) eye is fixated is moved. The test visual stimulus (stimuli)—regarding which the recognition(s) or non-recognition(s) by the patient is (are) indicative of visual sensitivity at tested points within the visual field—are not moved. This will be recognized to be the reverse of kinetic perimetry wherein the target stimuli is fixed while the test stimuli are moved. This method is accordingly called reverse kinetic perimetry (RKP).

This RKP method is totally and generally efficacious for visual field examination. However, it is preferably used in relation to other methods of the invention only for the limited purpose of plotting the blind spot of the visual field. Still other, second and third, methods that are each still further modifications of reverse kinetic perimetry will preferably be used for actual testing of the visual field. If a defect causing a blind area within the visual field is uncovered during such testing then detailed delineation of that area may still preferably be done using reverse kinetic perimetry.

A second, mainstay, method of the present invention is called modified reverse kinetic perimetry (MRKP). MRKP differs from reverse kinetic perimetry (RKP) in that the test visual stimuli (which are positionally fixed) are not continuously illuminated, but are only momentarily illuminated at times. The patient's recognition or non-recognition of these illuminations, as indicated by his/her responses, are correlated in the perimeter with the locations and intensities of the moving fixation target stimulus and fixed test stimulus(i) in order to test and to plot the visual field of a patient's eye.

A third method of the present invention, called modified reverse kinetic perimetry with successive approximations to points upon the island of vision (MRKP-SA), is actually preferably performed in time sequence after the first method but before the second method. This third method is preferably used for the limited purpose of precisely deriving just a few points, typically four, within the patient's eye's visual field and upon the island of vision. These few points permit recognition of what the patient's eye should always see if it were everywhere normal. The points are used to define a reference island of vision to the actual visual sensitivity of the eye.

This reference island of vision is intended to be sized and adopted by the extrapolation from the four points. It is usually of smaller size than the actual island of vision. It is thus referred to as a "shrunken" island of vision. It should be understood, however, that the "shrunken" island of vision is simply a customized reference island of vision for a particular subject. If the subject exhibits greater than normal visual sensitivity at the four points then his/her "shrunken" island of vision may actually be larger than the normal for the subject's age.

Subsequent MRKP testing with the second method, given knowledge of this "shrunken" island of vision proceeds very rapidly. It typically derives the entire visual field of the eye in only eighty (80) test points that are typically derived in twenty plus (20+) test iterations that typically transpire in less than four (4) minutes.

All three methods, and still other methods of testing the visual field in accordance with the present invention, are individually fully capable of testing the entire visual field, and each method alone is generally of superior efficacy relative to previous methods for so doing. The preferred combination of the three new methods and a fully automated perimeter apparatus permits in aggregate, however, that precise, repeatable, reliable, low-cost testing of the visual field is routinely performable in an unprecedentedly short time, usually less than four (4) minutes per eye and potentially as fast as thirty (30) seconds for some simpler tests.

3. Perimeter Apparatus of the Invention

The preferred embodiment perimeter apparatus in accordance with the present invention has a picture-size flat rear-projection screen that is preferably mounted in a light-controlled enclosure. In an alternative embodiment the screen may be mounted on a wall in front of the patient. Various fixed and moving light sources at the rear of the screen are both selectively moved and illuminated under computer control for rear projection on the screen.

The perimeter presents a first light source, normally a single light emitting diode ("LED") but sometimes a small cluster of LED's, which is (are) commanded by a computer to (jointly) positionally move on the rear-projection screen. The first light source(s) is (are) typically red in color. The movement is accomplished by means of x-y axis step motors that induce movement similar to that of computerized drafting plotter.

The perimeter further includes a plurality, typically sixteen (16), of positionally fixed "test" or "stimuli" second lights located behind the rear-projection screen. Each of the "test" lights is typically 580 nanometers yellow light in color. One or more, typically four (4) of the "test" lights are caused by the computer selectively momentarily illuminate when it (they) are at various locations relative to the "target" light. The illuminations may be momentary or prolonged in accordance with the particular test regimen that is being performed (discussed in the following sections). The light intensity of all illuminations, whether prolonged or momentary, is strictly controlled.

At the time(s) of its illumination(s) each of the positionally fixed "test" light sources occupies an individual location in distance and in angle relative to the then existing position of the moving "target" light source. The patient responds to each "test" light source for which he/she detects the illumination(s) by a spoken response or, alternatively, by actuation(s) of a multi-position or pushbutton switch. If more than one "test" light source is simultaneously illuminated (as is typical) then the patient verbally indicates the number of light sources that are seen by verbally speaking a number. If multiple "test" light sources are simultaneously momentarily illuminated, and if not all are seen by the patient, a more detailed search is later conducted to individually identify the individual "test" light sources that are, and that are not, seen at any particular position of the moving "target" light source.

The computer that is causing the moving of the first, "target" light source, and that is also controlling the illumination(s) of one(s) of the second, "test" light sources at various positions of the "target" light source, both receives and records the patient's response data to the visual test stimuli of the "test" light source(s). Because the computer knows the relative positions in angle and in distance between the moving "target", light source and each of the one or more "test" light sources, and because it knows the intensity of the "test" light sources, it is able to calculate the visual field of the eye of the patient. This calculated three dimensional visual field, typically represented by the threshold perimeter shoreline of vision and several isopters on the island of vision, is plotted in two dimensions by the computer using the same x-y axis plotter mechanism otherwise used to move the first, "target", light source. All testing and plotting transpires in a completely automated manner.

For this reason of using one mechanism both to move a "target" light and to plot the test results, and for smoothness and for flexibility in all paths that are traced, the movement of the "target" light and/or the plotting of results preferably transpire by electromechanical, and, not solely by electronic, means. It will of course be understood that the moving target light(s) could be implemented electronically, such as by a television display. In such case the "target" lights might also appear on the television, or might be positioned in front of the cathode ray tube. It is alternatively possible that the moving "target" light might be implemented as a matrix consisting of multiplicity of positionally fixed lights and that the moving may proceed stepwise by successive illuminations amongst the lights, normally stepwise from light to light. The moving "pursuit" light might even appear on television.

If the perimeter screen is not enclosed, which it normally and preferably is, then the perimeter senses and displays the level of ambient, room, illumination in order that both (i) the room illumination may be better adjusted, and (ii) the light intensity of the "test" light stimuli may be adjusted in consideration of the actual ambient illumination.

The perimeter also displays messages, and prompts, to guide (to the limited extent necessary) conduct of the testing and also to indicate the stepwise progress of testing.

4. Reverse Kinetic Perimetry First Method of the Invention

The preferred embodiment of a perimetry apparatus in accordance with the present invention selectively performs, under software control, a reverse of the kinetic threshold method of visual field examination. This method is called reverse kinetic perimetry (RKP).

This RKP first method of the invention is not the most prevalent operational method of the perimeter for assessing visual sensitivity in terms of either the amount of time typically spent on the method or the amount of data typically derived with the method. The reason that the RKP method is not exclusively, or more often, or longer used is not because the method suffers from any inadequacies in determining the visual field, especially by comparison to all previous methods. The RKP method is preferably used for only a limited, but important, purpose in the present invention because its derivatives are even more powerful. This limited purpose is the location of the centroid, and the determination of the area of the blind spot, of the eye. The RKP method is first discussed in this section, however, in order that further, even more sophisticated, methods of the invention presented in later sections 4. and 5. may be better understood.

It should be recalled that in standard kinetic perimetry, a test stimulus is moved into the visual field of a patient's eye that is fixating straight ahead on a target stimulus. Reverse kinetic perimetry (RKP) in accordance with the present invention proceeds by moving an illuminated first, "target", source of light in order that it may be substantially continuously followed by, and substantially continuously visually fixated to the fovea of, the patient's eye. Simultaneously to this tracking of the moving first light source by the patient's eye a second light, the "test" light stimulus is continuously illuminated. The second light assumes various distances of separation from, and angles relative to, the moving first source of light.

The patient is queried to indicate those periods that he/she does or does not visually detect the continuous illumination of the second light while visually fixating upon the moving first light. Each change (in either sense) between periods of detection and periods of nondetection constitutes a temporal juncture. The relative positions, in both distances of separation and relative angles, of the first and of the second sources of light are recorded upon at least some, and normally on all, of these temporal junctures. The aggregate recorded relative positions thereby indicate the visual field of the patient's eye.

It should be recognized that the RKP method accords an expanded angular range relative to normal, fixed central fixation, kinetic perimetry. Particularly, when the test light stimulus is initially outside the visual field when the target stimulus is at its initial, reference, position but later moves into the visual field during moving of the target stimulus then testing may transpire to at least 60° in the nasal direction despite the presence of the patient's nose, to at least 60° superiorly despite the presence of the patient's brow, and to at least 75° inferiorly despite the presence of the patient's cheek.

In the preferred testing in accordance with the invention, a test stimulus is illuminated within the blind spot of the eye's visual field. The target stimulus is progressively moved until the test stimulus becomes seen by the patient. This is repeated so that the test stimulus exits the blind spot in different directions, typically at the four points of the orthogonal axis. The typical four points identified by the RKP method at the periphery of the blind spot of the eye define both the centroid and area of the blind spot.

5. Modified Reverse Kinetic Perimetry Second Preferred Method of the Invention

A second preferred method of the present invention for visual sensitivity, or visual threshold, screening is a modification, adding further sophistication, to the reverse kinetic perimetry (RKP) method described in the previous section. This second preferred method is called modified reverse kinetic perimetry (MRKP). It is a predominant operational model of the perimeter, being used to test some eighty (80) points within the field of vision. It is not, however, that test method that is secondly executed in the preferred testing sequence executed by the perimeter. That method, a third preferred test method, is even more sophisticated than MRKP. The MRKP second preferred method is accordingly discussed in this section in order that the third preferred method discussed in the next section 6. may be better understood.

In MRKP the second source of light is not continuously illuminated for the prolonged time duration during which the field of vision makes excursion onto the position of the second light source (by act of the eye's fixation following the moving first light source). Instead, the second light source is only illuminated momentarily at times. At these times the second light source is at predetermined distances of separation from, and angles relative to, the first source of light. The visual detection or non-detection of the second light's momentary illuminations by the patient is recorded. The recorded detections and non-detections are correlated with the corresponding distances of separation and angles between the at least one second light and the first source of light in order to determine a threshold sensitivity of the patient's eye to the illuminations.

A major advantage gained in MRKP is that multiple second, test, light sources may be simultaneously presented. The information on the patient's recognition of these simultaneous presentations may be simultaneously retrieved, such as by the patient's speaking of a single number "one", "two", "three", etc. The informational density of testing, and of data retrieval, is thus magnified in MRKP over all previous methods of perimetry that essentially obtain data upon only one point in the field of vision at one time.

If the momentary illuminations of the second light source are all very bright then the MRKP method may be used to derive (upon the collection of sufficient sample points and the numbers typically so collected are so sufficient) the rough shoreline of the island of vision, the blind spot, and/or any areas of scotomas causing complete absence of vision. Accordingly, even without any great sophistication, and without any variation in the illumination intensity of the second light source (which can simply be turned on full bright), regions of blindness can be very, very, quickly derived with the MRKP method.

However, the preferred performance of MRKP in accordance with the present invention yields much, much more information than just the shoreline of the island of vision: essentially the preferred method yields the threshold contours of an entire "island of vision" below which contours no point(s) on the patient's actual island of vision fall. The actual heights upon a patient's actual island of vision (the detailed point by point visual sensitivity of the patient) are normally not determined. It is, however, verified that all points on the patient's actual island of vision are above some "shrunken" island of visual sensitivity. The "shrunken" island of vision is completely customized for the individual patient by application of the third preferred method as will be explained. It need not be a subnormal island of visual sensitivity, and can actually be larger than is typical for the patient's age. It is merely a reference island relative to which it is determined that the patient's eye exhibits no significant visual defects by testing all regions of the patient's visual field.

In accordance with the present invention, the manner by which this tight screening for visual defects is obtained is by performing MRKP in a more subtle manner than merely momentarily illuminating the second light source to a fixed, bright, level of intensity. Instead, the intensity of the second light spurce is set at a predetermined variable level of illumination intensity upon each of the times of its momentary illuminations. These predetermined variable levels make the second light source to be within the contour of the "shrunken" island of vision (at its then separation distance and angle from the eye's focus) and therefore visible if the eye's vision is as expected at that location in the visual field. Any failure to detect illuminations of the second light may indicate and/or resultant from depressions, or areas of reduced sensitivity, in the island of vision as well as from scotomas.

The MRKP method thus gives an excellent, and very quickly performed, validation, or threshold test, of visual acuity at the level of a "shrunken" island of vision within the boundaries of the actual island of vision. Every test point obtained is variable in two spatial coordinates and in intensity, and is correspondingly a point that is rich in information. When these information-rich points are obtained quickly, as is the case in the preferred exercise of the MRKP method, then the entire test of the visual field is greatly accelerated with minimal patient fatigue.

6. Modified Reverse Kinetic Perimetry With Successive Approximations to Points Upon the Island of Vision: A Third Preferred Method of the Invention The modified reverse kinetic perimetry (MRKP) method described in the previous section 5. was preferably conducting using knowledge of the contours of a patient's "shrunken" island of visual acuity. The "shrunken" island test standard is not the same for all patients and for all test environments. It is best fully customized for each individual patient and for each individual test environment.

How is this done? How can knowledge of the appropriate size and extent of the "shrunken" island of vision be gained? In accordance with the present invention realization of a fully customized island of vision for each patient is accomplished by performing a third preferred test method called modified reverse kinetic perimetry with successive approximations to points upon the island of vision (MRKP-SA). This third preferred method is preferably performed second in sequence during preferred testing with and by the perimeter. It typically transpires for three (3) iterations at each of four (4) points in the patient's visual field. At the rapid conclusion of applying a modest twelve (12) test stimuli and retrieving the patient detection/non-detection results the patient's "shrunken" island of vision is calculated by the computer.

The third preferred MRKP-SA method commences with strict control of the ambient light intensity of the test environment. In the preferred perimeter enclosure light intensity is adjusted to 31.5 apostilbes. Alternatively, if the perimeter is implemented as a wall-mounted flat screen then the ambient light intensity of the test environment, or room, is quantitatively sensed. A display is presented to aid the test administrator to make a coarse adjustment of ambient lighting such as by means of adjusting a rheostat controlling the intensity of a room light source, by selectively energizing a variable number of discrete room light sources, or by selectively moving or occluding various room light sources. Fine compensation for ambient light level is further realized by the perimeter in accordance with the present invention during its presentation of test stimuli. This will, in accordance with the MRKP-SA method of the invention, make the test stimuli appropriately slightly brighter in an overilluminated test environment and appropriately slightly dimmer in an underilluminated test environment.

The third preferred MRKP-SA method in accordance with the present invention continues by quantitatively measuring (typically) four (4) actual points on the actual island of vision of a particular patient. The points are typically orthogonally aligned, initially at a modest elevation on the anticipated island of vision. The exacting determination of the actual points on the real island of vision transpires by a process of testing somewhat akin to joining threshold perimetry with modified reverse kinetic perimetry (which is itself derived from reverse kinetic perimetry which is, of course, the reverse of kinetic perimetry). Specifically, a "test" light source is first illuminated at a brightness normally above that expected for the local elevation of the island of vision (i,e., suprathreshold) of the corresponding point of the visual field. Normally four points are done at this "overilluminated", or suprathreshold, light stimulus level. Then, contingent upon patient recognitions, the test light source is again illuminated, now at an illumination level below that expected for the elevation of the island of vision of each of the points. Successive illuminations successively approximate the actual intensity sensitivity of the point upon the island of vision. The successive illuminations bracket with ever increasing accuracy the true visual sensitivity of the patient at typically four points (only) on the patient's island of vision.

The four-point height of the individual patient's island of vision typically becomes sufficiently well known (based on patient responses) after three (3) only iterations of variably illuminating each point. A complete, standard contour, "shrunken" island of vision profile is custom calculated in the computer based on the individual patient's demonstrated visual sensitivity as represented by the four sample points.

Testing by the second preferred MRKP method then ensues based on this customized "shrunken" island of vision. This second preferred method testing, when conducted over the nominal eighty (80) points, completely validates that, whatsoever the absolute extent and height of the patient's actual island of vision, significant defects in the nature of scotomas and/or depressions do not exist in this actual island save such defects will be detected.

A sharp reader may wonder why a perimeter that is capable of target intensity control, as well as (indirectly) target positioning, does not simply administer automated standard threshold perimetry. It may be recalled that in standard threshold perimetry the point of fixation remains fixed while the test stimuli increase in intensity. Why incur the complexity of modified reverse kinetic perimetry with successive approximations (MRKP-SA)? One reason is that multiple test stimuli may be simultaneously presented. This is impossible with standard kinetic perimetry. Multiple simultaneous test stimuli shorten the time of testing and reduce patient fatigue.

Another reason involves a small segment of the population exhibiting a particular pathology giving rise to extinction phenomena (wherein the presentation of plural test stimuli is more detectable than the presentation of individual test stimuli). The multiple test stimuli presentations in accordance with the present invention are the only way of testing such population. The extinction phenomenon is a special sign of a parietal lobe lesion and can only be detected if both nasal and temporal fields are examined simultaneously. The MRKP and MRKP-SA methods in accordance with the present invention test both the nasal and temporal fields simultaneously by act of presenting multiple stimuli. Indeed, the testing of the present invention is, for the specific populations exhibiting this pathology, even more sensitive than the testing of the general population. Accordingly, the third preferred MRKP-SA method of the invention is both accurate and reliable across the full range of patient visual islands, and is superior in speed and accuracy to alternative, conventional, methods that the preferred embodiment of a perimeter in accordance with the invention could also perform.

The same sharp reader may next wonder why, if the third preferred MRKP-SA method is so good, reversion is made to the second preferred MRKP method for full field visual screening. One answer is that the second preferred MRKP method is faster, checking each point in the visual field only once instead of three times. Of course, the selection of the appropriate intensity for each point in the visual field for fast testing with the MRKP method is supported by the previous identification of the "shrunken" island of vision using the first-performed MRKP-SA method.

Another answer is that the third preferred MRKP-SA method can always be reentered. Indeed, it may optionally be so entered particularly for the performance of a quantitative test of a large number of points, typically eighty (80), in the visual field. Such an expanded, detail, quantitative testing of the field of vision and exact plotting of a patient's actual island of vision is typically entered if, and when, the more rapid MRKP testing detects a defect in the visual field.

The third preferred MRKP-SA method of visual sensitivity testing at or near the surface of a patient's actual island of vision is fully extendable to performing a detailed local examination of actual local contours (actual visual sensitivity) on the island of vision, and not merely to threshold screening. The third preferred MRKP-SA method will be realized to meld some of the advantages of threshold perimetry in accurately determining the height of points on the island of vision with the power of kinetic perimetry for determining the position of the contours of the island. The power of the third preferred MRKP-SA method should be compared to geophysical mapping wherein both elevation and distance are important to accurate and efficient topographical surveying.

The dynamic methods of the present invention locate, and repeatably relocate, the circles of eccentricity with better than the previously typically 3° to 4° of accuracy. The MRKP-SA method is very powerful for accurately deriving heights, or visual sensitivity, on the island of vision and of defects therein. The topological maps of visual defects obtainable with the preferred apparatus and methods of the present invention are of superior quality.

7. Still Further Perimetry Methods of the Invention

The preferred embodiment perimetry apparatus in accordance with the present invention is fully capable of performing, under software control, standard threshold perimetry.

It is also possible in accordance with the present invention to perform a modified, improved, method of threshold perimetry in evaluation of the entire visual field. It should be recalled that normal threshold perimetry involves (i) fixing a patient's eye on a first light source, while (ii) positioning a second light source to be at different times at various distances of separation and at various angles relative to the first light source, while (iii) recording instances of a patient's visual detection or non-detection of the second light source at the various times during the positioning. This is followed by (iv) plotting the instances of the detections or non-detections versus the distances of separation and the angles in order to derive by the plotting a graphical representation of some portion of the visual field of the patient's eye.

In accordance with the present invention a modified, improved, method of threshold perimetry is accomplished by automatedly positioning with a mechanism (the x-y plotter) that physically moves the first (target) light source relative to the second fixed (stimulus) light source(s) in order to realize the various distances and angles of separation between the two light sources. Moreover, automatedly plotting transpires with this same mechanism that is otherwise and at other times used for the automatedly positioning.

8. Summary Advantages of the Invention

The present invention is directed to realizing diverse benefits. Cost is low. The initial ownership cost of the perimeter apparatus is minimized primarily by utilizing computerized control. Economy is further obtained because a major section of the apparatus—an x-y plotter—is used for the dual purposes of both automated administration of visual field testing and generation of a hardcopy (graphical) representation of test results.

The life cycle cost of apparatus ownership is minimized principally because the perimeter apparatus of the present invention is fully automated and requires no intervention by a skilled perimetrist. Furthermore, the apparatus conducts testing very quickly. A preferred method for optical threshold screening performed by the apparatus reliably and accurately gathers from one to four, and typically two or three, data points about every two seconds. A thorough automated test of threshold visual sensitivity, including production of a graphical hardcopy output, is completed in less than four (4) minutes. Certain limited tests are capable of being conducted in less than thirty (30) seconds.

Accuracy is high. The perimeter apparatus of the present invention is versatile to efficiently and effectively conduct test regimens of diverse types, including wholly new types in accordance with the new methods of the present invention, at any degree of precision required or desired, including at very high precision.

Extraction of data from the test subject is at unprecedentedly high levels. Most points within the field of vision that are extracted by the preferred, interoperative, methods and apparatus of the invention are at or very near to visual threshold sensitivity, and are accordingly very useful and important points bearing much information. These information-rich points are obtained quickly and without the repetitions, retracings, and trial and error retestings that attend previous perimetry methods and equipments.

The preferred methods of visual surveying in accordance with the present invention are entirely automated and are therefore reliably, repeatably, consistently, thoroughly, and economically performed to generate good results. However, in order to get superior results in threshold testing of the visual field at a very high speed, something more than an automated presentation of quality test stimuli, and an automated recovery of patient data in response to such stimuli, is required. The visual field test regimen must grab, and hold the full interest, attention, cooperation and involvement of the patient for the entire duration of testing. This is accomplished in the present invention by inducing the patient's eye to fixate upon a moving light source. The preferred test method of the present invention induces the patient to become actively involved. The patient's interest is piqued and his/her performance is maximized. Meanwhile, any fatigue resultant from an overly long fixation of the patient's eye on an unmoving spot is avoided. By the time that any patient adaptation, malingering, inattentiveness, and/or boredom sets in, the test regimen of threshold visual sensitivity in accordance with the present invention has been completed. Difficulties with (i) the patient's eye becoming tired, (ii) the patient's loss of interest, and (iii) retinal adaption—all such as regularly arise in the conventional prior art methods of optical perimetry including the kinetic method—are substantially eliminated. An eye following a moving light source is believed to be more apt to stay fixated on that moving light source than is a eye required to fixate on a nonmoving source. Additionally, the patient's interest and cooperation is more easily maintained when the examination method, which may last several minutes, is not as boring and monotonous as are the prior art examination methods.

Furthermore, in accordance with all methods of the present invention it is possible to test to the outer limits of the patient's visual field. This visual field normally (in youth) extends 60° superiorly, 75° inferiorly, 60° nasally, and 100° temporally. This visual field is testable in accordance with the present invention despite the presence of the patient's nose, brow and cheek. This expanded latitude of testing is not possible with conventional perimetry of either the kinetic or threshold types wherein the patient fixates straight ahead and where the nose, brow and cheek get in the way of testing parts of the retina. Expanded latitude of testing is enabled in accordance with the present invention because the patient can be forced to look oppositely to where the transient stimulus is applied. That is, the patient's eye is rotated within his/her eye socket relative to his/her brow, nose, and cheek. At certain times a target stimulus will be momentarily illuminated at nasal, superior and inferior points while the reference first light upon which the patient's eye is fixated is respectively at temporal, inferior and superior positions. The required size of the rear-projection screen for a given angle between target and stimulus is also reduced.

It should further be recognized that both preferred perimetry methods of the present invention each entail a reversal of the normal, prior art, kinetic visual field examination wherein a test stimulus is moved into the visual field of a patient's eye that is fixating straight ahead on a reference stimulus. Particularly, in accordance with the present invention the test stimulus is fixed while the reference target stimulus is moved so that it may be followed by the patient's moving eye. The reverse kinetic perimetry (RKP), modified reverse kinetic perimetry (MRKP), and modified reverse kinetic perimetry with successive approximations (MRKP-SA) methods in accordance with the present invention each give an independent check upon results obtained with the conventional method(s). Each method independently supports examination of the entire visual field despite the patient's facial anatomy.

It should further be recognized that still further major variations of ocular testing are possible based on the flexible, programmable, computer-based, perimeter apparatus in accordance with the present invention. Particularly, the perimeter apparatus of the present invention may be driven and employed so that illuminations of the second light source(s) is (are) not momentary, but so that such source(s) remains on while the field of vision of the eye, tracking the moving reference source, gradually overlaps the second source(s). Particularly, a second light test stimulus may be fixed at separate times at respective (i) nasal, (ii) superior, (iii) inferior points. The reference target that is fixated by the patient's eye is then respectively moved (i) from a temporal position whereat the nasal stimulus point is not within the patient's visual field in a nasal direction until the patient's visual field crosses into the nasal stimulus point, (ii) from an inferior position whereat the superior stimulus point is not within the patient's visual field due to the patient's brow in an inferior direction until the patient's visual field crosses into the superior stimulus point, and (iii) from a superior position whereat the inferior stimulus point is not within the patient,'visual field due to the patient's cheek in a superior direction until the patients visual field crosses into the inferior stimulus point. By this procedure, the angular separations of the respective stimulus points and the reference stimulus at each of the respective crossings are known. The crossings of the brightest test stimuli represent the maximum extent of the patient's visual field respectively in the nasal, superior and interior directions. The visual field is determined to its maximum extent, useful in detecting pathological conditions at the periphery of the field, despite interference from the patient's brow, cheek, and/or nose.

BRIEF DESCRIPTIONS OF THE DRAWINGS

These and other attributes and aspects of the present invention will become increasingly clear upon reference to the following drawings and accompanying specification wherein:

FIG. 5a, is a perspective view showing the first embodiment of an ocular perimetry instrument in accordance with the present invention;

FIG. 7 is a schematic block diagram showing the computer, input/output circuits, and peripheral devices that are part of either embodiment of an ocular perimetry instrument in accordance with the present invention;

FIG. 8 is a schematic diagram showing the microstep driver used for x axis and y axis step motor control in either embodiment of an ocular perimetry instrument in accordance with the present invention;

FIG. 9 is a schematic diagram showing the photo detector circuit part of either embodiment of an ocular perimetry instrument in accordance with the present invention;

Figure 11A:
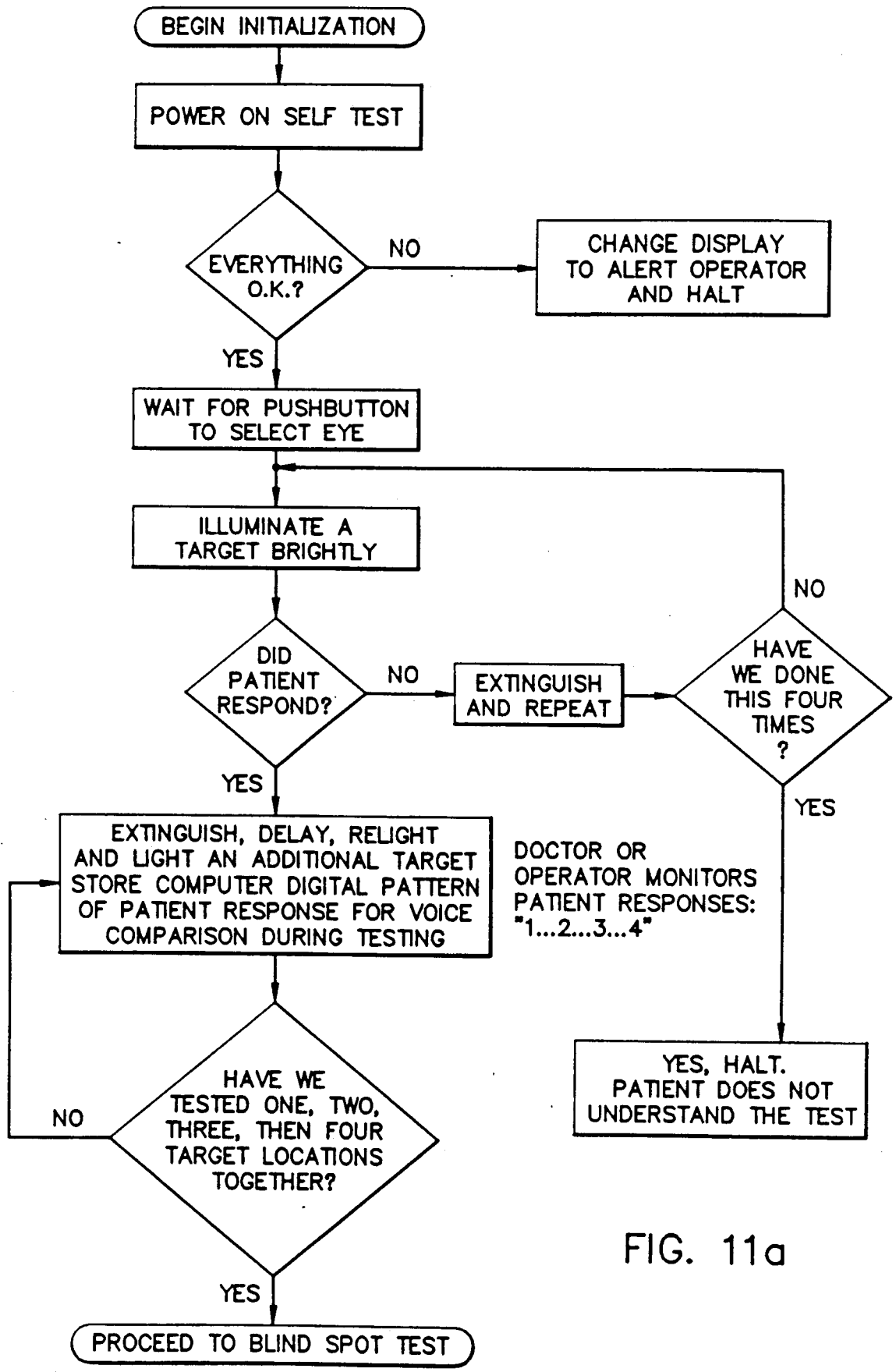
FIG. 11a is a first flowchart showing preferred software executed by the computer of the ocular perimetry instrument for its initialization, and for its training to recognize a voice.
Figure 11B:
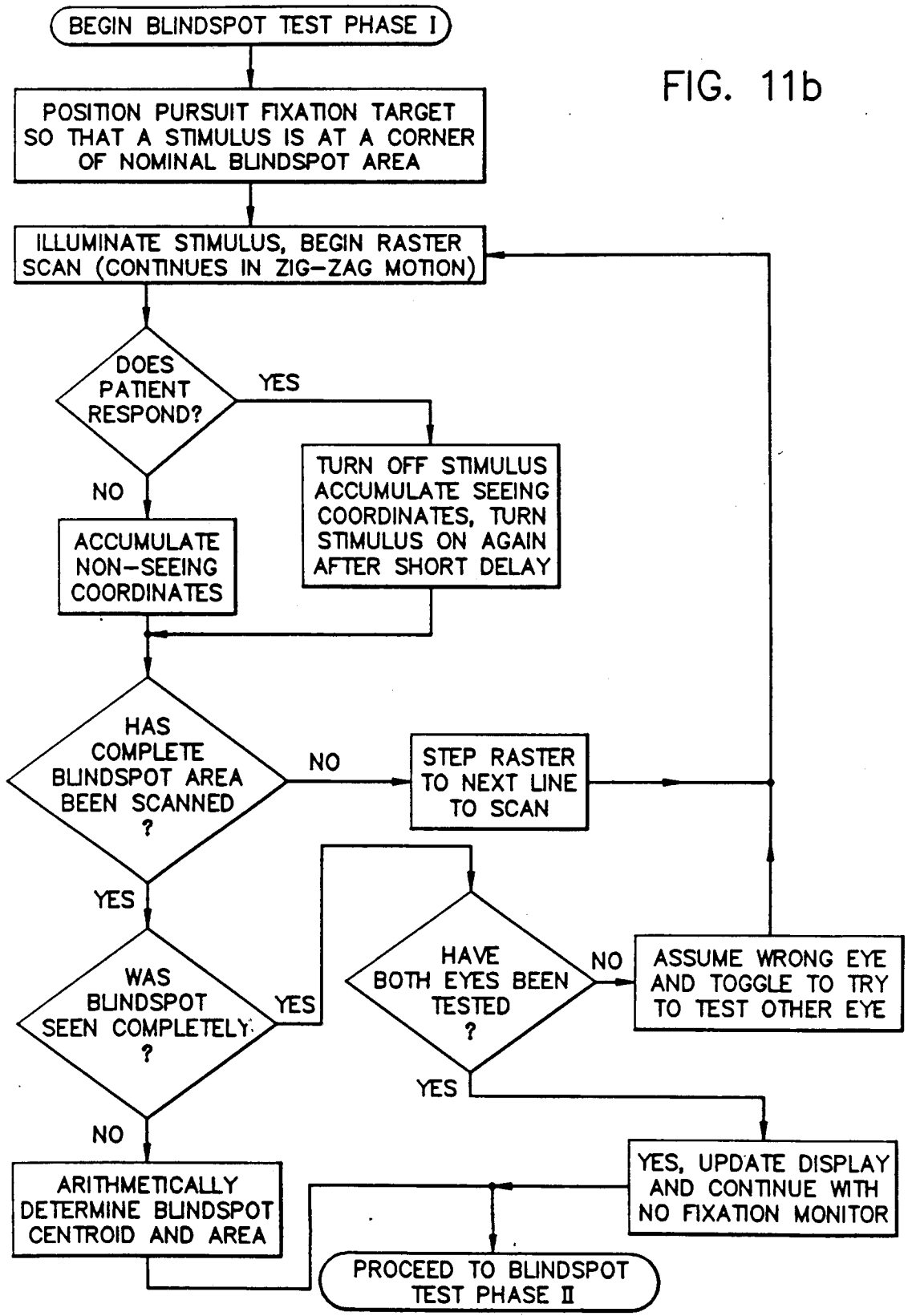
FIG. 11b is a second flowchart showing preferred software for performing a blind spot test phase 1 by the method of reverse kinetic perimetry (RKP), which software is executed by the computer of an ocular perimetry instrument in accordance with the present invention.
Figure 16A:
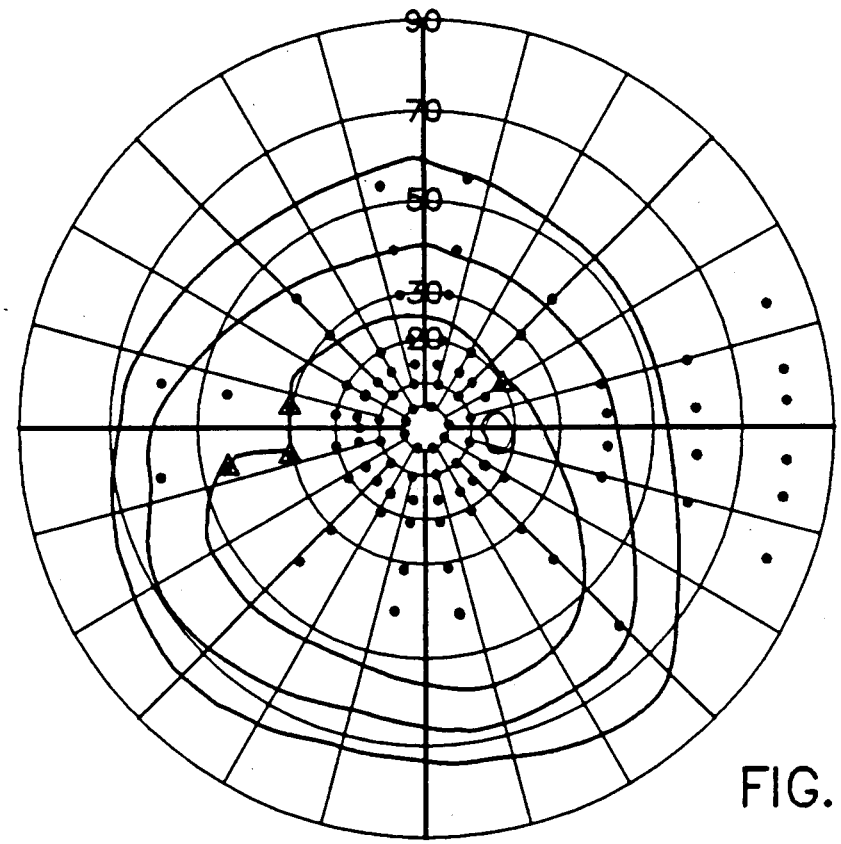
FIG. 16a is a graphical plot showing isopters of the visual field of a right eye, which isopters are derived by testing in accordance with the present invention, which isopters indicate a pathological condition in the eye's visual field.
Figure 16B:
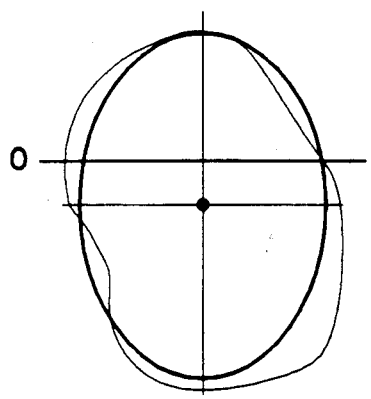
Figure 16C:
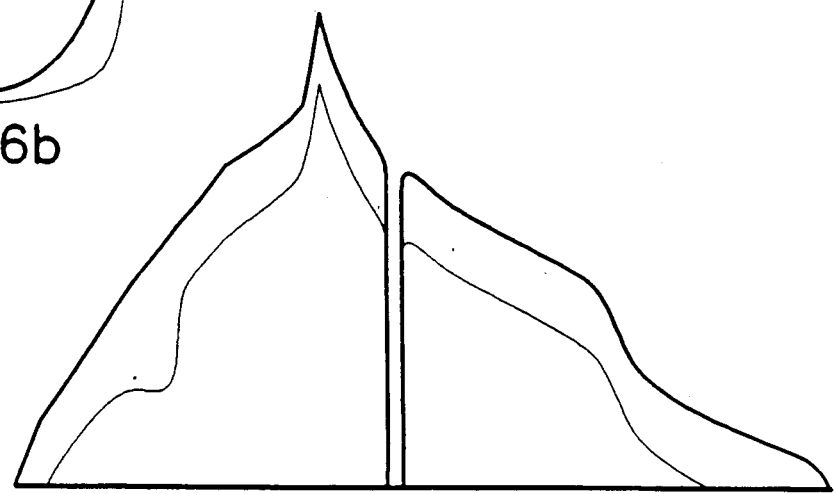

FIG. 16b is a graphical plot of the blind of an actual patient's eye superimposed over a normal standard blind spot, the contours of the actual blind spot having been derived by RKP testing in accordance with FIG. 11b; and FIG. 16c is a graphical plot of a computed cross-sectional profile through the island of vision along on East to West axis through the blind spot of that actual visual field graphed in FIG. 16a superimposed upon a normal cross-section of an island of vision scaled to the same overall visual sensitivity, the actual cross-sectional profile showing a pathological condition in the eye's visual field. This actual profile having been derived by either MRKP testing in accordance with FIGS. 11*f*, 11*g* or, more exactingly, MRKP-SA testing in accordance with FIGS. 11*h*, 11*i*.

DESCRIPTION OF THE PREFERRED EMBODIMENT

1. Surveying the Visual Field

Figure 1:
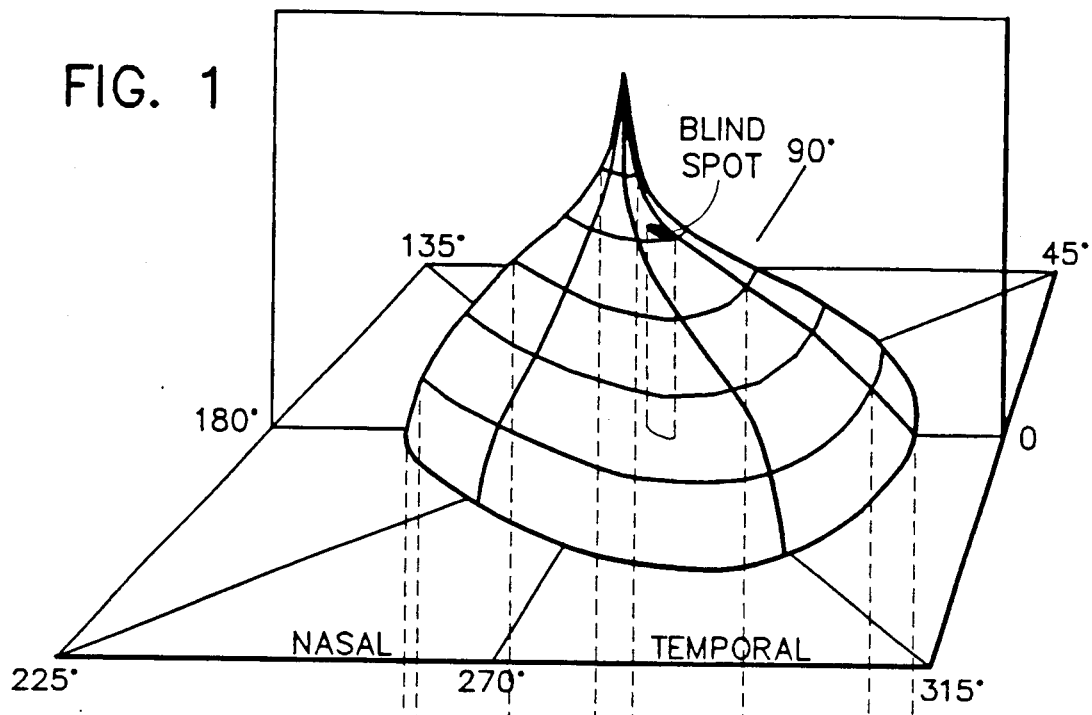
FIG. 1 is a three-dimensional representation of the island, or hill, of vision representing the sight in the right human eye.

The present invention is directed to surveying the visual field of the human eye. The standard representation of the human visual field is shown in FIG. 1. An island, or hill, of vision rises out of a flat plane, or sea, of blindness. Points on the island and sea are at various angles and distances from a central point that is the eye's fixation point. The plane, or sea, represents points to which the eye is insensitive. The island, or hill, exhibits a tall, narrow, peak at its center. This peak is the point of visual fixation, and highest acuity and visual sensitivity. This peak represents the fovea, or that retinal area of greatest resolving power and sensitivity to visual stimuli. The retinal sensitivity of this area is about 1 to 0.1 apostilbes. The shoreline of the island of vision has a retinal sensitivity of about $10^4$ apostilbes. The vertical, or height, scale is logarithmic. The dynamic range of contrast sensitivity of the eye is approximately $10^4$. This great range presents a challenge to accurate measurement of the visual field throughout the entire range.

The height of the island, or hill, represents the contrast sensitivity of the eye. The contrast sensitivity diminishes with distance from the peak, corresponding to diminishment in the sensitivity of the extra-foveal retina. The breadth of island is a measure of the extent of vision. Beyond the edges, or shoreline, of the island of vision there is no sight because there are no retinal receptors (rods or cones) within the eye.

The island of vision is not symmetric in slope or extent. Altitude, corresponding to contrast sensitivity, is lost rapidly on the nasal side. The landscape has a more general, prolonged slope on the temporal side. At a position about 15° temporal to fixation, a deep well with parallel vertical sides plunges from the island surface down to the plane, or sea, level of non-visibility. This well represents the physiologic blind spot, a "window" through which the retinal nerve fiber layer exits the eye at the optic nerve head. In this area, approximately 6° horizontally by 9° vertically in extent, there are no retinal receptors and no vision. Every point on the landscape on the island or of vision, or the visual field, corresponds to a point on the retina.

Figure 2:
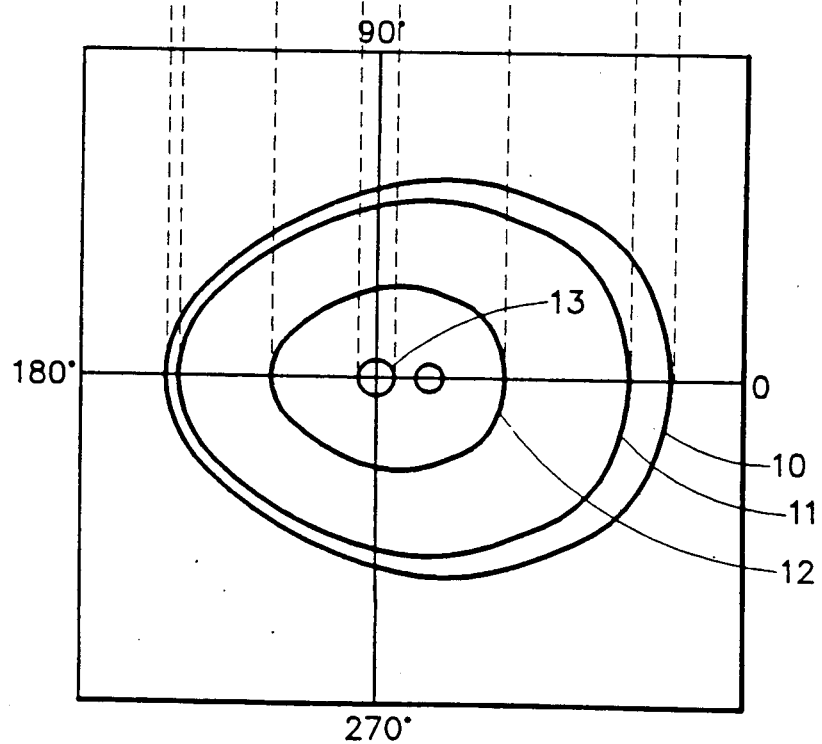
FIG. 2 is a graphical representation of a normal circular static field of the retinal sensitivity of the human eye plotted in isopter contour lines.

The visual field examination is equivalent to a search for contour irregularities in the island of vision landscape. Of the three major previous methods used to survey and map the visual field—the kinetic, static threshold and static suprathreshold methods—the preferred methods of the present invention are most analogous to the kinetic method. A graphical representation of the results of a survey by the kinetic method is shown in FIG. 2. The method of the present invention produces an identical representation (amongst other representations).

In the testing of visual fields by the previous kinetic method, a light of fixed stimulus characteristics, representing a constant altitude on the island of vision, is moved into the visual field until it is first detected by the patient. Because the test stimulus changes position, this stimulus presentation is called kinetic (moving). The stimulus is successively advanced toward the center of the visual field from a position of nonvisibility to a position of visibility, each advance being from a different direction relative to the center of the field. As the stimulus is advanced in each direction a visual threshold is mapped for a stimulus of that particular fixed characteristics (intensity and size) at the particular direction from which the target is advanced.

The joining of threshold points for a stimulus of a particular illumination level forms a line of equal contrast sensitivity called an isopter. The kinetic method is equivalent to mapping a series of horizontal slices through the island of vision. Four isopters 10-13, obtained by moving a corresponding four stimuli that are each of a different stimulus characteristic into the island of vision, are illustrated in FIG. 2. The isopter 10 is the boundary, or shoreline, of the island of vision. It is the boundary beyond which no stimulus, no matter how great its luminance or size, may be detected. Efficient and effective optical threshold perimetry in determination of this threshold isopter 10 is one concern of the apparatus and methods in accordance with the present invention.

Figure 3:
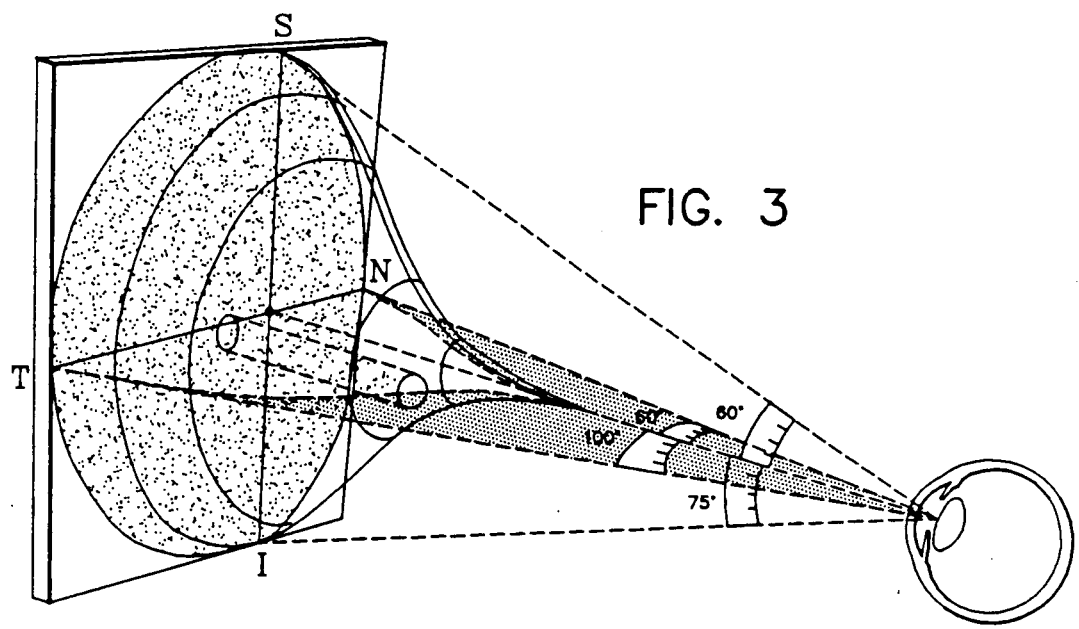
FIG. 3 is a diagrammatic representation showing the island, or hill, of vision in relation to the left eye.

The present invention is, however, generally applicable to the surveying of the entire visual field in order to generate and present many isopters which will have identical appearance and significance to those shown in FIG. 2. The extent of the island of vision is illustrated diagrammatically in FIG. 3. The shoreline limits of the island, or boundaries of the visual field, typically extend from fixation 60° superiorly (S), 60° nasally (N), 75° inferiorly (I), and 100° temporally (T) in youth. These limits are determined by the location and distribution of the retinal receptor cells. No adjustment of the head or eye position can extend the range of the visual field beyond these points. However, three of these innate limits of the visual field are not accessible by an eye which is fixating straight ahead. Particularly, the brow extends into the superior, the nose extends into the nasal, and the cheek extends into the inferior regions of the visual field. This may be easily verified for oneself by staring straight ahead and noting that one's own facial features appear at the far periphery of one's visual field in all directions save the temporal.

Previous methods of surveying the visual field, whether kinetic or static, require that the eye should be fixated straight ahead. This means that the ultimate limits of the actual visual field threshold may not be fully assessed in the superior, nasal, and inferior directions. This failure to examine the visual field at the full extent thereof is detrimental because certain deteriorations of the retina may start at the far peripheral boundaries thereof. Correspondingly, a thorough visual field examination should examine the absolute visual field thresholds of the eye even though it is not convenient to do so with previous test methodology and apparatus.

Figure 4:
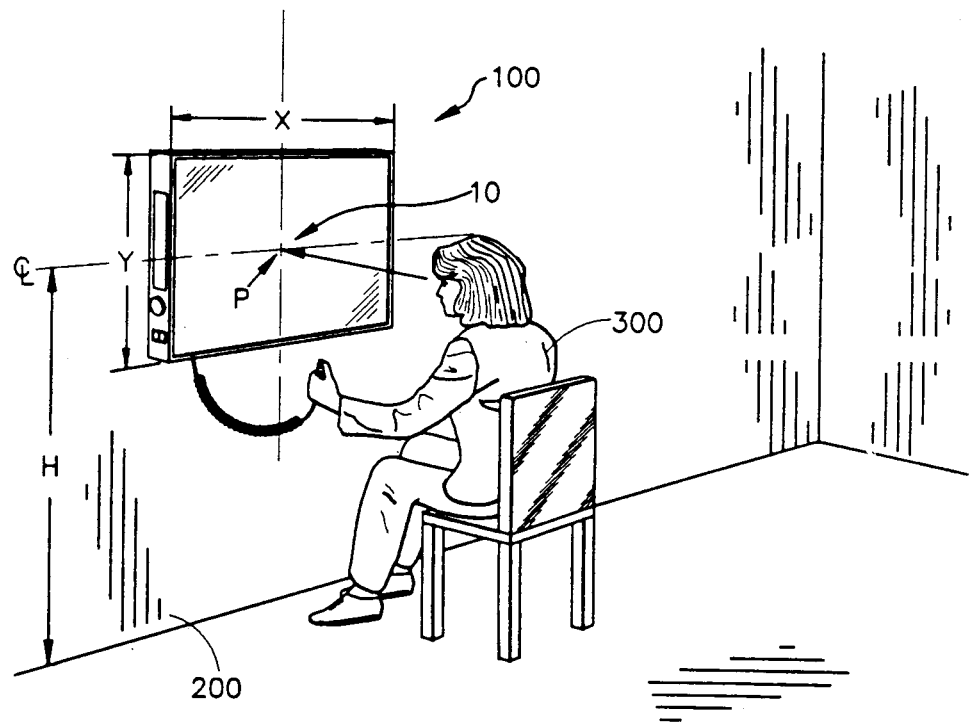
FIG. 4 is a pictorial diagram showing the surveying of a visual field of a patient's eye in accordance with the present invention using a first embodiment of an ocular perimetry instrument in accordance with the present invention.

2. The Preferred Embodiment of an Ocular Perimetry Instrument in Accordance With the Invention A diagrammatic representation of a first embodiment of an ocular perimetry instrument, or perimeter 100, is shown in its operational environment in FIG. 4. The perimeter 100 is a flat field device of dimension X equaling approximately 32 inches and dimension Y equaling approximately 28 inches. It is mounted upon a wall 200 with its center at height H equaling approximately 48 inches. The perimeter 100 is approximately 3 inches in thickness. Its front is a planar rear-projection screen, normally a sheet of translucent plastic serving as a rear-projection screen for various light emitting diode (LED) light sources which are fixed to the rear side of the translucent front of the perimeter 100. The embodiment of the perimeter 100 shown in FIG. 4 is normally viewed in a controlled illumination room by a patient 300 positioned in front of the screen at a distance D that normally equals approximately 14.2 inches. Other distances D could be defined in terms of the angles subtended threat. The patient is located with his/her eye to be tested roughly opposite the center of the screen.

Generally, the size of the perimeter 100 relative to the separation D from the patient's eye is not so great that the screen will extend from a central point P of fixation so far as an angle of 60° in the nasal direction, nor so far as 100° in the temporal direction (or a total of 160° horizontally). Neither will the perimeter 100 subtend an angle at the eye of patient 300 which extends either so far as 60° superiorly, or 75° inferiorly (or a total of 135° in the vertical direction). The screen 100 will, however, subtend angles at the eye of patient 300 at a distance D therefrom which angles exceed a total angular extent of 75° in the vertical direction and an angular extent of 100° in the temporal direction. In fact, the actual useful angles subtended by perimeter 100 will be approximately +60° (120° total) in the vertical direction and nearly +90° (180° total) in the horizontal direction at the eye of patient 300.

When, as will become evident during further discussion of the present invention, the patient's eye is allowed to fixate at the various margins (the top, bottom, left edge and right edge) of perimeter 100, then the angles subtended by the surface of perimeter 100 at the eye of patient 300 will be more than adequate to permit that introduction of illuminated objects at the opposite margins of the perimeter 100 will discern the absolute limits of the visual field of patient 300. The capability of the preferred embodiment of a perimeter 100 in accordance with the present invention to alter the patient's fixation point permits that the dimensions of a perimeter so performing should be smaller and/or the distance D should be greater than otherwise would be required. This capability saves on the size and expense of the perimeter, the required area of wall space required in the physician's office, and the required size of the room within which the visual field examination is conducted.

A detailed perspective view of that embodiment of a perimeter 100 in accordance with the present invention previously seen in FIG. 4 is shown in FIG. 5a. The perimeter is housed in a case 110 that mounts a rear projection screen 120 at its front surface. An alphanumeric display area 130 normally occupies a region at a one side, nominally the left side, of the rear projection screen 120. Appropriate operator messages involved with selection and administration of the test regimen are displayed in this area. For example, the display 130 variously displays (i) encoded-scale background illumination level, (ii) error conditions occurring during the conduct of testing, and (iii) the sequence of test events for observation by the test administrator (and possible response thereto, although such response is not normally required). The display of such messages is controlled by a computer (to be shown in FIG. 6). The test selection and test control inputs by the operator in response to such messages are made through operator control 140, normally a simple knob controlling two single-pole single throw (SPST) switches.

Figure 14:
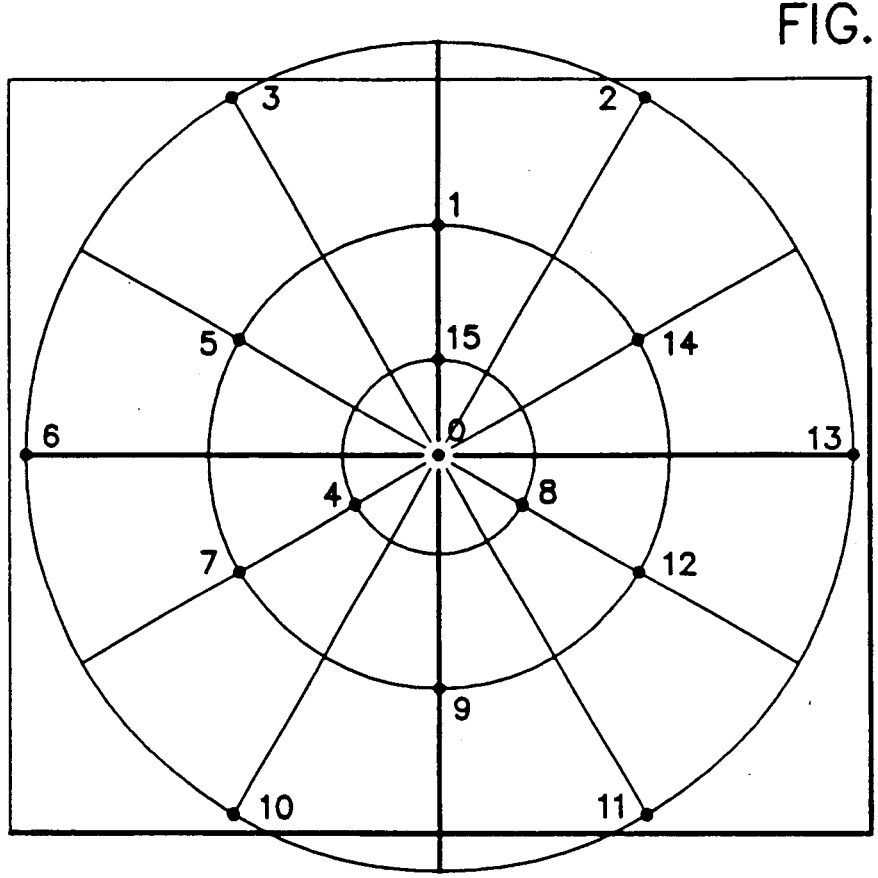
FIG. 14 is a diagrammatic representation of the angles and separations of the sixteen fixed target stimuli that are normally momentarily illuminated relative to a moving fixation stimuli (not shown)

Also displayed on rear projection screen 120 at various times are one or more stimulus light sources. The stimulus light sources are preferably implemented by light emitting diodes (LEDs) 150 located at fixed locations. There are normally sixteen such LEDs located in the indicated pattern. This pattern, and the arbitrary numbering of the sixteen LEDs as numbers 0 through 15, is again shown in FIG. 14.

A reference, fixation, light source 160, normally another single LED, but potentially a small cluster of LED's, is controllably moved to become positioned anywhere within the entire field of rear projection screen 120. The reference LED 160 is shown at an arbitrary position in FIG. 5a. Not all of the fixed stimulus LEDs 150 and the moving fixation target reference LED 160 will be simultaneously illuminated.

A patient response push button 170 is connected to the perimeter 100 by cord 171. A microphone 520 mounted in case 110 permits reception of the patient's voiced responses. The push button 170, and the microphone 520, are the alternative means by which the patient 300 (shown in FIG. 4) makes known his/her observations upon the momentary illuminations of the stimulus light sources 150.

A plotter paper tray 180 is capable of holding one or more sheets of plotter paper. The tray may be slid in and out from perimeter 100 in order that paper upon which visual field plots have been generated may be extracted for study and reference, and in order that additional unrecorded sheets of plotter paper may be installed as required.

Figure 5B:
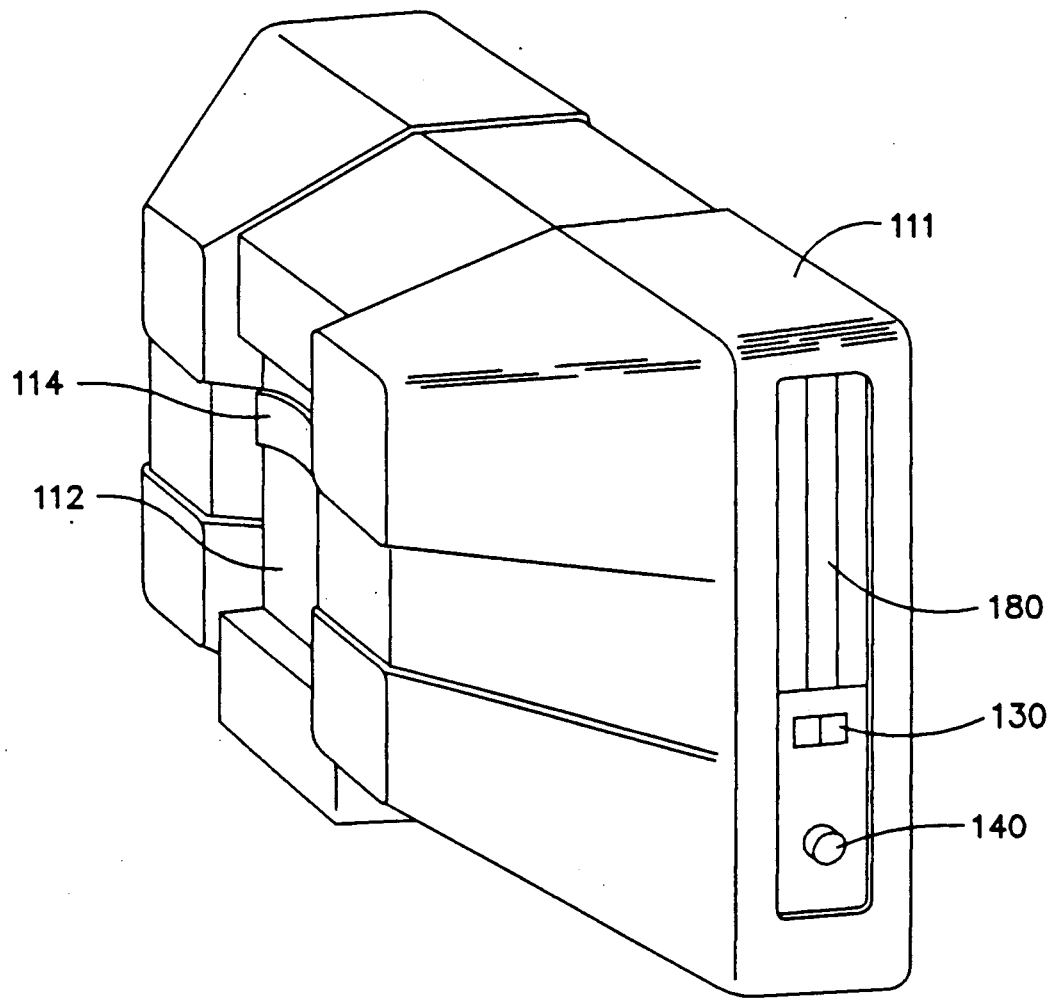
FIG. 5b is a perspective view showing a second embodiment of an ocular perimetry instrument in accordance with the present invention.

A second, preferred, embodiment of perimeter 100 is shown in FIG. 5b. The case 110 of the embodiment shown in FIG. 5a is simply expanded as case 111 in order to enclose the area between the screen 120 (not shown in FIG. 5b for being inside case 111) and the opening 112 through which the patient observes the screen 120. The enclosing case 111 permits precise control of the ambient illumination level during visual field testing, and the precise positioning and positional maintenance of the patient's head on forehead rest 114.

The size of aperture 112, the considerable volume of case 111 which is approximately 32" width × 28" height × 18" depth, and the low ambient illumination within case 111, permit in combination that almost all patients can use the perimeter 100 without experiencing claustrophobia or being unduly distracted by the physical environment of the perimeter and the circumstances of its use. Indeed, the perimeter 100 functions in certain test methods (to be explained) entirely differently than a bowl perimeter which, in the encased embodiment of FIG. 5b, it somewhat resembles. With a bowl perimeter the patient must be laboriously positioned and instructed.

The perimeter 100 requires neither extreme precision in the placement of the patient's head (not shown) at opening 112 nor in the instruction of the patient. The perimeter 100 may actually commence preliminary modified reverse kinetic perimetry with successive approximations (MRKP-SA) testing as sort of an "attract" mode similar to an arcade video game. The test cycles until it gets valid data. A patient may actually be enticed to look through aperture 112, to naturally start tracking the moving fixation light source 160 (shown in FIG. 5a), and to either press the pushbutton 170 (shown in FIG. 5a) or announce a number "one" through "four" (as instructed) with negligible, or even no, prompting or instruction.

The perimeter ergometrics and test regimens in accordance with the present invention should be appreciated during the ensuing discussion to be sufficiently well integrated and automated so that there is a finite chance that a patient receiving cursory instruction and placed alone in a room with the perimeter 100 will successfully administer himself/herself a comprehensive test of visual sensitivity. Complex testing of a complex physiological function with this degree of "slickness" is unprecedented, and makes the present invention an exemplary model of patient-friendly physiological test apparatus and test regimen design.

Figure 6:
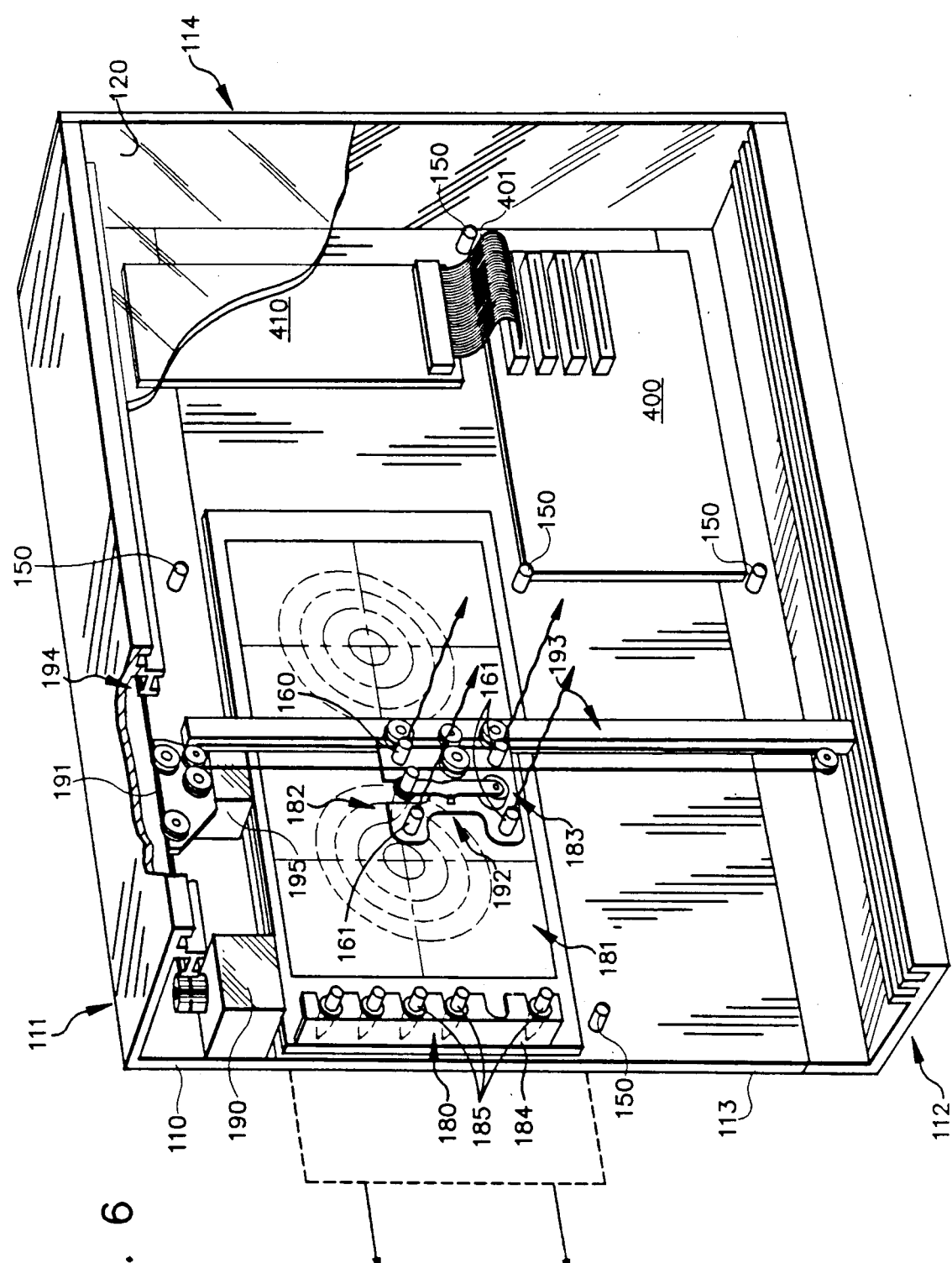
FIG. 6 is a cut-away perspective view showing the interior of the first or the second embodiment of an ocular perimetry instrument in accordance with the present invention.

A cut-away perspective view of the preferred embodiment of a perimeter 100 in accordance with the present invention is shown in FIG. 6. The case 110 includes an upper extrusion 111, and a lower extrusion 112. Both extrusions are of custom contour and are normally extruded from aluminum. The required contours of such extrusions permit, in addition to the necessary fitting of the back panel 113 and the rear projection screen 120, that the extrusions may mount (i) the x-axis rail 194 (which carries the x-axis carriage 191), and (ii) the other end of the y-axis rail 193 to that end which is borne by the x-axis carriage 191. This is simply to say that the case 110, and the extrusions 111 and 112 thereof, support, without modification, a conventional mechanical x-y plotter mechanism for free movement within the confines of the case. The case 110 also fits right and left end caps 114, which may be removed for maintenance.

The stimulus light sources, or LEDs, 150 may alternatively be fixed in position to case 110 instead of to the back side of screen 120. If the target light sources 150 are so alternatively affixed, then a typical five of the normal sixteen of these LEDs 150 area located as shown in FIG. 6. Regardless of whether the LEDs 150 are affixed to case 110 or, as is normal, to the back of screen 120, the reference light source, or LED, 160, moves relative to each of case 110, screen 120, and fixed LEDs 150.

Normally only a single LED 160 is used as the fixation target. However, in the eye of some individuals there exists a blind spot substantially at the fixation point, meaning at the fovea, of the field of vision. In order for affected eye of such an individual to fixate upon any reference point, either moving or stationary, such reference "point" must be spatially extended. Accordingly, three additional LEDs 161, along with LED 160, are all illuminated as a moving reference, spatially extended, target light source for those certain individuals whose eye has a blind spot at or near the fovea that precludes the fixating of a single point light source. The individual having such macular degeneration is instructed to look toward the black center of target light sources 160, 161 and to follow their collective movement with his/her eye so that all four sources remain visible.

The reference target LED 160 is affixed to a y-axis carriage 192. The y-axis carriage 192 is controllably moveable in y-axis position upon y-axis rail 193 by y-motor 195 acting via a cable and capstan drive system. The y-motor 195, the y-axis rail 193, and the y-axis carriage 192 are entirely borne upon x-axis carriage 191. This x-axis carriage 191 is moveable in x-axis position along x-axis rail 194 under control of x-motor 190 in similar fashion to that of the y drive system. The normal and conventional carriage mechanism of an x-y plotter will be recognized.

The moveable y-axis carriage 192 also mounts, oppositely to reference LED 160, a releasably held marker pen 182. This pen may be selectively lowered by action of pen lift solenoid 183 into contact with graph, or chart, paper 181 which is carried upon the sliding paper plotter tray 180. Additional pens 185 of different colors may be picked up from pen reservoir 184 and individually selectively substituted for pen 182. At some time after completion of the examination of the visual field, and after computation in computer 400 of the parameters of the visual field resultant from such examination, the calculated parameters of the visual field are automatically plotted onto graph, or chart paper, 181 (normally 11" by 17"). The plotting is in a conventional form that is interpretable by an ophthalmologist. The plotting is preferably done in multiple colors for ease of interpretation.

The exercise of the preferred embodiment of a perimeter 100 in order to perform visual field testing in accordance with the present invention is by computer 400 operating under programmed control. The computer 400 is normally the motherboard of a personal computer, normally of the XT type available from IBM Corporation and other suppliers. At one of the expansion slots normally available on the motherboard of computer 400 a custom electronics assembly, or I/0 board, 410 is connected by ribbon cable 401. The communication to and from computer 400, and the control program resident therein, transpires through this I/0 board 400. The functions implemented on the I/0 board 400 are substantially conventional, and could be substantially derived in standard communications boards available from diverse manufacturers, with the exception of the microstepper function to be shown in FIG. 8. The functions are preferably implemented in a customized I/0 board 410 in order to save space, weight, and cost. The I/0 board 410 will be understood to exhibit wired electrical interconnections (not shown) directed to both receiving information from (e.g., from the push button switch 170), or to directing control to (e.g., to the x-motor 190 and the y-motor 195), other elements within the perimeter 100.

3. Electrical Construction Details of the Ocular Perimetry Instrument in Accordance with the Invention An electrical schematic block diagram of the control section of either embodiment of an optical perimetry instrument, or perimeter 100 in accordance with the present invention is shown in FIG. 7. Instrument control is implemented by a PERSONAL COMPUTER MOTHERBOARD 400, including a software program which is normally fixed in unerasable memory such as PROMS or otherwise (not shown). Both the PERSONAL COMPUTER MOTHERBOARD 400 and the I/0 BOARD 410 are supplied with direct current, D/C, power from POWER SUPPLY 500. The POWER SUPPLY 500 receives normal 110 V.A.C. power via a plug. Power on/off switches (not shown) for the POWER SUPPLY 500 and for the perimeter 100 are employed for power control. The PERSONAL COMPUTER MOTHERBOARD 400 communicates with the I/0 BOARD 410 via ribbon cable 401 (previously seen in FIG. 6) for receiving operator initiation and control of testing, for controlling in an automated manner the testing operations of perimeter 100, and for receiving the patient's responses to the test sequence.

In the idle condition, ready for control inputs, the program residing in the memory of, and running within, the PERSONAL COMPUTER MOTHERBOARD 400 will cause the DISPLAY LED DRIVERS 411 within the I/0 BOARD 410 to display messages within the area of DISPLAY 130 (previously seen in FIG. 5). These lighted messages within the area of DISPLAY 130 will solicit that the operator should initiate a test sequence by selecting one or more quantities with OPERATOR INPUT CONTROL KNOB 140. This knob preferably controls two ganged single pole single throw (SPST) switches. The switch closings are detected at OPERATOR CONTROL CIRCUIT 412 on the I/0 BOARD 410. They are appropriately debounced and level transformed in order that they may be read through the data bus of PERSONAL COMPUTER MOTHERBOARD 400. Responsive to selections by the OPERATOR INPUT CONTROL KNOB 140, the program within the PERSONAL COMPUTER MOTHER BOARD 400 will cause the appropriate changing of DISPLAY 130 by selectively enabling the DISPLAY LED DRIVERS 411, which are also upon the data bus of the computer.

At such time as automated testing of the visual field by the perimeter 100 has been selected, the PERSONAL COMPUTER MOTHERBOARD 400 will interrogate via the LIGHT SENSOR CONDITIONING CIRCUIT AND A/D CONVERTER 413 (i) the background light intensity via BACKGROUND SENSOR 420, (ii) the position of the x/y carriage via X, Y HOME SENSORS 421, and (iii) the on condition of the illuminated FIXATION TARGET LED(s) 160 via the TARGET LED SENSOR ON 422. In accordance with the sensed conditions, the computer will adjust the intensity of all light sources and position the carriage of the x/y plotter mechanism.

If the perimeter 100 is enclosed within the case 110 shown in FIGS. 4 and 5a then the computer will indicate the background light illumination condition in display 130. The test administrator should adjust ambient illumination in accordance with the display 130, which is continuous and continuously updated by the PERSONAL COMPUTER MOTHERBOARD 400 in accordance with sensed background light intensity. At such time as the test administrator has adjusted ambient light to be approximately 31.5 apostilbes another selection with OPERATOR INPUT CONTROL KNOB 140 will cause PERSONAL COMPUTER MOTHERBOARD 400 to commence to conducting the selected automated test procedure.

If the perimeter 100 is alternatively cased in the preferred embodiment of case 111 shown in FIG. 5b the PERSONAL COMPUTER MOTHERBOARD 400 will act through AMBIENT LIGHT CONTROL 600, essentially a digital-to-analog converter with an amplified power output signal, to control VARIABLE INTENSITY LIGHT 610. The VARIABLE INTENSITY LIGHT 610, and the BACKGROUND SENSOR 420 that responds to such LIGHT 610, are both within the interior of case 111 (shown in FIG. 5b). The internal illumination level within case 111 is automatically set to approximately 31.5 apostilbes.

During the conduct of testing the PERSONAL COMPUTER MOTHERBOARD 400 will cause the X-AXIS MICROSTEP CIRCUIT 414 and the Y-AXIS MICRO-STEP CIRCUIT 415 to respectively drive the X-MOTOR 190 and the Y-MOTOR 195 so as to move the FIXATION TARGET LED(s) 160, upon which the patient focuses, within the field of the rear projection screen 120 (shown in FIG. 5a). The FIXATION TARGET LED(s) includes both LED 160 and LEDs 161 previously seen in FIG. 6. The intensity of the FIXATION TARGET LED 160 will be adjusted under computer control through the FIXATION LED INTENSITY CIRCUIT 416. If there were to be any change in the background light (which is detected by BACKGROUND LIGHT SENSOR 420 which is continuously interrogated through LIGHT SENSOR CONDITIONING CIRCUIT AND A/D CONVERTER 413), and/or the test regimen(s) was (were) to require a variation in the ambient light intensity or any selective illumination of the FIXATION TARGET LED(s) 160, then intensity variation may be accomplished under programmed control (within case 111).

The programmed control of PERSONAL COMPUTER MOTHERBOARD 400 also acts (i) through the FIXATION LED INTENSITY CKT 416 to vary the intensity of FIXATION TARGET LED(s) 160, and (ii) through the STIMULUS LED INTENSITY CKTS (16 EA) 419 to selectively vary the intensity (including "on" and "off") of individual STIMULUS LEDS 150.

During the course of testing the PERSONAL COMPUTER MOTHERBOARD 400 causes the STIMULUS LED INTENSITY CIRCUITS (16 EA) 419 to selectively illuminate ones of the STIMULUS LEDS 150. At the times of such selective illuminations the computer has knowledge of the position of FIXATION TARGET LED(s) 160, and the intensity of this (these) LED(s), by action of the control which it has previously effected through X-AXIS MICROSTEP CIRCUIT 414, Y-AXIS MICROSTEP CIRCUIT 415, and FIXATION LED INTENSITY CIRCUIT 416. At the times of these selective illuminations, the computer accumulates data regarding the patient response(s) either as (i) registered by the PATIENT RESPONSE PUSH BUTTON 170 and as communicated through cable 171 (shown in FIG. 5) to PATIENT RESPONSE BUTTON CONDITIONING CIRCUIT 417, or else preferably as (ii) registered by spoken voice input to MICROPHONE 500 that is processed in SPEECH RECOGNITION AND SYNTHESIS CKT 418. If no patient response is received after an appropriate time at a particular position of the FIXATION TARGET LED(s) 160 and upon associated illuminations of ones of the STIMULUS LEDS 150, then the computer will assume that the patient has not seen any of the illuminations and the data recorded will so indicate.

It should be recognized that the binary signal produced by a PATIENT RESPONSE PUSH BUTTON 170 is not the only type of patient data input that might be made by mechanical, non voice, means to the perimeter 100 in accordance with the present invention. Particularly, the patient could be given a multiple position switch. The patient would indicate by positioning of a rotary knob or the like whether he/she has recognized nothing (the normal, home, default position), or has variously seen one, two, or three, or even four light sources upon a single illumination event. Multiple position switches are, however, believed to be (i) cumbersome, (ii) difficult for the patient to understand and learn, (iii) distracting to the patient who may attempt to look at the switch instead of the presented test stimuli, and (iv) difficult to reliably position in the dark.

Consequently, enhanced and sophisticated means for recovering data from the patient, and providing directions to the patient both before and during the test, are provided in accordance with the preferred embodiment of the perimeter 100 in accordance with the present invention. This sophisticated approach is based on the SPEECH RECOGNITION AND SYNTHESIS CIRCUIT 418. This speech recognition circuit, currently available as plug-in printed circuit board for a personal computers, permits a limited number of words such as "1", "2", ..."4" that are typically spoken by a variety of patie be reliably recognized. These words are received in MICROPHONE 520 and decoded into digital representations recognizable by the computer.

The computer may optionally direct the provisioning of oral messages to the patient through the same SPEECH RECOGNITION AND SYNTHESIS CIRCUIT 418, this time driving the SPEAKER 510. The incorporation of the speech recognition and/or synthesis capability is not incompatible with the simultaneous and parallel incorporation of the PATIENT RESPONSE PUSH BUTTON 170. Rather, oral input and/or output is realized within and by the perimeter 100 as features that are well accepted by, and efficiently operable with, most non-mute hearing patients. The speech recognition and/or speech synthesis features are particularly beneficial in perimeters that are in intensive use for conducting visual field examination on a great number of patients, such as inductees into the armed forces After the completion of the administration of a test sequence, the computer is capable of, under program control, filtering the test data and repeating any portions of the test sequence for which results appear inconsistent or irrational. The computer subsequently displays (as will be next discussed) the data obtained both during initial test, and during any retests. The data displays indicate to a trained ophthalmologist observer whether malingering, subterfuge, or a true pathological condition has been uncovered during the testing. In certain more sophisticated, optional, configurations the computer is capable of accepting further audio inputs from the test subject and/or the test administrator indicating "go back" or "go slower" or "go faster". The computer responds to these inputs by adjusting the sequencing, resequencing, and/or rapidity of testing within predetermined parameters.

A detailed schematic diagram of one of the microstep circuits, for example X-AXIS MICROSTEP CIRCUIT 414 (previously seen in FIG. 7) is shown in FIG. 8. The PERSONAL COMPUTER MOTHERBOARD 400 (shown in FIG. 7) sets, via its data bus which is carried on interconnection cable 401, the DIRECTION (CW/CCW) (either clockwise or counterclockwise) that a RECIRCULATING 16 STEP SHIFT REGISTER 430 will count. The computer also sets via the bus a # OF MICROSTEPS into PROGRAMMABLE COUNTER 431, and also a MICROSTEP RATE into PROGRAMMABLE CLOCK 432. The PROGRAMMABLE CLOCK 432 will produce pulses at a programmable rate into the PROGRAMMABLE COUNTER 431. The PROGRAMMABLE COUNTER 431 in turn passes a predetermined # OF MICROSTEPS at a MICROSTEP PERIOD representing that rate to the RECIRCULATING 16 STEP SHIFT REGISTER 430. The sixteen data output bits Q1-Q16 of the RECIRCULATING 16 STEP SHIFT REGISTER 430 are respectively received into sixteen resistive dividers consisting of resisters of R1-R16 (connecting to INVERTING VOLTAGE TO CURRENT CONVERTER 433) respectively connecting to resistors R20-R36 (connecting to INVERTING VOLTAGE TO CURRENT CONVERTER 434). The individual values of resistors R1-R16 equal the values of resistors R36-R20 respectively. Both sets of resisters R1-R16 and R20-R36, and the voltage dividers so formed, are chosen to produce a linear step motion of the driven motor upon each microstep. These linear step motion signals developed are approximately sine and cosine voltage signals. This is illustrated wherein the "SINE" signal, developed by stepwise increments of voltage provided from the Q1-Q16 outputs of the RECIRCULATING 16 STEP SHIFT REGISTER 430, is received at VOLTAGE TO CURRENT CONVERTER 434. Likewise, the same Q1-Q16 signal outputs are channeled through the other resistive divider leg of the 16 voltage dividers to cumulatively form stepwise signal "COSINE" which is received at INVERTING VOLTAGE TO CURRENT CONVERTER 433.

The current signal output from VOLTAGE TO CURRENT CONVERTER 433 is representative of the sine function, and is received at the first windings of X MOTOR 190, which is of a step motor type. The current output of inverting voltage to current converter 433 is likewise received at the other, orthogonal, windings of X MOTOR 190. The combination of the applied sine and cosine signals position the x step motor at a particular angular rotation. This accordingly causes movement of the X-AXIS CARRIAGE 191, and of the reference LED 160 (both shown in FIG. 6) in accordance with the well known operation of an x-y plotter.

Signals developed within the current sense resistors 421, or the x,y HOME SENSORS 421, are received at the LIGHT SENSOR CONDITIONING CIRCUIT AND A/D CONVERTER 413 shown in FIG. 7. When these currents are zero then the carriage has finished moving to the prescribed position and may be so recognized to have finished moving by the computer. Accordingly, no stimuli are ever applied during the sequence of testing by the perimeter 100 in accordance with the present invention save that the relative positions of such stimuli, to the target LED and the intensities thereof, are precisely known and constantly monitored by the test-administrating computer.

Further in this context of the monitoring performed by the perimeter 100 in accordance with the present invention, a typical circuit for allowing the computer to sense light conditions is shown in FIG. 9. A LIGHT SENSOR 400, 423 —which may be either used to sense background illumination or the illumination intensity at any of the normally sixteen STIMULUS LEDS 150 and the typically one FIXATION TARGET LED(s) 160—senses the light intensity with a SILICON PHOTO SENSOR 424. The current output of the SILICON PHOTO SENSOR 424 is amplified in TRANSIMPEDANCE AMPLIFIER 425. The TRANSIMPEDANCE AMPLIFIER 425 is a current to voltage amplifier providing sufficient signal input to analog to digital converter A/D 413 (partial). The A/D 413 (partial) is part of the LIGHT SENSOR CONDITIONING CIRCUIT AND A/D CONVERTER 413 previously shown in FIG. 7. The output of the A/D 413 (partial) is placed on the computer BUS which is within cable 401.

By comparing the sensed light intensities to reference intensities the computer is able to accomplish several functions. The intensities of all LEDs are able to be maintained equal, and at an appropriate level relative to room illumination, at all times. It will be recalled that the level of intensity to which the STIMULUS LEDS 150 are adjusted is inversely proportional to a height (contrast sensitivity) on the island of vision. If the STIMULUS LEDS 150 are set maximally bright, then the isopter of the island of vision which is examined is the threshold limits of the island, or its "shoreline". At lower intensity levels sensed in LIGHT SENSOR 420, 423, other contours of the island of vision may be examined to generate other isopters. It should, of course, be further understood that the individual STIMULUS LEDS 150 may be varied, and dynamically varied, in intensity in order to permit performance of the static threshold, static super-threshold, and reverse kinetic perimetry methods of visual field examination with the perimeter 100 in accordance with the present invention. The predominant methods of the present invention—modified reverse kinetic perimetry (MRKP) and modified reverse kinetic perimetry with successive approximations (MRKP-SA)—both require variations in the illumination intensity of STIMULUS LEDS 150.

Figure 10:
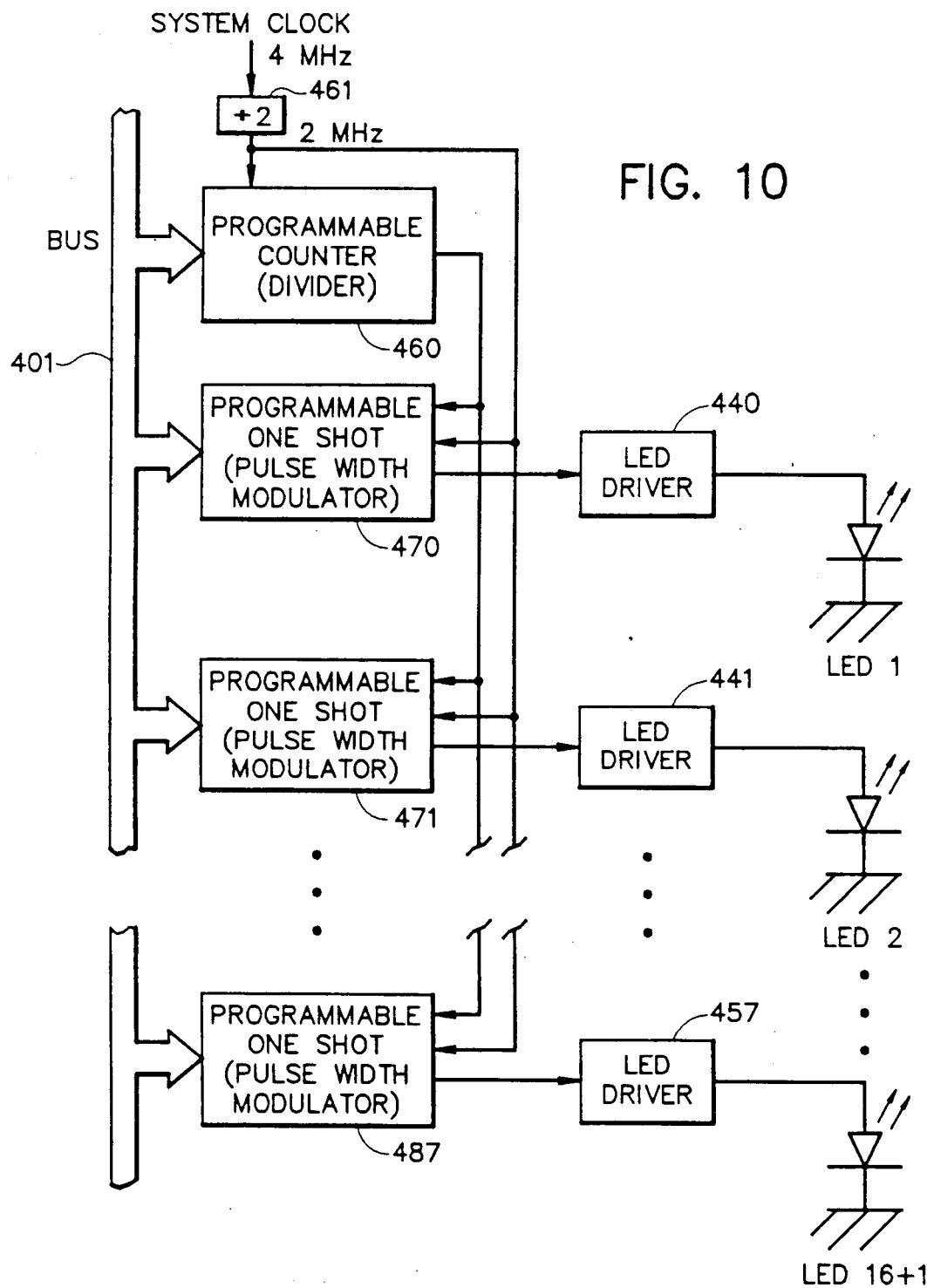
FIG. 10 is a schematic diagram showing the drivers of the target and fixation light emitting diodes (LEDs) in either embodiment of the ocular perimetry instrument in accordance with the present invention.

A detailed schematic diagram of FIXATION LED INTENSITY CKT 416, and the STIMULUS LED INTENSITY CKTS 419 (both previously seen in FIG. 7) is shown in FIG. 10. The normally sixteen STIMULUS LEDS 150 and the FIXATION TARGET LED(s) 160 are labeled LED 1 through LED 16+1. Each of the LED 1 through LED 16+1 is driven with current supplied from a corresponding LED driver 440-457. The length of time that each LED driver 440-457 is enabled to drive current through the corresponding LED 1—16+1, and the corresponding intensity of the light output from such corresponding LED, is controlled by the respective PROGRAMMABLE ONE SHOT (PULSE WIDTH MODULATOR) 470-487. Each of the PROGRAMMABLE ONE SHOT's 470-487 is programmed with the count representing a time interval during which it will produce a logically true enabling output signal via the computer bus upon cable 401.

The computer also programs, via the BUS that is within cable 401, the PROGRAMMABLE COUNTER (DIVIDER) 460. The PROGRAMMABLE COUNTER 460 receives a clock signal which is derived from the division of the SYSTEM CLOCK, nominally 4 MHz, in a divide-by-two circuit 461. The resultant timing signal supplied to the PROGRAMMABLE COUNTER 460 is of 2.0 megahertz frequency. This signal is further divided within the PROGRAMMABLE COUNTER (DIVIDER) 460 in accordance with the control parameter loaded therein by the computer. Normally, the frequency is divided to a granularity wherein the counts of size which may conveniently be installed in each of the PROGRAMMABLE ONE SHOT 450-459 will permit that each of the respective LED 1 - LED 16+1 shall be maintained at some duty cycle between 0% and 100%. Normally the granularity, or single bit division, of the count is at a very refined level, typically less than 1/10,000 of the total duty cycle. The illumination intensity is correspondingly controllable with great exactitude.

Referring again to FIG. 6, at the conclusion of testing (which may either prolonged or foreshortened in accordance with the computer determinations of test progress), the PERSONAL COMPUTER MOTHERBOARD 400 is able to calculate the visual field of the subject from the cumulative responses to the administered test regimen. This calculated visual field is preferably plotted in a conventional manner upon chart paper 181, which is normally 11" by 17" in size. In order to do so, the computer causes the PEN LIFT DRIVER 424 within I/0 BOARD 410 to selectively enable and disable the PEN LIFT SOLENOID 183 (all shown in FIG. 7), while simultaneously causing movement of X axis carriage 191 and the y AXIS CARRIAGE 192 to which the pen and PEN LIFT SOLENOID 183 is affixed, so as to cause the plotting of the isopters or other curves representative of the visual field of the eye. At the conclusion of this operation, the tray 180 containing the chart paper 181 may be slid from its position within the housing 111 to the Perimeter 100, and the chart paper 181 may be withdrawn for analysis by attending personnel and/or for display to the test subject.

A flow chart of the preferred embodiment of the software executed by the embedded PERSONAL COMPUTER MOTHER BOARD 400 within the ocular kinetic perimetry instrument, or perimeter 100, in accordance with the present invention is shown in FIG. 11, consisting of FIG. 11a through 11i. The software flowchart for initialization of the perimeter, and for the training of the optional perimeter voice recognizer circuitry to the verbal response of a particular patient, is shown in FIG. 11a. The voice recognizer training sequence, which is quite short, requires the participation of a doctor or other perimeter operator to determine that the patient is indeed voicing the correct response, i.e., "one", "two", "three" or "four".

The perimeter will digitalize and store any patient voiced response. The doctor or operator monitors the perimeter display, and ensures that the voiced response made to the perimeter by the patient is correctly indicative of the number of targets which are illuminated. The patient is instructed not to talk save for the voiced response, and the doctor or operator also does not talk. If the patient unduly hesitates, voices extraneous words, and/or other circumstances disrupt the training of the voice recognizer then it is a simple matter to recommence the initialization and voice recognition training sequence.

The software controlling the performance of a blind spot test phase 1 by the perimeter performing the method of reverse kinetic perimetry (RKP) is flow charted in FIG. 11b. This procedure is performed in order to locate the center of the blind spot. It is more tolerant of patient blind spot alignment than the blind spot test phase 2 flow charted in FIG. 11c. At the conclusion of the blind spot test phase 1 the computer of the perimeter arithmetically computes a centroid and area to the blind spot.

Figure 11C:
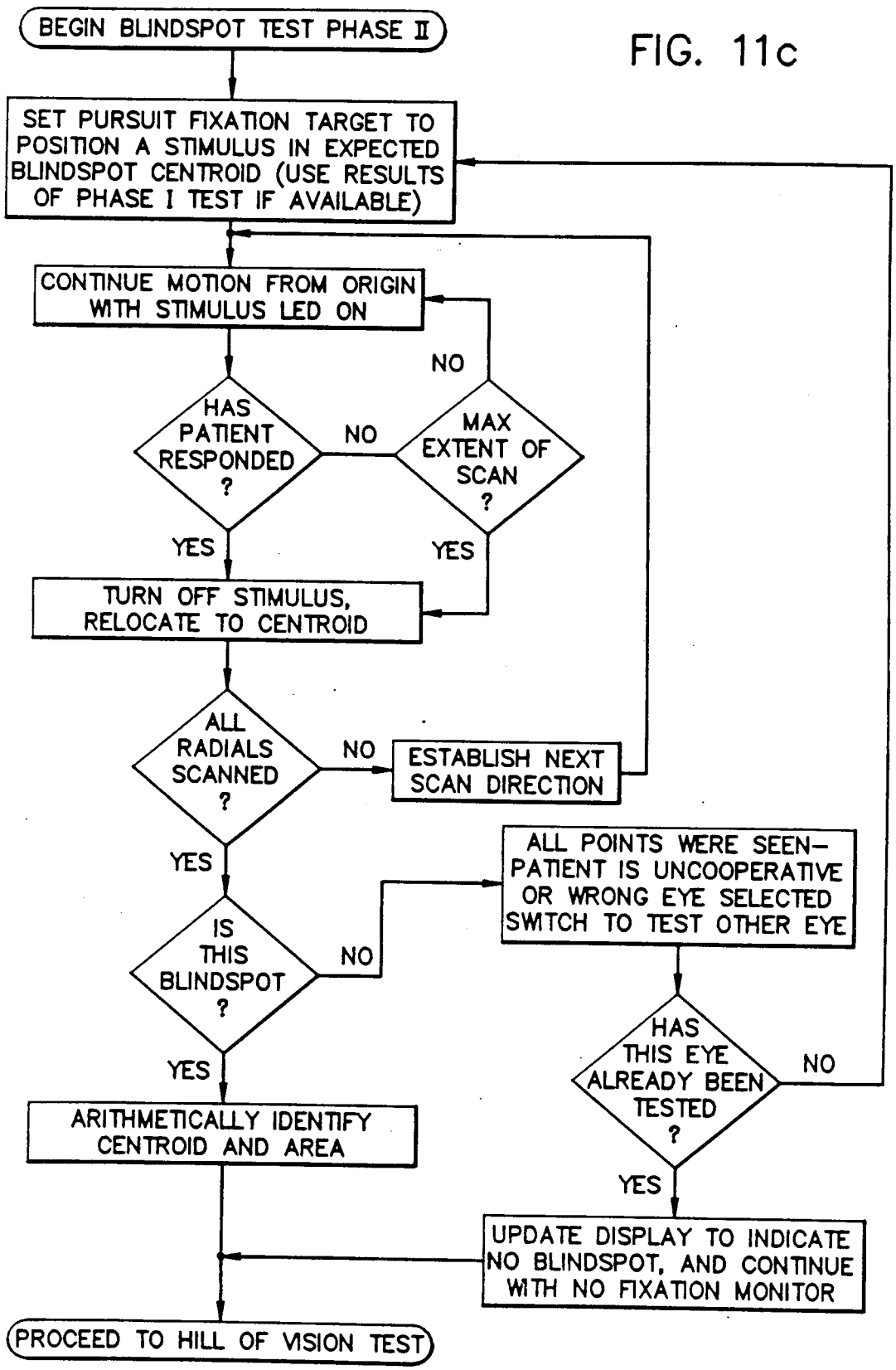
FIG. 11c is a third flowchart showing preferred software for executing a blind spot test phase 2 again by the RKP method, which software executed by the computer of an ocular perimetry instrument in accordance with the present invention.

A flow chart of the software for performing the blind spot test phase 2 again by the method of reverse kinetic perimetry (RKP) is shown in FIG. 11c. This blind spot determination is more exacting to define the extent of the blind spot than the phase 1 determination flow-charted in FIG. 11b. With some knowledge of the blind spot centroid and area resultant from the performance of test phase 1, stimuli are moved radially outward from the previously determined centroid of the blind spot. The patient responses to such stimuli further define the location and extent of the blind spot with exactitude. From this data that maps the blind spot the computer again arithmetically computes both the centroid and the area of the blind spot.

There are several uses for the determined location and extent of the blind spot. By knowing where the patient's eye's blind spot is at each fixation of the patient's eye the computer intermittently presents light stimuli within the patient's blind spot during the course of testing of visual sensitivity. If the patient responds to these presentations then the eye is not properly fixating (or tracking) the (moving) fixation target.

Another use of the computed blind spot is to reveal whether such blind spot is the normally sized blind spot which is present within all human eyes, or is instead an extensive area representing a scotoma. The determination transpiring within blind spot test phases 1 and 2 enables the perimeter, during its later performance of modified reverse kinetic perimetry (MRKP), to display appropriate stimuli. For example, plural targets that are tracked by the eye focusing at a point between the targets will permit a person with a scotoma such as, for example, a scotoma extending to within the area of the fovea, to visually track a moving target.

It should be understood that to this point the computer has not, and is not, testing the extent of the field of vision. The blind spot test phases 1 and 2 are simply to determine the extent and location of the natural blind spot within the patient's field of vision, and to permit the presentation of test stimuli that appropriately compensate for the extent and location of the blind spot. In a normal eye, which exhibits good vision at the fovea, the arithmetically calculated centroid and area of the blind spot will be indicative of the actual blind spot of the normal eye. In this case, no special presentation of visual stimuli will be required during the ensuing reverse optical perimetry testing, and a single moving target will suffice to be tracked by the eye of the patient. If, however, the patient exhibits a blind spot at his/her fovea centralis then multiple targets are presented in positions surrounding the blind spot and at an adequate separation therefrom so as to be detectable by the patient during the ensuing reverse optical perimetry testing. The partially blind patient will then be instructed to "look to the center of the group of moving lights."

The blind spot test phases 1 and 2 are true (unmodified) reverse kinetic perimetry (RKP). This RKP method is not the predominant method for the actual testing of the visual field.

Figure 11D:
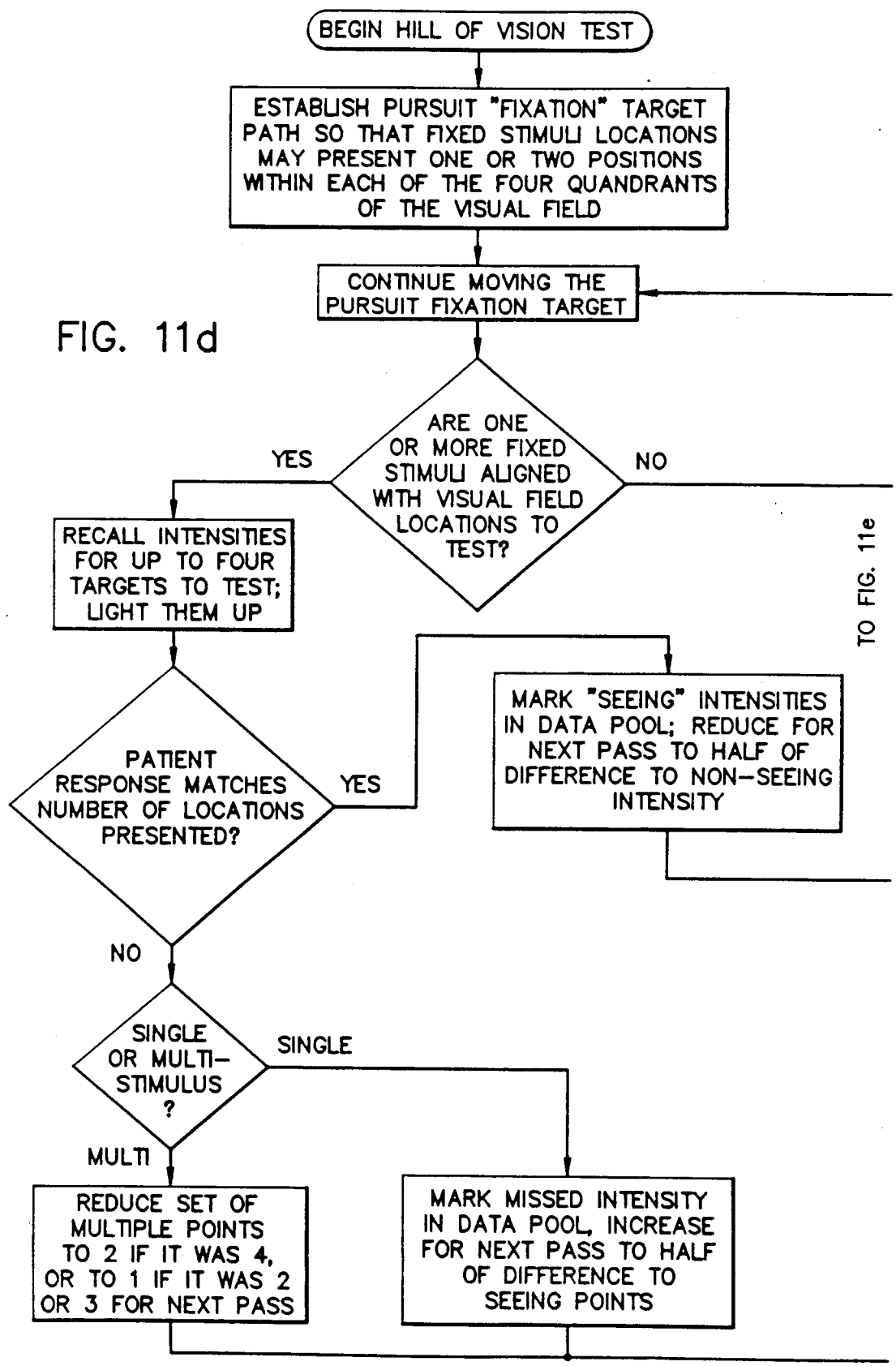
FIGS. 11d and 11e are fourth flowcharts showing preferred software for conducting modified reverse kinetic perimetry with successive approximations (MRKP-SA) for testing the field of vision test particularly at four points, the software being executed by the computer of an ocular perimetry instrument in accordance with the present invention.
Figure 11E:
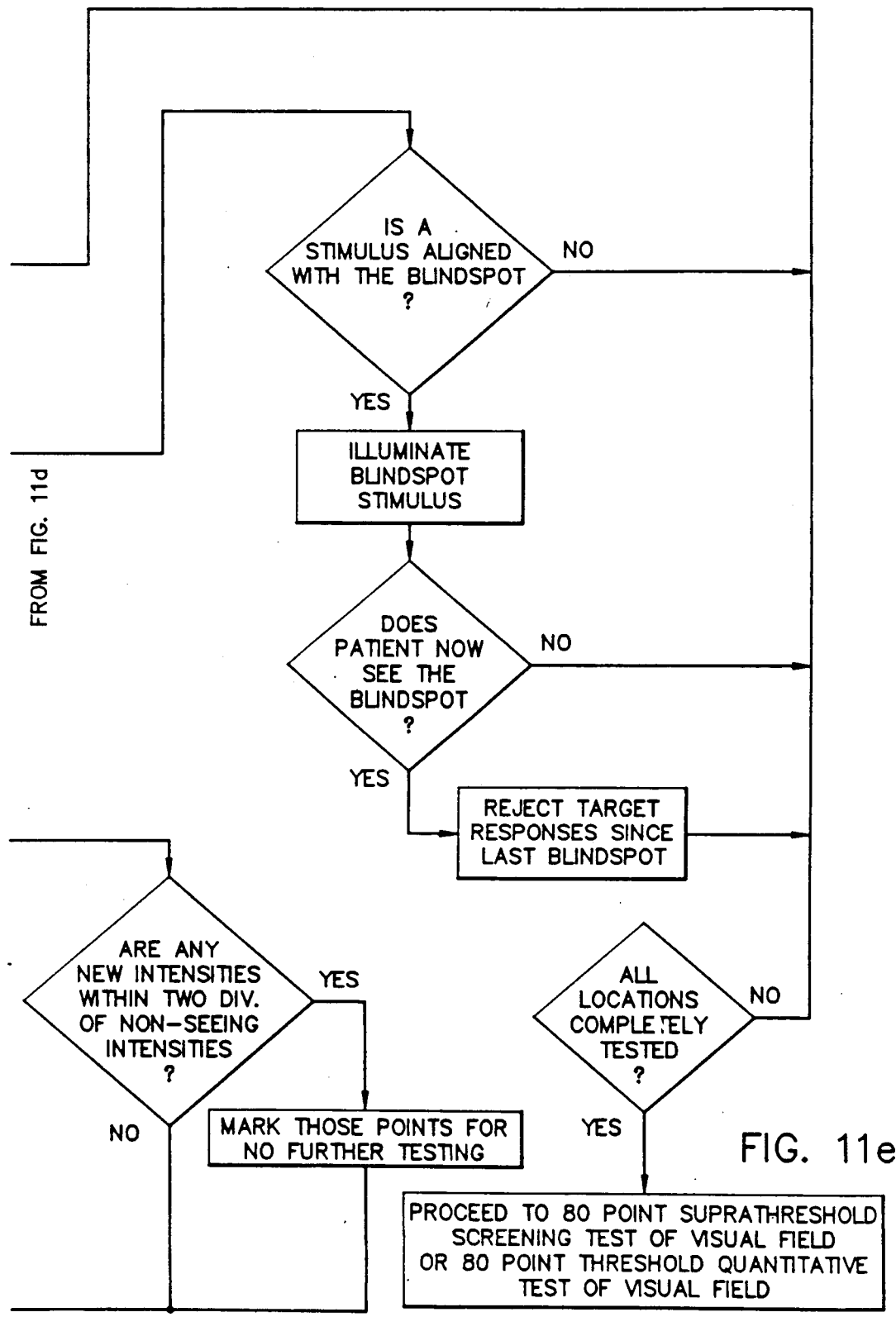
Figure 12:
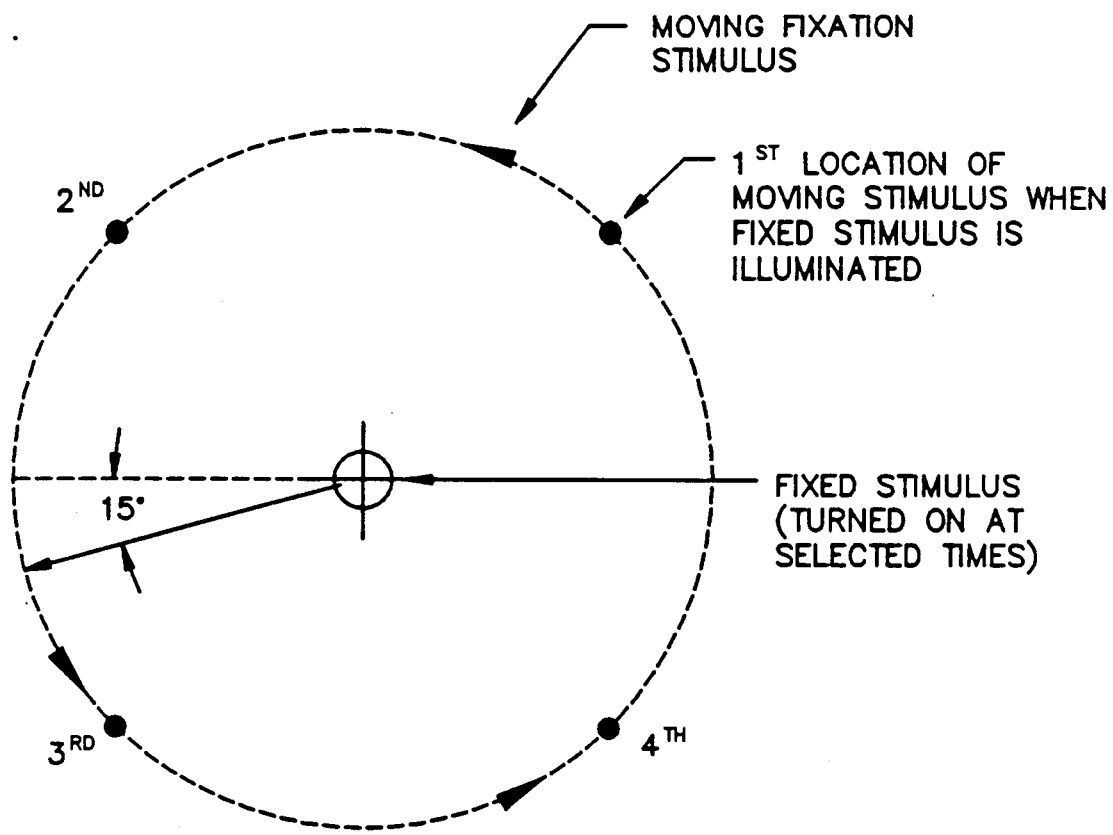
FIG. 12 is a diagrammatic representation of the simplified, conceptual, spatial relationships between a moving fixation stimulus and a fixed target stimulus at four different times of the monetary illumination of the target stimulus.

The software controlling the preliminary hill of vision test, which software controls the perimeter to perform modified reverse kinetic perimetry with successive approximations (MRKP-SA), is flow-charted in FIGS. 11d and 11e. The purpose of the test that is flow-charted in FIGS. 11d and 11e is to preliminarily determine the rough contours of the hill of vision. The computer causes the perimeter to present typically four test stimuli upon for iterations each, and to accumulate data responsively thereto. The location within the field of vision of the typically four points that are presented and tested is shown in FIG. 12.

Figure 13:
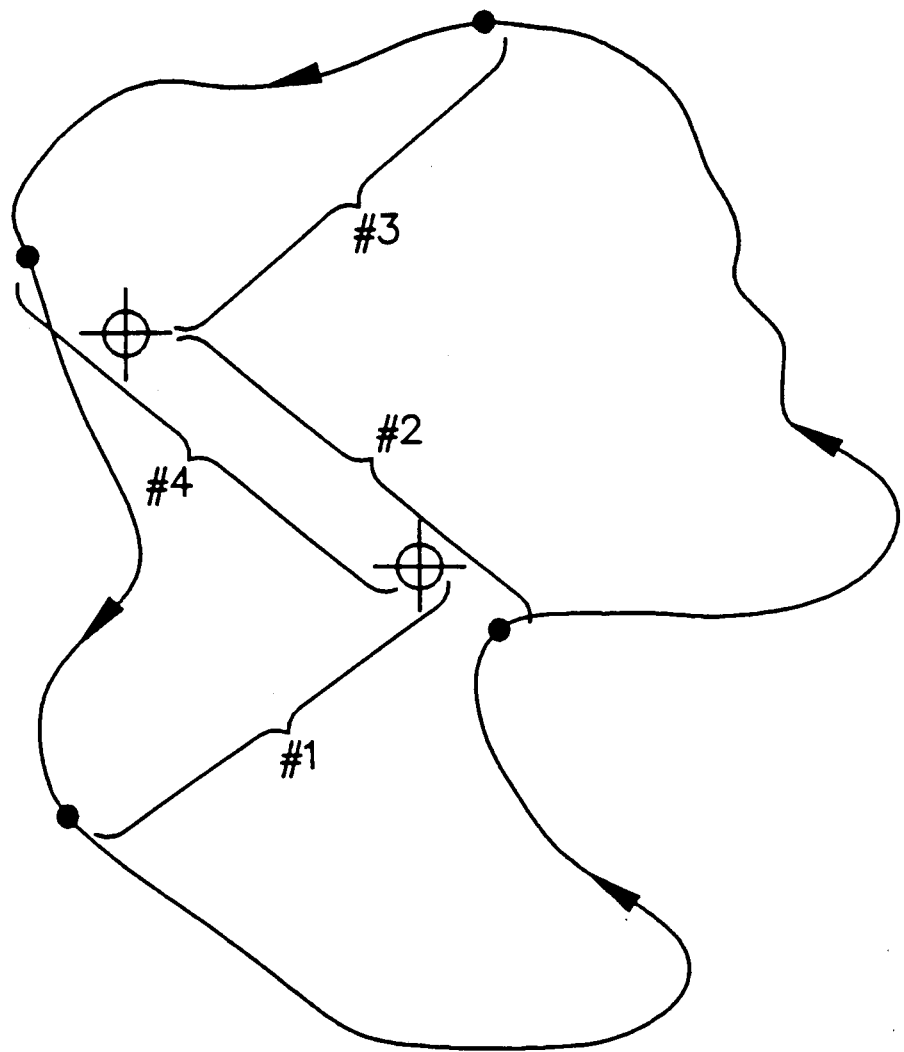
FIG. 13 is a diagrammatic representation of an actual serpentine path traced by a moving fixation stimulus showing the positions of the fixation stimulus in this path at four different times when a one of two target stimuli is illuminated, testing thereby four points that are successively approximated on the island of vision.

The typical manner of presentation is diagrammatically illustrated in FIG. 13. The moving fixation target traces a predetermined path under computer control. Fixed position test stimuli (of which an arbitrary two only are illustrated to be used) are momentarily illuminated when the fixation target is of an appropriate angle and separation. The patient response to each single illumination is processed. Normally the first iterative illumination at each of the typically four field of vision points is suprathreshold, or at a level likely to be seen. A next successive illumination is typically subthreshold. Illuminations continue for each point of successively closer approximations driven to be of greater or lessor illumination intensity by actual patient responses. Normally three only iterations for each of the four points, or twelve total trials, suffice for a sufficiently accurate characterization of the visual sensitivity of the four points. From this actual visual sensitivity a complete "shrunken" island of vision that is customized for the individual patient is calculated by the computer.

Returning to FIGS. 11d and 11e, the course of sequential testing by the MRKP-SA method may be observed therein. The accumulated data actually permits the computer to calculate not one but two pseudo "hills of vision" which are respectively inside (smaller than) and outside (bigger than) the actual hill of vision. The smaller hill of vision is the assured "seen" sensitivity of the patient's eye. In other words, any test stimuli presented at the appropriate intensity and at an appropriate location so as to be within this pseudo hill of vision are assured to be seen by the patient save that the patient's eye exhibits visual defects. The larger, outside, pseudo hill of vision represents the assured "non-seen" locations and intensities that are outside the hill of vision of the patient. Any stimuli at an intensity and a displacement that is outside of this pseudo hill of vision is assuredly not detectable by the patient. The intensity of stimuli presented in the patient's blind spot is normally suprathreshold to this "outside" hill of vision.

Figure 11F:
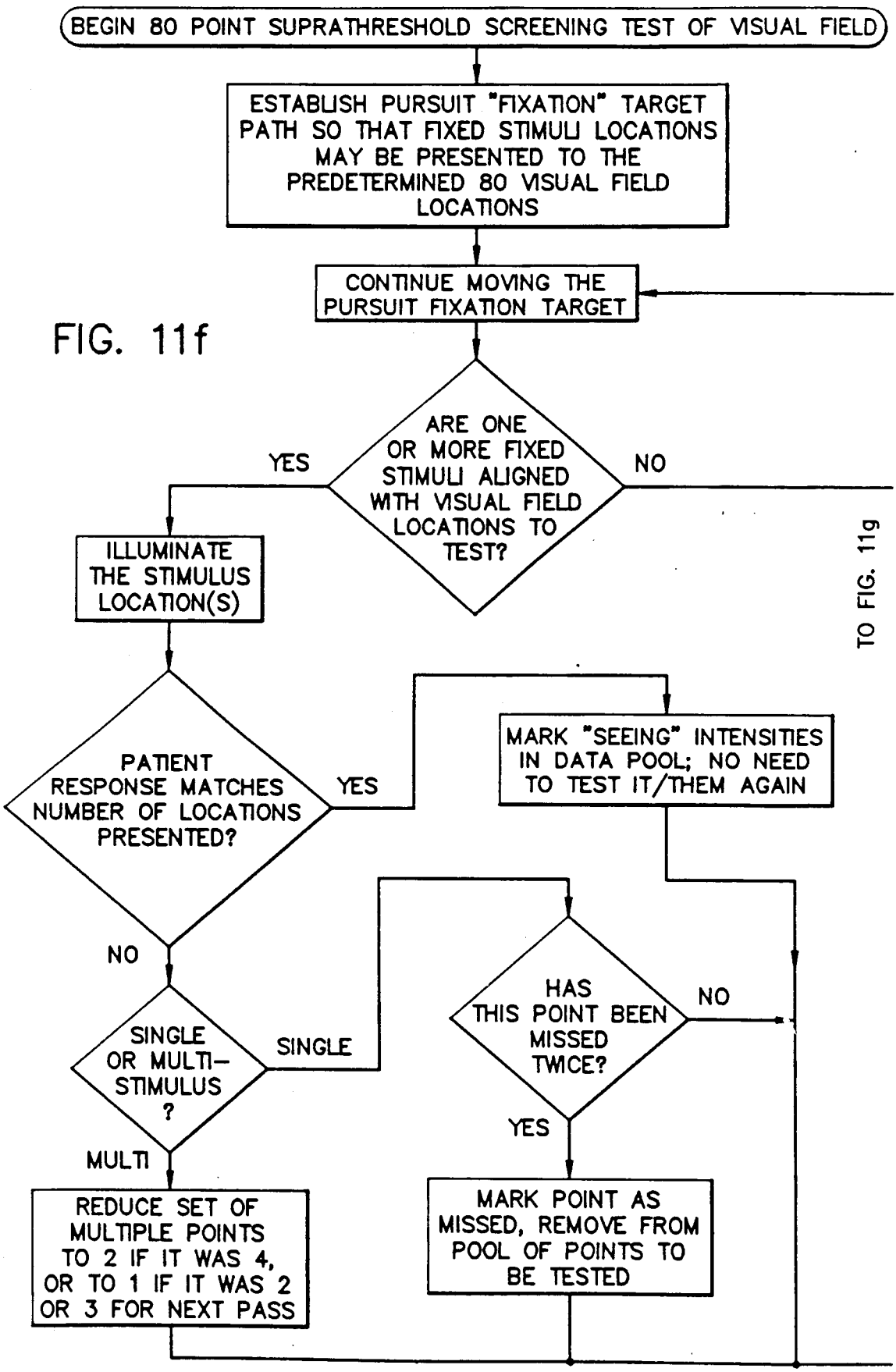
FIGS. 11f and 11g are fifth flowcharts showing preferred software for performing an 80 point modified reverse kinetic perimetry (MRKP) screening test of the visual field, the software being executed by the computer of an ocular perimetry instrument in accordance with the present invention.
Figure 11G:
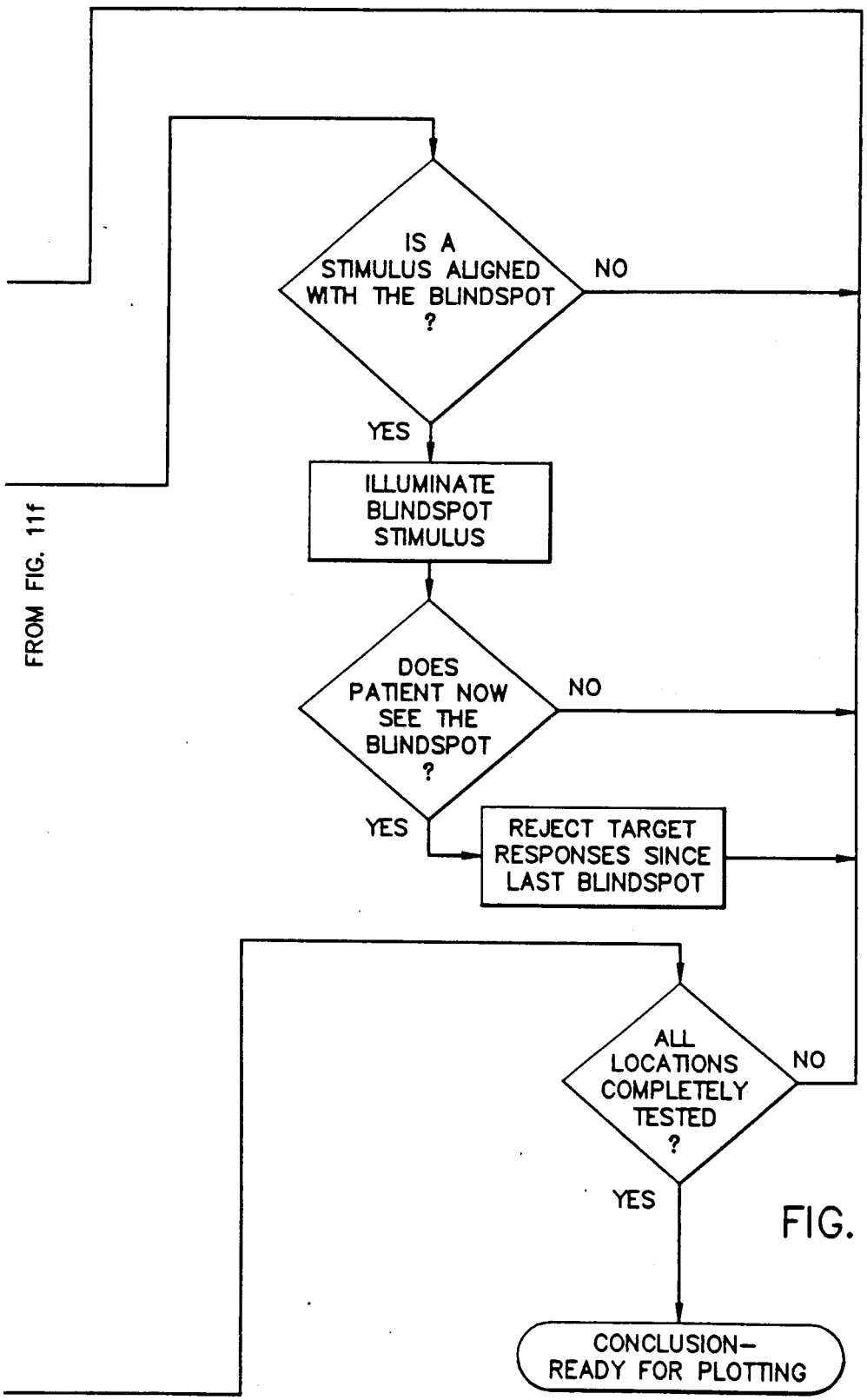
Figure 11H:
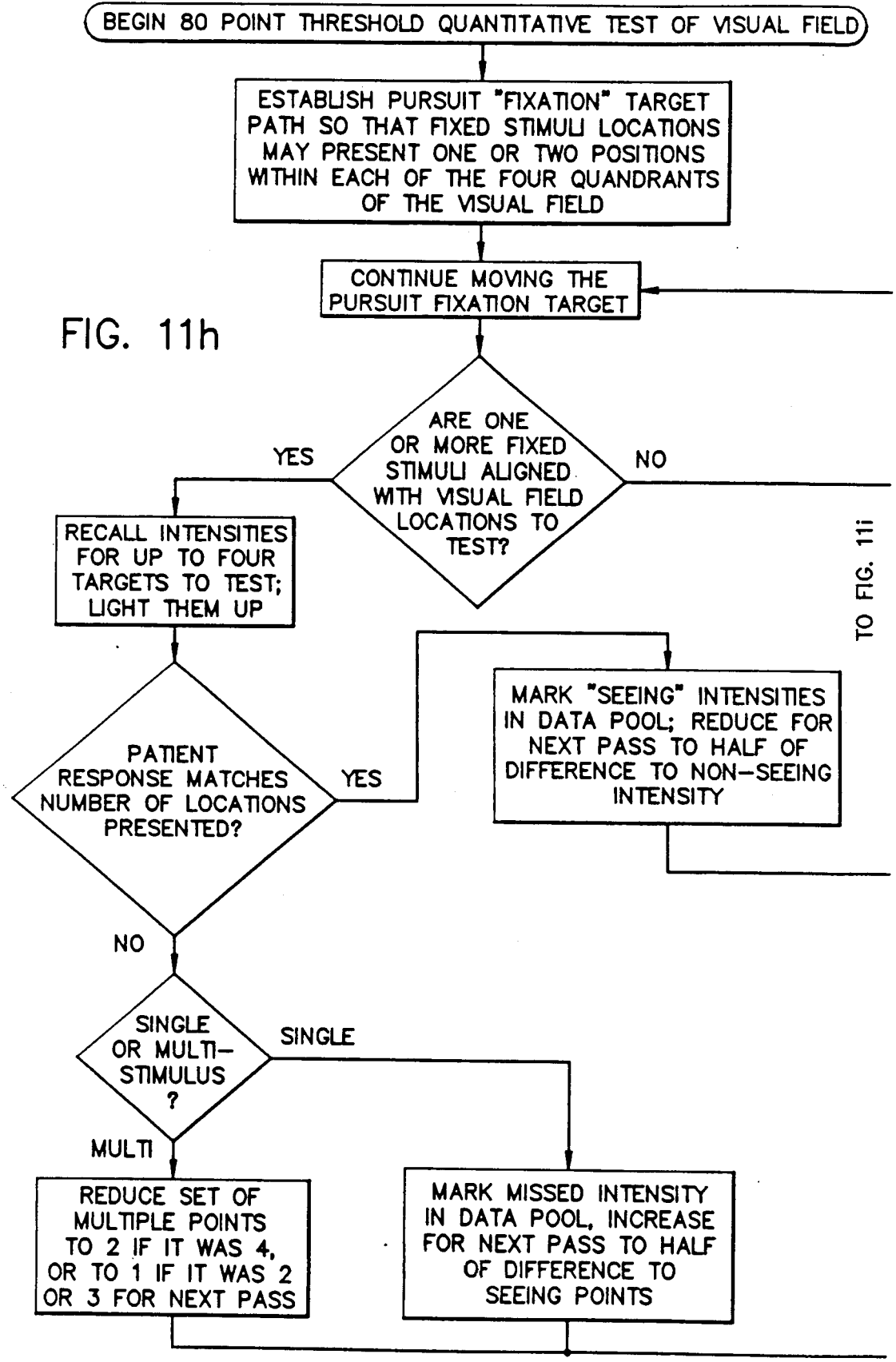
FIGS. 11h and 11i are sixth flowcharts showing preferred software for performing an 80 point modified reverse kinetic perimetry with successive approximations (MRKP-SA) quantitative test of the visual field, the software being executed by the computer of an ocular perimetry instrument in accordance with the present invention.
Figure 11I:
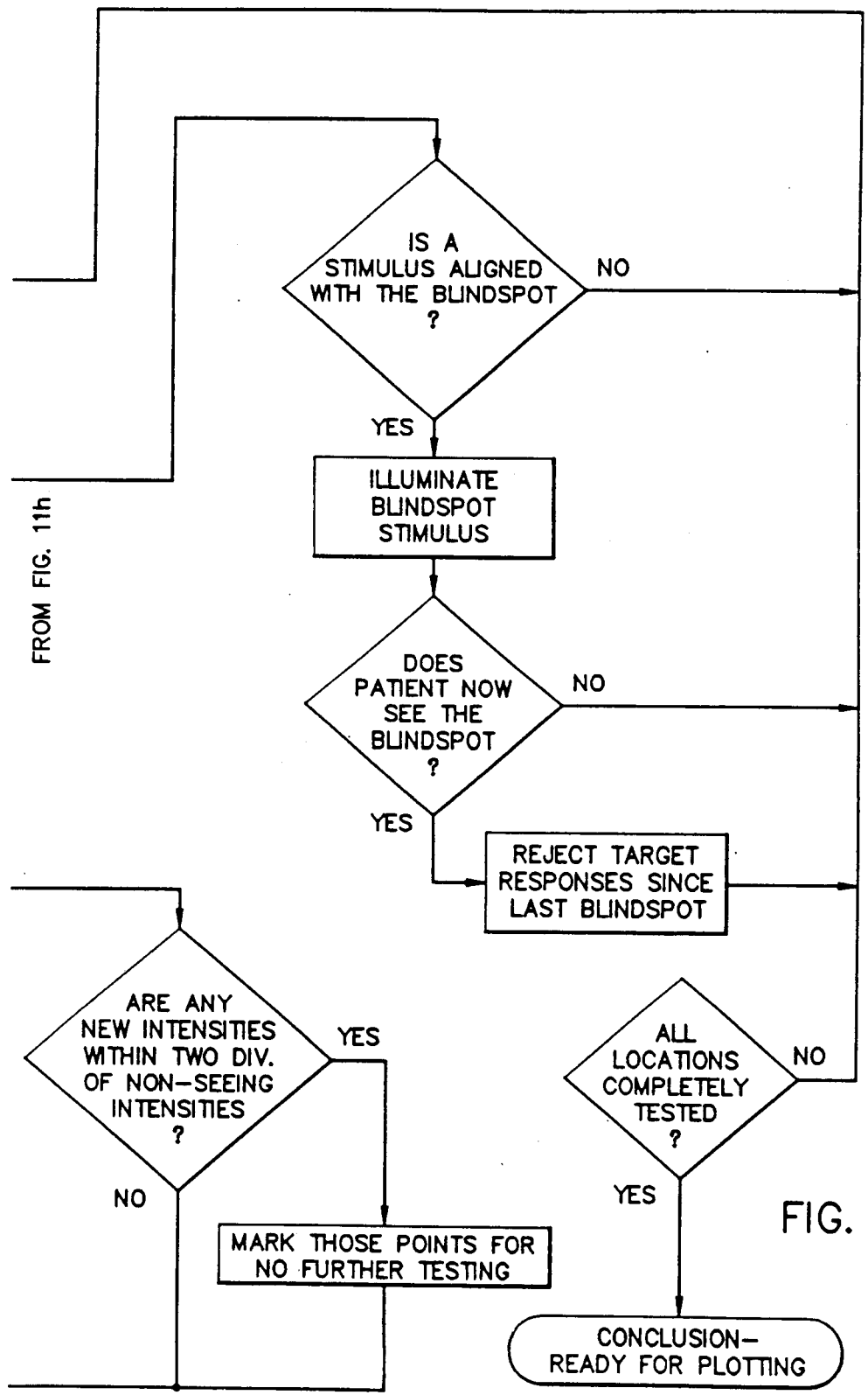

The computerized perimeter in accordance with the present invention continues from the preliminary modified reverse kinetic perimetry with successive approximations (MRKP-SA) testing to still further testing in order to definitively quantify the actual, precise, hill of vision of a particular patient. This further testing may be either by the modified reversed kinetic perimetry (MRKP) method flow charted in FIGS. 11f and 11g or by the modified reverse kinetic method with successive approximations (MRKP-SA) flow charted in FIGS. 11h and 11i. It is preferably by the modified reverse kinetic perimetry (MRKP) method. The MRKP method preferably presents suprathreshold stimuli to the shrunken hill of vision. The software flow chart for the presentation of an 80 point suprathreshold MRKP screening test of the visual field is shown in FIGS. 11f and 11g. The software flow chart for the presentation of an 80 point threshold quantative MRKP-SA test of the visual field is shown in FIGS. 11h and 11i. Both tests produce a highly accurate three dimensional map of the contours of the actual patient hill of vision. This map is plotted for interpretation by a medical professional.

Figure 15:
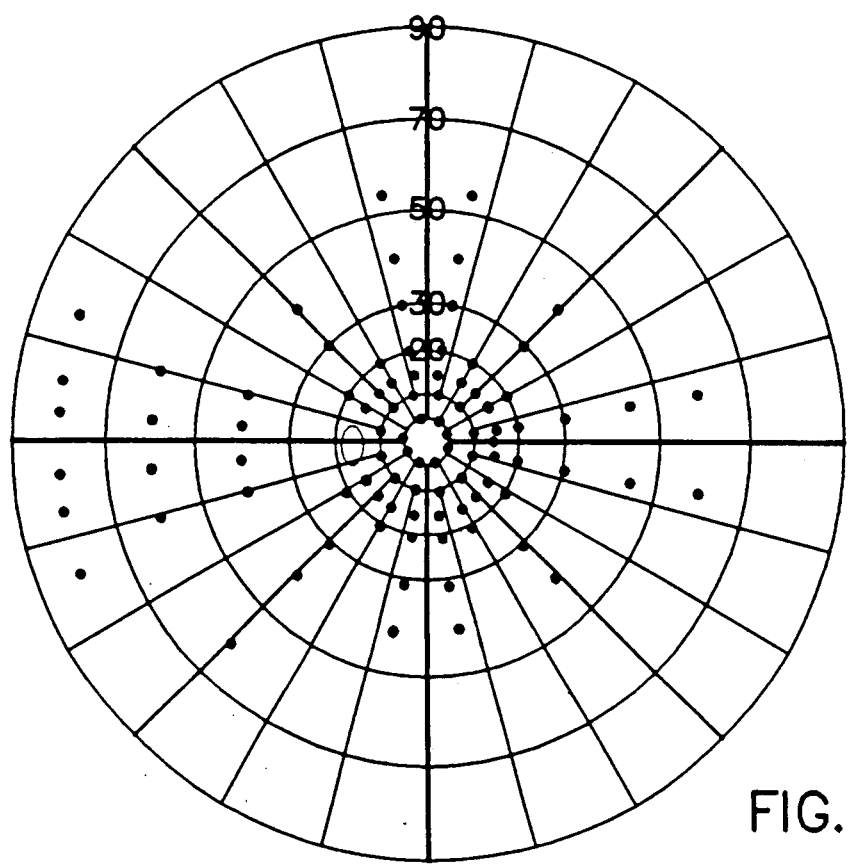
FIG. 15 is a graph showing 80 points that are tested within the visual field of the left eye during testing in accordance with the present invention.

The preferred location of the eighty points tested for, by example, the left eye during each quantitative MRKP or MRKP-SA test of the visual field is diagrammed in FIG. 15. The corresponding eighty points for the testing of the visual field of the right eye, over the top of which are drafted 3 isopter lines of constant visual sensitivity, are shown in FIG. 16a. Defects in the visual field, or points whereat the visual sensitivity tests subthreshold to the shrunken island of vision are marked by triangles.

A graphical plot of the inner isopter of particular interest from FIG. 16a versus the normal isopter of a standard sensitivity visual field calibrated to the individual patient's individual eye is shown in FIG. 16b. Still another, cross-sectional, profile of the visual field, taken along horizontal axis line "O" shown in FIG. 16b, is shown in FIG. 16c. The top curve within FIG. 16c represents a normal hill of vision for a person of the patient's age. The lower curve represents the patient's actual vision. The eye shows a defect that may be associated by a trained opthamologist with the probable pathological condition of glaucoma.

A listing of the BASIC language source code of software executable by the IBM PC-compatible computer mother board within the optical perimeter in accordance with the present invention is attached as Appendix 1. Appendix 1 contains software routines controlling interrupt handling, motor drive control, and display drive control. It is thus specific to the particular hardware, including an x-y plotter, that is employed. Appendix 2 contains software controlling the conduct of automated perimetry. The software, divided into easily recognizable subroutines, is general to perform the indicated functions which, in aggregate, comprise the preferred methods and sequences of testing in accordance with the present invention. Modifications, or alterations, to this software will be perceived to be possible in accordance with adaptations of the present invention for performing tests other than reverse optical kinetic perimetry and its derivatives. Appendix 3 contains a sample printout (obtained on a printer which may optionally be connected or temporarily connected to PERSONAL COMPUTER MOTHERBOARD 400 shown in FIGS. 6 and 7) of the data obtained by performance of qualitative testing in accordance with the present invention. The testing is, by example, for ninety-nine (99) as opposed to the conventional eighty (80) points.

In accordance with the preceding discussion, it will be recognized that the present invention offers considerable flexibility, efficiency, and effectiveness in the conduct of totally automated testing of the visual field. The automated testing that transpires is nearly foolproof. The preferred embodiment of the perimeter 100 in accordance with the present invention calibrates itself. It will pause during the conduct of testing, even aborting if necessary, if no rational stimuli are received from the patient. Additionally, although a patient who is either incompetent, malingering, or obstructing the course of testing may defeat the regimen of testing by refusing to respond to stimuli, it is difficult for a patient to fake better results than are legitimately reflective of the extent and acuity of the patient's visual field. Cooperative patients generally find the test regimen easy, quick, and painless. Uncooperative test takers, or malingers, are not able to generate responses that produce test results which are subject to misinterpretation or, in most cases, to register sufficiently adequate progress during testing so that the automated perimeter will not cease testing and alert the operator. The appropriate responses to uncooperative, or malingering, test subjects are of particular importance where a machine is used to screen a large population, such as recruits to the military forces, wherein the cooperation of the individual subjects is uncertain.

In accordance with the preceding remarks, both the preferred method and the preferred embodiment of an apparatus in accordance with the present invention are obviously subject to variation. The movement of the fixation point light source could have been accomplished by selective illuminations of elements within an array of illuminatable light sources. Normally, the elements would be successively illuminated one to the next thereby causing a stepping progression in the position of the light source which is fixated by the eye of the patient. Alternatively the invention could be implemented by means of a conventional target light source-directed via motors, lenses and mirrors to a planar or curved screen which contains a multiplicity of fixed light sources as stimuli.

The presentation field of the perimeter need not have been a flat tangent screen. The methods of the present invention could be implemented within a hemispherical bowl perimeter. The number of stimulus light sources need not have been set at sixteen, need not have been light emitting diodes, and need not have been fixed in position. The computer need not have used the same mechanism which is otherwise used to move the light sources during the course of testing to generate, in graphical chart form, the test results but could instead be connected, as by a data bus, to a conventional graphics printer or the like.

Corresponding to these and other obvious modifications, the present invention should be perceived broadly. In particular, the scope of the invention should be determined by the following claims, only, and not solely in accordance with that particular embodiment within which the invention has been taught.

APPENDIX 1

```
TITLE   VISMED, Inc. TKS-4000    8088 Assembly language routines
PAGE    58,80
PUBLIC  Initial, Character, MotorControl, SetTimer, ReadTimer
PUBLIC  Buttons, LightLevel, GetAdc, Time,COMPARRAY,CLOSELEMENT

.MODEL MEDIUM

;=============================================================;
;   VISMED TKS-4000 Interrupt handler, motor driver, and display   ;
;           driver routines, written by Vincent Brancaccio         ;
;           documentation added by Bryan G. Moore                  ;
;                                                                  ;
;=============================================================;
;
BLINKER   EQU    -1       ;fixation (pursuit) -1 = blinking, 0.= no
LEDOFF    EQU     0       ;LED OFF STATE             ;
;TimerFreq EQU  4000      ;Time Intvl (1.19318Mhz/TIMERFREQ = TIME BASE)
TimerFreq EQU  12000      ;INTERUPT TIME INTERVAL apparently 3x rate
PULSEWIDTH EQU 65535      ;THE LED (8253) GATE SIGNAL (54Hz)
```

```
; I/O Ports
PORT20   EQU     20H        ;Control port for 8259 interrupt controller
PORT21   EQU     21H        ;Interrupt mask register for 8259
PORT40   EQU     40H        ;Timer channel 1 of motherboard 8253-5 timer
PORT43   EQU     43H        ;Mode port for motherboard 8253-5 timer
;
PORT300  EQU     300H       ;Input: Bit 4 = Motors status bit (0=not moving)
                            ;       bit 1 = opperator button (active low)
                            ;       bit 0 = used by motorcontrol (hand shaking)
                            ;Out bits: Solenoid and motor Control:
                            ;Bit 5 = current level select (0-high)
                            ;    4 = activate solenoid.
                            ;    3 = Motor command strobe
                            ;    2 = shift register reset.
                            ;    1 = X direction
                            ;    0 = Y direction
PORT302  EQU     302H       ;OUT - port #2 display control port:
                            ;       BITS 5,6,7 ARE ADC MUX CHANEL SELECT
                            ;       bits 4-0 dot data.
PORT303  EQU     303H       ;OUT - port #1 display control port:
                            ;       Bits 7,6,5 dot row strobe;  Bits 4-0 dot data
                            ;IN  - port for adc input
PORT304  EQU     304H       ;Y-direction step rate generator
PORT305  EQU     305H       ;X-direction step rate generator
PORT306  EQU     306H       ;Y displacement counter
PORT307  EQU     307H       ;Control port for 8253 addressed by 304-306
PORT308  EQU     308H       ;X displacement counter
MODULATION EQU   309H       ;LED MODULATION PORT
PURSUITLED EQU   30AH       ;PURSUIT LED BRIGHTNESS PORT
PORT30B  EQU     30BH       ;CONTROL PORT FOR 8253 ADDRESSED BY 308-30A
PORT30C  EQU     30CH       ;LED brightness control counter group A
PORT30D  EQU     30DH       ;LED brightness control counter group B
PORT30E  EQU     30EH       ;LED brightness control counter group C
PORT30F  EQU     30FH       ;CONTROL PORT FOR 8253 ADDRESSED BY 30C-30E
PORT310  EQU     310H       ;LED brightness control counter group D
PORT311  EQU     311H       ;8253 - routed to DB9 connector (new comment)
PORT312  EQU     312H       ;8253 - temp assigned to IRQ7
PORT313  EQU     313H       ;CONTROL PORT FOR 8253 ADDDRESSED BY 310-312
PORT314  EQU     314H       ;ADC CONTROL
;
.DATA
; Character generator tables: Each group of seven (7) bytes contains a
; 5x7 character dot matrix for a specific displayable character. The
; top row of 5 dots is represented by the first of seven bytes, the
; bottom by the last byte. The LSB is the leftmost dot, the fifth bit
; (bit 4) is rightmost. Bits 5 - 7 are not used.
;
;          BitBitBitBitBit   Example for "0"  7654 3210
; First    0 1 2 3 4          _ X X X _     = 0000 1110 = 0EH
; Second   0 1 2 3 4          X _ _ _ X     = 0001 0001 = 11H
; Third    0 1 2 3 4          X X _ _ X     = 0001 0011 = 13H
; Fourth   0 1 2 3 4          X _ X _ X     = 0001 0101 = 15H
; Fifth    0 1 2 3 4          X _ _ X X     = 0001 1001 = 19H
; Sixth    0 1 2 3 4          X _ _ _ X     = 0001 0001 = 11H
; Seventh  0 1 2 3 4          _ X X X _     = 0000 1110 = 0EH
;
; Digits 0 - 9
Char     DB      0EH,11H,13H,15H,19H,11H,0EH   ; 0
         DB       4,  6,  4,  4,  4,  4, 1FH   ; 1
         DB      0EH,11H,10H, 8,  4,  2, 1FH   ; 2
         DB      0EH,11H,10H,0CH,10H,11H,0EH   ; 3
         DB      11H,11H,11H,1FH,10H,10H,10H   ; 4
         DB      1FH, 1,  1, 0FH,10H,10H,0FH   ; 5
         DB      0EH,11H, 1, 0FH,11H,11H,0EH   ; 6
         DB      1FH,10H,10H, 8,  8,  4,  4    ; 7
         DB      0EH,11H,11H,0EH,11H,11H,0EH   ; 8
         DB      0EH,11H,11H,1FH, 1H,10H,10H   ; 9
```

```
; Letters A - Z
Char1   DB      0EH,11H,11H,1FH,11H,11H,11H    ; A
        DB      0FH,11H,11H,0FH,11H,11H,0FH    ; B
        DB      0EH,11H, 1, 1, 1, 11H,0EH      ; C
        DB      0FH,11H,11H,11H,11H,11H,0EH    ; D
        DB      1FH, 1, 1, 0FH, 1, 1 ,1FH      ; E
        DB      1FH, 1, 1, 0FH, 1, 1, 1        ; F
        DB      0EH,11H, 1,1DH,11H,11H,0EH     ; G
        DB      11H,11H,11H,1FH,11H,11H,11H    ; H
        DB      1FH, 4, 4, 4, 4, 4, 1FH        ; I
        DB      1FH, 8, 8, 8, 8, 9, 6          ; J
        DB      11H, 9, 5, 3, 5, 9, 11H        ; K
        DB       1, 1, 1, 1, 1, 1, 1FH         ; L
        DB      11H,1BH,15H,11H,11H,11H,11H    ; M
        DB      11H,13H,13H,15H,15H,19H,19H    ; N
        DB      0EH,11H,11H,11H,11H,11H,0EH    ; O
        DB      0FH,11H,11H,0FH, 1, 1, 1       ; P
        DB      0EH,11H,11H,11H,15H, 9, 16H    ; Q
        DB      0FH,11H,11H,0FH, 5, 9, 11H     ; R
        DB      1EH, 1, 1, 0EH,10H,10H,0FH     ; S
        DB      1FH, 4, 4, 4, 4, 4, 4          ; T
        DB      11H,11H,11H,11H,11H,11H,0EH    ; U
        DB      11H,11H,11H,0AH,0AH, 4, 4      ; V
        DB      11H,11H,11H,11H,15H,1BH,11H    ; W
        DB      11H,11H,0AH, 4, 0AH,11H,11H    ; X
        DB      11H,11H,0AH, 4, 4, 4, 4        ; Y
        DB      1FH,10H, 8, 4, 2, 1, 1FH       ; Z
;blank character
Char2   DB       0, 0, 0, 0, 0, 0, 0           ; _
;
TEMP     DW      00      ;TEMPARY VARIABLE
TEMP1    DW      00      ;
TEMP2    DW      00      ;
TEMP3    DW      00      ;
TEMP4    DW      00      ;
MIN      DW      00      ;
POSX1    DW      00      ;VAR USED IN COMP ARRAY PROCEDURE
POSX2    DW      00      ;VAR USED IN COMP ARRAY
POSY1    DW      00      ;VAR USED IN COMP ARRAY
POSY2    DW      00      ;VAR USED IN COMP ARRAY
INDEX    DW      00      ;VAR USED IN COMP ARRAY
ELEMENTS DW      00      ;VAR USED IN COMP ARRAY
NUMMATCHES DW    00      ;VAR USED IN COMP ARRAY
;
TIMELOW  DW      00      ;LOW BYTE TIME OF DAY
TIMEHIGH DW      00      ;HIGH BYTE TIME OF DAY
TIMER1   DW      00      ;Contains the length of time the leds
                         ;will remain on.
SCANROW  DB      00      ;The row currently being displayed on
                         ;the alphanumeric displays.
DSPLY1   DB      0, 0, 0, 0, 0, 0, 0  ;The current character being
                                       ;displayed on display #1
DSPLY2   DB      0, 0, 0, 0, 0, 0, 0  ;The current character being
                                       ;displayed on display #2
OLDCONTROL DB    00      ;Passed by BASIC from PositionControl procedure
                         ;Bit 0 = Y direction
                         ;    1 = X direction
                         ;    2 = reset for shift register
                         ;    3 = Reserved for strobe
                         ;    4 = activate solenoid.
                         ;    5 = select current level.
                         ;    6 =
                         ;    7 =

PUSHBUTTON DB    00      ;KEEP TRACK IF BUTTON IS CURRENTLY BEING PREESED
BUTTON   DB      00      ;Bit 1 is used by the interupt. every time the
                         ;button is pressed bit 1 will go high, until
```

```
                        ;basic resets it to low.
Chanel  DB      00      ;ADC Mux chanel select
Blink   DB      ?       ;Blink timer .CODE
        PUBLIC initial
Initial PROC
        PUSH    BP
        CLI
        MOV     AX,0
        MOV     ES,AX
        MOV     DI,0FH * 4      ;Interrupt 15 decimal, same as IRQ7
        MOV     AX,OFFSET Interupt
        STOSW                   ;New offset
        MOV     AX,CS
        STOSW                   ;New segment
        MOV     DX,PORT313      ;Timer control port
        MOV     AL,0B6H         ;Counter 2, square wave mode
        OUT     DX,AL           ;Setup interrupt for Vismed
        DEC     DX              ;Bump to timer register
        MOV     AX,TimerFreq    ;Set frq to approx 298 Hz
        OUT     DX,AL           ;Interval low byte
        MOV     AL,AH
        OUT     DX,AL           ;Interval high byte
        IN      AL,PORT21       ;Read interrupt mask
        AND     AL,07FH         ;Engage IRQ7
        OUT     PORT21,AL       ;Set new interrupt mask
        MOV     DX,PORT300      ;CLEAR SHIFT REGISTERS
        MOV     AL,0
        OUT     DX,AL
        MOV     DX,PORT307              ;RESET 8253 (MOTOR) (CHANEL 1-3)
        MOV     AL,36H
        OUT     DX,AL
        MOV     AL,76H
        OUT     DX,AL
        MOV     AL,0B2H
        OUT     DX,AL
        MOV     DX,PORT30B              ;RESET 8253 (MOTOR+PULSE WIDTH+LED)
        MOV     AL,32H
        OUT     DX,AL
        MOV     AL,76H
        OUT     DX, AL
        MOV     AL, 0B2H
        OUT     DX, AL
        MOV     DX,PORT30F              ;RESET 8253 (LEDS) (CHANEL 1-3)
        MOV     AL,32H
        OUT     DX, AL
        MOV     AL, 72H
        OUT     DX, AL
        MOV     AL, 0B2H
        OUT     DX, AL
        MOV     DX,PORT313              ;RESET 8253 (LEDS) (CHANEL 1 ONLY)
        MOV     AL,32H
        OUT     DX, AL
        MOV     DX,MODULATION           ;INITIALIZE THE PULSE MODULATION
        MOV     AX,PULSEWIDTH           ;CHANEL OF THE 8253
        OUT     DX,AL
        MOV     AL,AH
        OUT     DX,AL
        MOV     TIMER1,1                ;TURN OFF ALL TARGET LEDS
        MOV     DX,PURSUITLED           ;TURN OFF PURSUIT LED
        MOV     AX,LEDOFF
        OUT     DX,AL
        MOV     AL,AH
        OUT     DX,AL
        STI
        POP     BP
        RET
```

```
Initial ENDP
;
Interupt PROC
        PUSH    AX
        PUSH    BX
        PUSH    CX              ;Save registers
        PUSH    DX
        PUSH    DS
        MOV     AX,@DATA
        MOV     DS,
        MOV     DX,POF 300
        IN      AL,DX           ;get status byte.
        AND     AL,2            ;Get push button bit (depressed if low)
        JNZ     NOBUTTON        ;JUMP IF NO BUTTON HAS BEEN PUSHED.
        CMP     AL,PUSHBUTTON
        JE      NOBUTTON
        INC     BUTTON          ;COUNT # OF PUSHES
NOBUTTON:
        MOV     PUSHBUTTON,AL
        INC     TIMELOW         ;OUR TIMER (4 BYTES) LOW 2 BYTES
        JNZ     LTIMER
        INC     TIMEHIGH        ;HIGH 2 BYTES
LTIMER: DEC     TIMER1          ;decreament led on timer.
        JNZ     ALPHA           ;if not time to turn off all leds then jump
        MOV     BX,LEDOFF       ;turn off all target leds
        MOV     DX,PORT30C
        MOV     AL,BL
        OUT     DX,AL
        MOV     AL,BH
        OUT     DX,AL
        MOV     DX,PORT30D
        MOV     AL,BL
        OUT     DX,AL
        MOV     AL,BH
        OUT     DX,AL
        MOV     DX,PORT30E
        MOV     AL,BL
        OUT     DX,AL
        MOV     AL,BH
        OUT     DX,AL
        MOV     DX,PORT310
        MOV     AL,BL
        OUT     DX,AL
        MOV     AL,BH
        OUT     DX,AL           ;end of "turn of target leds".
;begining of alphaNumeric display driver interupt.
ALPHA:  DEC     SCANROW         ;Set new scan row.
        MOV     AL,SCANROW      ;Get display row select.
        AND     AX,7H           ; 0 - 7 this is the row being displayed.
        MOV     BX,AX
        MOV     CL,5
        SHL     AL,CL           ;Shift to bits (5,6,7) row select.
        OR      AL,[BX+DSPLY1]  ;Merge row select with dot pattern led #1
        MOV     DX,PORT303      ;send info to alphanumeric display #1
        OUT     DX,AL           ;
        MOV     AL,[BX+DSPLY2]  ;Get second char dot pattern.
        OR      AL,CHANEL       ;get mux chanel right (bits 5,6,7)
        DEC     DX              ;Offset to second display output port.
        OUT     DX,AL           ;alphanumberic display #2 and ADC Muc select IF      BLINKER
        MOV     AL,[Blink]      ;Get blink timer
        INC     AL
        AND     AL,7FH          ;Extract mod 128 = 2.4 Hz
        MOV     [Blink],AL      ;Replace blinker
        MOV     DX,12000        ;Set AX for On
        CMP     AL,10H          ;Test for time to turn on
```

```
          JZ      PursOn
          CMP     AL,0              ;Test for time to turn off
          JNZ     SkpPurs           ;No - Skip
          MOV     DX,0              ;0000 (65536) for off
PursOn:   XCHG    AX,DX             ;Put intensity into AX
          MOV     DX,PURSUITLED     ;Pursuit LED port
          OUT     DX,AL
          MOV     AL,AH
          OUT     DX,AL
SkpPurs:
          ENDIF MOV     AL,20H            ;"Non-Specific End Of Interrupt"
          OUT     PORT20,AL         ;Reset 7th to high, 0 to low priority
          POP     DS
          POP     DX
          POP     CX                ;Restore registers
          POP     BX
          POP     AX
          IRET                      ;Continue from where interrupted
Interupt ENDP
;
; Convert character codes from BASIC and update matrix for "Interupt"
; processing. 0 - 9 encoded as 0 - 9; A - Z encoded as 10 - 36 plus Blank
          PUBLIC  Character
Character PROC FAR
          PUSH    BP
          MOV     BP,SP
          MOV     AX,DS
          MOV     ES,AX
          MOV     BX,[BP+8]         ;Get pointer to second BASIC argument
          MOV     AX,[BX]           ;Get argument into AL
          MOV     CX,7              ;Number of bytes per character in matrix
          MUL     CL                ;Compute offset to dot pattern array
          MOV     SI,AX             ;Prepare source pointer
          ADD     SI,OFFSET Char    ;Add base of character generator
          MOV     DI,OFFSET DSPLY1  ;Destination for "Interupt" routine
          REP     MOVSB             ;Copy character generator
          MOV     BX,[BP+6]         ;Get pointer to second BASIC argument
          MOV     AX,[BX]           ;Get argument into AL
          MOV     CX,7              ;Number of bytes per character in matrix
          MUL     CL                ;Compute offset to dot pattern array
          MOV     SI,AX             ;Prepare source pointer
          ADD     SI,OFFSET Char    ;Add base of character generator
          MOV     DI,OFFSET DSPLY2  ;Destination for "Interupt" routine
          REP     MOVSB             ;Copy character generator
          POP     BP                ;Restore registers
          RET     4                 ;Return; clear stack from two arguments
Character ENDP ; Motor control routine
; Transfer values from BASIC to timer control chips
          PUBLIC  Motorcontrol
MotorControl PROC
          PUSH    BP                ;Save register for BASIC
          MOV     BP,SP
          MOV     DX,PORT300        ;Prepare port address
          MOV     DI,[BP+6]         ;Get LAST (fifth) BASIC argument pointer
          MOV     AL,[DI]           ;Info dealing w/ Dirc+Plotting (CONTROL)
          OR      AL,4              ;Merge shift register reset bit.
          MOV     BX,AX
MC2:      IN      AL,DX
          AND     AL,10H            ;Wait for motor command in progress
          JZ      MC2
          MOV     AX,BX
          XOR     AL,OLDCONTROL     ;Old info dealing w/ Dirc+Plotting
          AND     AL,30H            ;See if solenoid setting different
```

```
              JZ      MC1                 ;See if it was turned off
              MOV     AX,BX               ;Establish new solenoid command
              OUT     DX,AL
              MOV     CX,0FFFFH           ;Settling time for solenoid to fall
MC3:          LOOP    MC3                 ;Long wait: 17*65535/8,000,000= 140 mSec
MC1:          MOV     OLDCONTROL,BL       ;save motor control info
              MOV     AX,BX
              OUT     DX,AL
              MOV     DI,[BP+14]          ;Get first BASIC argument pointer
              MOV     AX,[DI]             ;Get NumStepX& (only need 0-65535)
              MOV     DX,PORT308          ;X displacement counter
              OUT     DX,AL               ;Write value to timer
              MOV     AL,AH
              OUT     DX,AL
              MOV     DI,[BP+12]          ;Get second BASIC argument pointer
              MOV     AX,[DI]             ;Get NumStepY& (only need 0-65535)
              MOV     DX,PORT306          ;Y displacement counter
              OUT     DX,AL               ;Write value to timer
              MOV     AL,AH
              OUT     DX,AL
              MOV     DI,[BP+10]          ;Get third BASIC argument pointer
              MOV     AX,[DI]             ;Get StepRateX& (only need 0-65535)
              MOV     DX,PORT305
              OUT     DX,AL               ;Write value to timer
              MOV     AL,AH
              OUT     DX,AL
              MOV     DI,[BP+8]           ;Get fourth BASIC argument pointer
              MOV     AX,[DI]             ;Get StepRateY& (only need 0-65535)
              MOV     DX,PORT304
              OUT     DX,AL               ;Write value to timer
              MOV     AL,AH
              OUT     DX,AL
              CLI
              MOV     DX,PORT300
              IN      AL,DX               ;Get present status of motor circuit
              MOV     CL,AL
              MOV     AX,BX               ;Get solenoid, motor, bits
              OR      AL,8                ;Merge motor command strobe
              OUT     DX,AL
M4:           IN      AL,DX               ;Read status
              XOR     AL,CL               ;Wait for change in lsb (i.e. motor is done
              AND     AL,1                ;  with last move)
              JZ      M4
              MOV     AX,BX               ;Reload without bit 3
              OUT     DX,AL
              STI
              POP     BP                  ;Restore register for BASIC
              RET     10                  ;Return; Clear stack from 5 arguments
MotorControl  ENDP PUBLIC  SETTIMER            ;(for basic) sets the amount of time the
SETTIMER      PROC                        ;leds will be on for
              PUSH    BP                  ;Save register for BASIC
              MOV     BP,SP
              MOV     DI,[BP+6]           ;Get ONLY BASIC argument pointer
              MOV     AX,[DI]             ;Timer value for led on time.
              MOV     TIMER1,AX
              POP     BP                  ;Restore register for BASIC
              RET     2                   ;Return; Clear stack from 1 arguments
SETTIMER      ENDP PUBLIC  READTIMER           ;(for basic) read time left for led on time.
READTIMER     PROC
              MOV     AX,TIMER1           ;RETRIVE TIMER VALUE
              RET                         ;Return; Clear stack from 0 arguments
READTIMER     ENDP
```

```
        PUBLIC  TIME                    ;(for basic) read time OF DAY IN SEC
TIME    PROC                            ;(20 TIMES FASTER THEN TIMER BASIC)
        MOV     AX,TIMELOW              ;RETURN time of day in second * 300
        MOV     DX,TIMEHIGH             ;return 4-byte long word.
        RET                             ;Return; Clear stack from 0 arguments
TIME    ENDP PUBLIC  BUTTONS
BUTTONS PROC                            ;retrive buttons info
        PUSH    BP                      ;Save register for BASIC
        MOV     BP,SP
        MOV     AH,0
        MOV     AL,BUTTON
        MOV     DI,[BP+6]               ;Get ONLY  BASIC argument pointer
        MOV     BL,[DI]                 ;Button reset value
        AND     BL,1
        JNZ     NCLR
        MOV     BUTTON,BL
NCLR:   POP     BP                      ;Restore register for BASIC
        RET     2                       ;Return; Clear stack from 1 arguments
BUTTONS ENDP PUBLIC   LIGHTLEVEL             ;set led brightness (basic's interaction leds)
LIGHTLEVEL PROC
        PUSH    BP                      ;Save register for BASIC
        MOV     BP,SP
        MOV     DI,[BP+8]               ;Get FIRST  BASIC argument pointer
        MOV     DX,[DI]                 ;PORT value for led brightness control.
        MOV     DI,[BP+6]               ;Get second  BASIC argument pointer
        MOV     AX,[DI]                 ;brightness value for led brightness.
        MOV     BX,[DI+2]               ;LOAD HIGH ORDER BYTE (LONG INT)
        CMP     BX,0                    ;IF HIGH BYTE IS NOT ZERO THEN
        JE      LEDLVL                  ;long int is greater then 65535
        CMP     BX,0FFFFH               ;(COULD BE -1 TO -65534)
        JE      LEDLVL                  ;
        MOV     AX,1                    ;but largest # is 65536
LEDLVL: OUT     DX,AL                   ;give pulse width modulator led brightness
        MOV     AL,AH                   ;value.
        OUT     DX,AL
        POP     BP                      ;Restore register for BASIC
        RET     4                       ;Return; Clear stack from 2 arguments
LIGHTLEVEL ENDP PUBLIC   GETADC
GETADC  PROC
        PUSH    BP                      ;Save register for BASIC
        MOV     BP,SP
        MOV     BX,[BP+12]              ;Get first  BASIC argument pointer
        MOV     AX,[BX]                 ;adc input channel
        MOV     CL,5
        SHL     AL,CL                   ;Shift to bits (5,6,7).
        MOV     Chanel,AL               ;SAVE MUX INFO (so interupt does not change it)
        MOV     DX,PORT302              ;Select mux gate port
        OUT     DX,AL                   ;Select mux gate.
        MOV     BX,[BP+10]              ;Get second  BASIC argument pointer
        MOV     CX,[BX]                 ;# of samples to take
        MOV     BX,[BP+8]               ;Get THIRD  BASIC argument
        MOV     AX,[BX]                 ;(ARRAY) SEG OFFSET
        MOV     ES,AX                   ;Extra segment point to array SEG offset
        MOV     BX,[BP+6]               ;Get FOURTH basic ARG (ARRAY) offset.
        MOV     AX,[BX]
        MOV     BX,AX
GETNUM: MOV     DX,PORT300              ;BIT 3 OF PORT 300 IS ADC END OF CONVERSION
LP1:    IN      AL,DX                   ;look at EOC bit, if low then conversion
        AND     AX,8                    ;is not done, so loop until EOC is high (done)
        JZ      LP1
        MOV     DX,PORT314              ;strobe ADC (start next conversion)
        OUT     DX,AL                   ;Data does not matter.
```

```
        MOV     DX,PORT303          ;port 303 is ADC data port
        IN      AL,DX               ;load last conversion data.
        MOV     ES:[BX],AX          ;store data in BASIC ARRAY.
        ADD     BX,2                ;point to next element in array
        LOOP    GETNUM              ;loop until CX # of samples have been taken
        POP     BP                  ;Restore register for BASIC
        RET     8                   ;Return; Clear stack from 4 arguments
GETADC  ENDP PUBLIC  COMPARRAY
COMPARRAY PROC
        PUSH    BP                  ;Save register for BASIC
        MOV     BP,SP
        MOV     BX,[BP+16]          ;Get FIRST BASIC argument pointer
        MOV     CX,[BX]             ;NUMBER OF ELEMENTS
        MOV     ELEMENTS,CX
        MOV     BX,[BP+14]          ;Get SECOND BASIC argument pointer
        MOV     CX,[BX]             ;X& NUMBER TO COMPARE AGAINST
        MOV     BX,[BP+12]          ;Get THIRD BASIC argument pointer
        MOV     DX,[BX]             ;Y& NUMBER TO COMPARE AGAINST
        MOV     BX,[BP+10]          ;Get FOURTH BASIC argument pointer
        MOV     AX,[BX]             ;WITHIN THIS "ERROR"
        SUB     CX,AX
        MOV     POSX1,CX            ;POSITION X-ERROR
        ADD     CX,AX
        ADD     CX,AX
        MOV     POSX2,CX            ;POSITION X+ERROR
        SUB     DX,AX
        MOV     POSY1,DX            ;POSITION Y-ERROR
        ADD     DX,AX
        ADD     DX,AX
        MOV     POSY2,DX            ;POSITION Y+ERROR
        MOV     BX,[BP+8]           ;Get FIFTH BASIC argument
        MOV     AX,[BX]             ;(ARRAY) SEG OFFSET
        MOV     ES,AX               ;Extra segment point to array SEG offset
        MOV     BX,[BP+6]           ;Get SIXTH basic ARG (ARRAY) offset.
        MOV     DI,[BX]             ;POINTS TO ARRAY OFFSET WITHIN EXTRASEGMENT
        MOV     INDEX,DI
        MOV     AX,0
        MOV     NUMMATCHES,AX
        MOV     CX,64
        REP     STOSW               ;CLEAR THE FIRST 16 LONGWORD ENTRIES (LONGINT)
        MOV     BX,[BP+16]          ;Get FIRST BASIC argument pointer
        MOV     CX,[BX]             ;NUMBER OF ELEMENTS
        MOV     ELEMENTS,CX
        MOV     BX,DI
        MOV     DX,POSX1            ;FASTER TO USE DX INSTEAD OF POSX1
COMP:   MOV     AX,ES:[BX]          ;LOAD X COORDINATE
        ADD     BX,4                ;POINT TO POSY
        CMP     AX,DX               ;COMPARE TO LOWER BOUND
        JL      NEXT                ;NOT WITHIN ERROR
        CMP     AX,POSX2            ;COMPARE UPPER BOUND
        JG      NEXT                ;NOT WITHIN ERROR
        MOV     AX,ES:[BX]          ;LOAD Y COORDINATE
        CMP     AX,POSY1            ;COMPARE TO LOWER BOUND
        JL      NEXT                ;NOT WITHIN ERROR
        CMP     AX,POSY2            ;COMPARE UPPER BOUND
        JG      NEXT                ;NOT WITHIN ERROR
        MOV     AX,ELEMENTS         ;NUMBER OF ELEMENTS
        SUB     AX,CX               ;LOAD ELEMENT NUMBER
        PUSH    CX
        MOV     CX,16
        DIV     CL
        MOV     CL,AH
        MOV     AH,0
        INC     AL
        MOV     DI,INDEX
        STOSW                       ;SAVE ELEMENT # IN ARRAY
        ADD     DI,2
```

```
                MOV     AX,CX
                STOSW
                POP     CX
                ADD     INDEX,8
                INC     NUMMATCHES
                CMP     NUMMATCHES,16
                JGE     EDCOMP
NEXT:           ADD     BX,4                    ;POINT TO POSX
                LOOP    COMP
EDCOMP:  MOV    AX,NUMMATCHES           ;RETURN NON ZERO IF MATCH
                POP     BP                      ;Restore register for BASIC
                RET     12                      ;Return; Clear stack from 6 arguments
COMPARRAY       ENDP PUBLIC  CLOSELEMENT
CLOSELEMENT     PROC
                PUSH    BP                      ;Save register for BASIC
                MOV     BP,SP
                MOV     BX,[BP+6]               ;get the last basic argument pointer
                MOV     DX,[BX]                 ;min distance to target (allowable)
                MOV     MIN,DX
                MOV     BX,[BP+18]              ;Get first BASIC argument pointer
                MOV     DX,[BX]                 ;X& NUMBER TO COMPARE AGIANST
                MOV     POSX1,DX
                MOV     BX,[BP+16]              ;Get SECOND BASIC argument pointer
                MOV     DX,[BX]                 ;Y& NUMBER TO COMPARE AGIANST
                MOV     POSY1,DX
                MOV     BX,[BP+8]               ;Get SIXTH basic ARG (ARRAY) offset.
                MOV     DX,[BX]                 ;POINTS TO ARRAY OFFSET WITHIN EXTRASEGMENT
                MOV     INDEX,DX
                MOV     BX,[BP+12]              ;Get FOURTH basic ARG (ARRAY) offset.
                MOV     DI,[BX]                 ;POINTS TO ARRAY OFFSET WITHIN EXTRASEGMENT
                MOV     ELEMENTS,0
                MOV     TEMP3,8000H
                MOV     TEMP4,8000H
                MOV     CX,99                   ;NUMBER OF TEST PTS
                MOV     BX,[BP+14]              ;Get THIRD BASIC argument
                MOV     AX,[BX]                 ;(ARRAY) SEG OFFSET
                MOV     ES,AX                   ;Extra segment point to array SEG offset
MORE:    MOV    AX,100
                SCASB                           ;SCAN PTSAW% ARRAY FOR MISSED PTS
                JBE     NOTHERE
                CALL    INNERLOOP
NOTHERE: ADD    DI,3
                LOOP    MORE
                MOV     AX,POSX2
                MOV     BX,[BP+18]              ;Get      BASIC argument pointer
                MOV     [BX],AX                 ;X&       TO COMPARE AGIANST
                MOV     AX,POSY2
                MOV     BX,[BP+16]              ;Get      BASIC argument pointer
                MOV     [BX],AX                 ;Y&       TO COMPARE AGIANST
                MOV     AX,ELEMENTS             ;RETURN   ZERO IF MATCH(ELEMENT # MATCH)
                POP     BP                      ;Restore register for BASIC
                RET     14                      ;Return; Clear stack from 7 arguments INNERLOOP       PROC    NEAR                    ;INNER LOOP
                PUSH    CX                      ;THE     PROCEDURE SCANS THE FIRST ARRAY
                PUSH    ES                      ;LOOKING FOR MISSED OR NOT TESTED PTS
                MOV     AX,100                  ;THIS    PROCEDURE THEN DETERMINES THE LENGTH
                SUB     AX,CX                   ;TO THE  CLOSEST PT TO TEST THAT PT, IF THE
                MOV     CX,AX                   ;LENGTH  IS LESS THEN ANY PREVIOUS THEN SAVE IT
                MOV     TEMP,CX
                MOV     BX,[BP+10]              ;Get     BASIC argument
                MOV     AX,[BX]                 ;(ARRAY) SEG OFFSET
                MOV     ES,AX                   ;Extra segment point to array SEG offset
```

```
            MOV     AX,128          ;16 ELEMENTS * 4 BYTES(LONGINT) * 2 (X,Y)
            MUL     CL
            ADD     AX,INDEX
            MOV     BX,AX           ;OFFSET OF ARRAY ELEMENT
            MOV     CX,16
NEXT2:      MOV     TEMP2,0
            MOV     AX,ES:[BX]
            ADD     BX,4            ;4 BYTE LONG INTEGER (ONLY USE 16 BITS 65535)
            CMP     AX,0
            JE      NEXTONE
            MOV     DX,POSX1
            CALL    DIFFERANCE
            MOV     TEMP1,AX
            MOV     AX,ES:[BX]
            CMP     AX,0
            JE      NEXTONE
            MOV     DX,POSY1
            CALL    DIFFERANCE
            ADD     AX,TEMP1
            MOV     SI,AX
            MOV     DX,0
            ADC     DX,0            ;SAVE OVERFLOW
            MOV     TEMP2,DX
            SUB     AX,TEMP3        ;COMPARE TO PREVIOUSLY SMALLEST LENGTH
            SBB     DX,TEMP4
            JNC     NEXTONE
            MOV     AX,SI
            SUB     AX,MIN          ;IF LESS THEN COMPARE TO MIN DISTANCE
            MOV     DX,TEMP2
            SBB     DX,0
            JC      NEXTONE
            MOV     TEMP3,SI        ;IF MORE THEN MIN THEN SAVE THIS PT
            MOV     AX,TEMP2
            MOV     TEMP4,AX
            MOV     AX,ES:[BX]
            MOV     POSY2,AX
            MOV     AX,ES:[BX-4]
            MOV     POSX2,AX
            MOV     SI,INDEX
            MOV     AL,16
            SUB     AL,CL
            MOV     ES:[SI],AL
            MOV     AX,TEMP
            MOV     ELEMENTS,AX
NEXTONE:    ADD     BX,4
            LOOP    NEXT2
            POP     ES
            POP     CX
            RET
INNERLOOP           ENDP

DIFFERANCE          PROC    NEAR    ;FIND THE DIFFERENCE BETWEEN TWO
            CMP     AX,DX           ;NUMBERS AND ALWAYS RETURN A
            JC      POS1            ;POSSITIVE VALUE
            SUB     AX,DX           ;ABS(X - X1)
            RET
POS1:       SUB     DX,AX
            MOV     AX,DX
            RET
DIFFERANCE          ENDP
CLOSELEMENT         ENDP
            END
```

APPENDIX 2

```
!=========================================================================!
!                                                                         !
!           Software for the TKS-4000 auto perimeter.                     !
!                                                                         !
!           VISMED INC                                                    !
!           9040 Carroll Way, Suite 2                                     !
!           San Diego, CA  92121                                          !
!                                                                         !
!           Written By:                                                   !
!                                                                         !
!                   Vincent Brancaccio                                    !
!                                                                         !
!=========================================================================!

DECLARE SUB Initial ()                                  'assembly-language routine
DECLARE FUNCTION Time& ()                               'assembly-language routine
DECLARE FUNCTION Subtract& (A&, B&)                     'assembly-language routine
DECLARE FUNCTION Buttons% (A%)                          'assembly-language routine
DECLARE FUNCTION CompArray% (ELEMENTS%, X&, Y&, ER%, A%, B%) 'ASSEMBLY-LANGUAGE
DECLARE FUNCTION ClosElement% (X&, Y&, B%, C%, D%, E%, F%) 'ASSEMBLY-LANGUAGE
DECLARE SUB LightLevel (A%, B%)                         'assembly-language routine
DECLARE SUB SetTimer (A%)                               'assembly-language routine
DECLARE FUNCTION ReadTimer% ()                          'assembly-language routine
DECLARE SUB GetAdc (A%, B%, C%, D%)                     'assembly-language routine
DECLARE SUB Character (A%, B%)                          'assembly-language routine
DECLARE SUB MotorControl (A&, B&, C&, D&, E%)           'assembly-language routine
DECLARE FUNCTION Acos! (Arg!)
DECLARE FUNCTION HillOfVision% (X&, Y&)
DECLARE FUNCTION NormalizeHill% (ThH%())
DECLARE SUB HomePosition ()
DECLARE SUB PositionControl (Xpos&, Ypos&, Speed%, Control%)
DECLARE SUB PlotTest ()
DECLARE SUB Calculate2 (X&, Y&, Ang1!, Ang2!)
DECLARE SUB Diagnostics ()
DECLARE SUB TestPts ()
DECLARE SUB TestMissedPts (X&, Y&)
DECLARE SUB BlindSpotTest (X&, Y&)
DECLARE SUB SelectEye ()
DECLARE SUB TargetLeds (LedOnTime%)
DECLARE FUNCTION Length! (X!, Y!)
DECLARE SUB RampUp (Xpos&, Ypos&, Speed%, Control%)
DECLARE SUB RelativeMove (X&, Y&, Speed%, Control%)
DECLARE SUB TurnAround (X&, Y&, StepSizeX%, StepSizeY%, Speed%)
DECLARE SUB DefineBlindSpot (X&, Y&, Speed%, BRIGHT%)
DECLARE SUB RadialMove (X&, Y&, I%, Speed%, BRIGHT%)
DECLARE SUB Calculate1 (X&, Y&, Ang1!, Ang2!, Tim&, Light%)
DECLARE SUB Square (X&, Y&, Speed%)
DECLARE FUNCTION Button% (Bclr%)
DECLARE SUB DisplayResults ()
DECLARE SUB Move2andLed (X&, Y&, X1&, Y1&, Speed%, Led%, Index%)
DECLARE SUB MovelandLed (X&, Y&, Speed%, Control%)

CONST PIE = 3.141593
CONST Pie2 = 2 * PIE
CONST LedOFF = 0                    'led off number
CONST MaxOnTime = 0     'max time the leds come be on (about 3 min)
CONST XP = 54600        'Max number of micro-steps along X-axis.
CONST YP = 46000        'Max number of micro-steps along Y-axis.
CONST Xcen = XP / 2     'Center of X axis.
CONST Ycen = YP / 2     'Center of Y axis.
CONST GroupA = &H30C    'ports for groups of leds
CONST GroupB = &H30D
CONST GroupC = &H30E
CONST GroupD = &H310
```

```
CONST LedSelect = &H301  'port that selects which led of each group is to be on
CONST MotorPort = &H300           'motor contrl port
CONST Pursuit = &H30A    'port for pursuit led.
CONST PBright = 20   'brightness of pursuit led (at center screen)
CONST ScreenWidth = (.5 * PIE) * XP / 3200 '(CAPSTAN DIA)*(TOTAL STEPS) / (STEPS
IN 1 REV)
CONST Pdistance = (14.2 / ScreenWidth) * XP
CONST Pdistance2 = Pdistance * Pdistance
CONST Inch5 = (5 / ScreenWidth) * XP       'INCH5 REPRESENTS 5 INCHES IN STEPS
CONST Inch10 = (10 / ScreenWidth) * XP     'MAX MOTION IS 26.5 INCHES IN X-AXIS
CONST Inch15 = (15 / ScreenWidth) * XP
CONST Pie180 = PIE / 180

DIM SHARED BlindTim&(1, 8)         'patient response time (BLIND SPOT TEST)
DIM SHARED BlindR1!(1, 8)          'radial coordinate of start of stimulus segment.
DIM SHARED BlindD1!(1, 8)          'angular coordinate of start of stimulus segment.
DIM SHARED BlindR2!(1, 8)          'radial coordinate of end of stimulus segment.
DIM SHARED BlindD2!(1, 8)          'angular coordinate of end of stimulus segment.
DIM SHARED LightPosX&(16)          'X coordinate of each fixed light stimulis.
DIM SHARED LightPosY&(16)          'Y coordinate of each fixed light stimulis.
DIM SHARED Length2&(16)            'THE LENGTH FROM THE CENTER OF THE SCREEN SQUARED
DIM SHARED Length1&(16)            'THE LENGTH FROM THE CENTER OF THE SCREEN
DIM SHARED RelativeI&(4, 4)        'Relative light intensity (relative to center)
DIM SHARED UnitLog&(-10 TO 40)     '-10 TO 0 ARE ALL 0 (WILL WILL NOT CAUSE ERR)
DIM SHARED BRIGHT%(99)        'BRIGHTNESS OF TARGET LEDS IN DB
DIM SHARED Tim&(1, 99)        'PATIANTS REATION TIME  (99 PT TEST)
DIM SHARED PtSaw%(1, 99)      'PERCENTAGE SEEN (100=HE SAW IT,1-DID NOT SEE IT)
DIM SHARED PossibleS&(1 TO 2, 1600)
DIM SHARED Pt(2, 100)              'angular position of test pts.
DIM SHARED LeftAC%(3)              'all leds have a mirror (led) about the y-axias
DIM SHARED LeftBD%(3)              'these two arrays contain the mirror led #
DIM SHARED Group%(3)
DIM SHARED Brt%(3)
DIM SHARED Hill&(3, 19)

COMMON SHARED LastX&          'last commanded position of X-axis stepper motor.
COMMON SHARED LastY&          'last commanded position of Y-axis stepper motor.
COMMON SHARED Eye%            'Eye%=0-right eye,Eye%=1-left eye, Eye%=3-plotting '=================================================================
'
'              . Begining Main Module
'
'================================================================= begin:
    CLEAR                                    'clear all variables
                    'leds (x,y) positions.
    LightPosX&(0) = Xcen                     'position of each led.
    LightPosY&(0) = Ycen
    LightPosX&(1) = Xcen
    LightPosY&(1) = Ycen - Inch10
    LightPosX&(2) = Xcen + Inch15 * SIN(30 * Pie180)
    LightPosY&(2) = Ycen - Inch15 * COS(30 * Pie180)
    LightPosX&(3) = Xcen - Inch15 * SIN(30 * Pie180)
    LightPosY&(3) = Ycen - Inch15 * COS(30 * Pie180)
    LightPosX&(4) = Xcen - Inch5 * COS(30 * Pie180)
    LightPosY&(4) = Ycen - Inch5 * SIN(30 * Pie180)
    LightPosX&(5) = Xcen - Inch10 * COS(30 * Pie180)
    LightPosY&(5) = Ycen - Inch10 * SIN(30 * Pie180)
    LightPosX&(6) = Xcen - Inch15
    LightPosY&(6) = Ycen
    LightPosX&(7) = Xcen - Inch10 * COS(30 * Pie180)
    LightPosY&(7) = Ycen + Inch10 * SIN(30 * Pie180)
    LightPosX&(8) = Xcen
    LightPosY&(8) = Ycen + Inch5
    LightPosX&(9) = Xcen
    LightPosY&(9) = Ycen + Inch10
```

```
LightPosX&(10) = Xcen - Inch15 * SIN(30 * Pie180)
LightPosY&(10) = Ycen + Inch15 * COS(30 * Pie180)
LightPosX&(11) = Xcen + Inch15 * SIN(30 * Pie180)
LightPosY&(11) = Ycen + Inch15 * COS(30 * Pie180)
LightPosX&(12) = Xcen + Inch10 * COS(30 * Pie180)
LightPosY&(12) = Ycen + Inch10 * SIN(30 * Pie180)
LightPosX&(13) = Xcen + Inch15
LightPosY&(13) = Ycen
LightPosX&(14) = Xcen + Inch10 * COS(30 * Pie180)
LightPosY&(14) = Ycen - Inch10 * SIN(30 * Pie180)
LightPosX&(15) = Xcen + Inch5 * COS(30 * Pie180)
LightPosY&(15) = Ycen - Inch5 * SIN(30 * Pie180)
LeftAC%(0) = 0         'LEFT EYE TARGET LEDS RELATIVE TO RIGHT EYE
LeftAC%(1) = 1         'LEFTAC IS READ LEFT EYE A RELATIVE TO C
LeftAC%(2) = 3         'AND C RELATIVE TO A (GROUPS)
LeftAC%(3) = 2
LeftBD%(0) = 3
LeftBD%(1) = 2
LeftBD%(2) = 1
LeftBD%(3) = 0

FOR I% = 0 TO 15        'SET THE DISTANCE FROM THE CENTER OF SCREEN
    Length2&(I%) = Length((LightPosX&(I%) - Xcen), LightPosY&(I%) - Ycen)
    Length1&(I%) = SQR(Length2&(I%))
NEXT
    'relative (TO CENTER LED) brightnes of each led to patient's eye
    'integers * 1000 (.005 is 5) is quicker for targetleds procedure
FOR I% = 0 TO 3
RelativeI&(1, I%) = 1000 * ((Pdistance / SQR(Pdistance2 + Length2&(I%))) ^ 4)
RelativeI&(2, I%) = 1000 * ((Pdistance / SQR(Pdistance2 + Length2&(4 + I%))) ^ 4)
RelativeI&(3, I%) = 1000 * ((Pdistance / SQR(Pdistance2 + Length2&(8 + I%))) ^ 4)
RelativeI&(4, I%) = 1000 * ((Pdistance / SQR(Pdistance2 + Length2&(12 + I%))) ^ 4)
NEXT
FOR I% = 1 TO 40
UnitLog&(41 - I%) = 12589 * (10 ^ (I% / 10))
NEXT
OPEN "DATA.TST" FOR RANDOM AS #1 LEN = 4
Temp% = 16
FOR I% = 1 TO 3168 STEP 2
GET #1, I%, PossibleS&(1, Temp%)
GET #1, I% + 1, PossibleS&(2, Temp%)
Temp% = Temp% - 1
NEXT
CLOSE
FOR I% = 1 TO 8
    BRIGHT%(I%) = 29.5      '5 DEGREE BRIGHTNESS IN DB
NEXT
FOR I% = 9 TO 20
    BRIGHT%(I%) = 27        '10 DEGREE BRIGHTNESS IN DB
NEXT
FOR I% = 21 TO 38
    BRIGHT%(I%) = 25.5      '15 DEGREE BRIGHTNESS IN DB
NEXT
FOR I% = 39 TO 52
    BRIGHT%(I%) = 24        '20 DEGREE BRIGHTNESS IN DB
NEXT
FOR I% = 53 TO 54
    BRIGHT%(I%) = 22.5      '25 DEGREE BRIGHTNESS IN DB
NEXT
FOR I% = 55 TO 64
    BRIGHT%(I%) = 21        '30 DEGREE BRIGHTNESS IN DB
NEXT
FOR I% = 65 TO 76
    BRIGHT%(I%) = 18        '40 DEGREE BRIGHTNESS IN DB
```

```
         NEXT
         FOR I% = 77 TO 78
            BRIGHT%(I%) = 16.5         '45 DEGREE BRIGHTNESS IN DB
         NEXT
         FOR I% = 79 TO 82
            BRIGHT%(I%) = 15           '50 DEGREE BRIGHTNESS IN DB
         NEXT
         FOR I% = 83 TO 84
            BRIGHT%(I%) = 13.5         '55 DEGREE BRIGHTNESS IN DB
         NEXT
         FOR I% = 85 TO 91
            BRIGHT%(I%) = 12           '60 DEGREE BRIGHTNESS IN DB
         NEXT
         FOR I% = 92 TO 93
            BRIGHT%(I%) = 9            '70 DEGREE BRIGHTNESS IN DB
         NEXT
         FOR I% = 94 TO 99
            BRIGHT%(I%) = 6            '80 DEGREE BRIGHTNESS IN DB
         NEXT
         FOR I% = 1 TO 99     'max brightness (BRYAN YOU CAN REMOVE THIS LOOP)
            BRIGHT%(I%) = 11           'MAX BRIGHTNESS FOR ALL LEDS
         NEXT 'HILL OF VISION TEST PTS.
         Hill&(0, 0) = 20654: Hill&(1, 0) = 16354: Hill&(2, 0) = 0: Hill&(3, 0) = 1
         Hill&(0, 1) = 19525: Hill&(1, 1) = 10403: Hill&(2, 1) = 1: Hill&(3, 1) = 4
         Hill&(0, 2) = 22309: Hill&(1, 2) = 6824: Hill&(2, 2) = 3: Hill&(3, 2) = 3
         Hill&(0, 3) = 25358: Hill&(1, 3) = 11028: Hill&(2, 3) = 4: Hill&(3, 3) = 2
         Hill&(0, 4) = 29242: Hill&(1, 4) = 11028: Hill&(2, 4) = 15: Hill&(3, 4) = 1
         Hill&(0, 5) = 32291: Hill&(1, 5) = 6824: Hill&(2, 5) = 2: Hill&(3, 5) = 4
         Hill&(0, 6) = 35075: Hill&(1, 6) = 10403: Hill&(2, 6) = 1: Hill&(3, 6) = 3
         Hill&(0, 7) = 33946: Hill&(1, 7) = 16354: Hill&(2, 7) = 0: Hill&(3, 7) = 2
         Hill&(0, 8) = 36907: Hill&(1, 8) = 20850: Hill&(2, 8) = 14: Hill&(3, 8) = 4
         Hill&(0, 9) = 36907: Hill&(1, 9) = 25150: Hill&(2, 9) = 12: Hill&(3, 9) = 1
         Hill&(0, 10) = 33946: Hill&(1, 10) = 29646: Hill&(2, 10) = 0: Hill&(3, 10) = 3
         Hill&(0, 11) = 35075: Hill&(1, 11) = 35597: Hill&(2, 11) = 9: Hill&(3, 11) = 2
         Hill&(0, 12) = 32291: Hill&(1, 12) = 39176: Hill&(2, 12) = 11: Hill&(3, 12) = 1
         Hill&(0, 13) = 22309: Hill&(1, 13) = 39176: Hill&(2, 13) = 10: Hill&(3, 13) = 2
         Hill&(0, 14) = 19525: Hill&(1, 14) = 35597: Hill&(2, 14) = 9: Hill&(3, 14) = 1
         Hill&(0, 15) = 20654: Hill&(1, 15) = 29646: Hill&(2, 15) = 0: Hill&(3, 15) = 4
         Hill&(0, 16) = 17693: Hill&(1, 16) = 25150: Hill&(2, 16) = 7: Hill&(3, 16) = 2
         Hill&(0, 17) = 17693: Hill&(1, 17) = 20850: Hill&(2, 17) = 5: Hill&(3, 17) = 3
         Hill&(0, 18) = Xcen + 5000: Hill&(1, 18) = Ycen
         Hill&(0, 19) = Xcen: Hill&(1, 19) = Ycen '90 PT TEST POINTS.
         Pt(1, 1) = 5 * Pie180: Pt(2, 1) = 160 * Pie180
         Pt(1, 2) = 5 * Pie180: Pt(2, 2) = 120 * Pie180
         Pt(1, 3) = 5 * Pie180: Pt(2, 3) = 70 * Pie180
         Pt(1, 4) = 5 * Pie180: Pt(2, 4) = 20 * Pie180
         Pt(1, 5) = 5 * Pie180: Pt(2, 5) = 340 * Pie180
         Pt(1, 6) = 5 * Pie180: Pt(2, 6) = 290 * Pie180
         Pt(1, 7) = 5 * Pie180: Pt(2, 7) = 250 * Pie180
         Pt(1, 8) = 5 * Pie180: Pt(2, 8) = 200 * Pie180
         Pt(1, 9) = 10 * Pie180: Pt(2, 9) = 165 * Pie180
         Pt(1, 10) = 10 * Pie180: Pt(2, 10) = 130 * Pie180
         Pt(1, 11) = 10 * Pie180: Pt(2, 11) = 105 * Pie180
         Pt(1, 12) = 10 * Pie180: Pt(2, 12) = 75 * Pie180
         Pt(1, 13) = 10 * Pie180: Pt(2, 13) = 45 * Pie180
         Pt(1, 14) = 10 * Pie180: Pt(2, 14) = 15 * Pie180
         Pt(1, 15) = 10 * Pie180: Pt(2, 15) = 345 * Pie180
         Pt(1, 16) = 10 * Pie180: Pt(2, 16) = 315 * Pie180
         Pt(1, 17) = 10 * Pie180: Pt(2, 17) = 285 * Pie180
         Pt(1, 18) = 10 * Pie180: Pt(2, 18) = 255 * Pie180
         Pt(1, 19) = 10 * Pie180: Pt(2, 19) = 225 * Pie180
         Pt(1, 20) = 10 * Pie180: Pt(2, 20) = 195 * Pie180
         Pt(1, 21) = 15 * Pie180: Pt(2, 21) = 170 * Pie180
```

```
Pt(1, 22) = 15 * Pie180: Pt(2, 22) = 150 * Pie180
Pt(1, 23) = 15 * Pie180: Pt(2, 23) = 135 * Pie180
Pt(1, 24) = 15 * Pie180: Pt(2, 24) = 120 * Pie180
Pt(1, 25) = 15 * Pie180: Pt(2, 25) = 100 * Pie180
Pt(1, 26) = 15 * Pie180: Pt(2, 26) = 80 * Pie180
Pt(1, 27) = 15 * Pie180: Pt(2, 27) = 60 * Pie180
Pt(1, 28) = 15 * Pie180: Pt(2, 28) = 45 * Pie180
Pt(1, 29) = 15 * Pie180: Pt(2, 29) = 30 * Pie180
Pt(1, 30) = 15 * Pie180: Pt(2, 30) = 330 * Pie180
Pt(1, 31) = 15 * Pie180: Pt(2, 31) = 315 * Pie180
Pt(1, 32) = 15 * Pie180: Pt(2, 32) = 300 * Pie180
Pt(1, 33) = 15 * Pie180: Pt(2, 33) = 280 * Pie180
Pt(1, 34) = 15 * Pie180: Pt(2, 34) = 260 * Pie180
Pt(1, 35) = 15 * Pie180: Pt(2, 35) = 240 * Pie180
Pt(1, 36) = 15 * Pie180: Pt(2, 36) = 225 * Pie180
Pt(1, 37) = 15 * Pie180: Pt(2, 37) = 210 * Pie180
Pt(1, 38) = 15 * Pie180: Pt(2, 38) = 190 * Pie180
Pt(1, 39) = 20 * Pie180: Pt(2, 39) = 170 * Pie180
Pt(1, 40) = 20 * Pie180: Pt(2, 40) = 150 * Pie180
Pt(1, 41) = 20 * Pie180: Pt(2, 41) = 120 * Pie180
Pt(1, 42) = 20 * Pie180: Pt(2, 42) = 100 * Pie180
Pt(1, 43) = 20 * Pie180: Pt(2, 43) = 80 * Pie180
Pt(1, 44) = 20 * Pie180: Pt(2, 44) = 60 * Pie180
Pt(1, 45) = 20 * Pie180: Pt(2, 45) = 30 * Pie180
Pt(1, 46) = 20 * Pie180: Pt(2, 46) = 330 * Pie180
Pt(1, 47) = 20 * Pie180: Pt(2, 47) = 300 * Pie180
Pt(1, 48) = 20 * Pie180: Pt(2, 48) = 280 * Pie180
Pt(1, 49) = 20 * Pie180: Pt(2, 49) = 260 * Pie180
Pt(1, 50) = 20 * Pie180: Pt(2, 50) = 240 * Pie180
Pt(1, 51) = 20 * Pie180: Pt(2, 51) = 210 * Pie180
Pt(1, 52) = 20 * Pie180: Pt(2, 52) = 190 * Pie180
Pt(1, 53) = 25 * Pie180: Pt(2, 53) = 15 * Pie180
Pt(1, 54) = 25 * Pie180: Pt(2, 54) = 345 * Pie180
Pt(1, 55) = 30 * Pie180: Pt(2, 55) = 170 * Pie180
Pt(1, 56) = 30 * Pie180: Pt(2, 56) = 135 * Pie180
Pt(1, 57) = 30 * Pie180: Pt(2, 57) = 100 * Pie180
Pt(1, 58) = 30 * Pie180: Pt(2, 58) = 80 * Pie180
Pt(1, 59) = 30 * Pie180: Pt(2, 59) = 45 * Pie180
Pt(1, 60) = 30 * Pie180: Pt(2, 60) = 315 * Pie180
Pt(1, 61) = 30 * Pie180: Pt(2, 61) = 280 * Pie180
Pt(1, 62) = 30 * Pie180: Pt(2, 62) = 260 * Pie180
Pt(1, 63) = 30 * Pie180: Pt(2, 63) = 225 * Pie180
Pt(1, 64) = 30 * Pie180: Pt(2, 64) = 190 * Pie180
Pt(1, 65) = 40 * Pie180: Pt(2, 65) = 135 * Pie180
Pt(1, 66) = 40 * Pie180: Pt(2, 66) = 100 * Pie180
Pt(1, 67) = 40 * Pie180: Pt(2, 67) = 80 * Pie180
Pt(1, 68) = 40 * Pie180: Pt(2, 68) = 45 * Pie180
Pt(1, 69) = 40 * Pie180: Pt(2, 69) = 15 * Pie180
Pt(1, 70) = 40 * Pie180: Pt(2, 70) = 5 * Pie180
Pt(1, 71) = 40 * Pie180: Pt(2, 71) = 355 * Pie180
Pt(1, 72) = 40 * Pie180: Pt(2, 72) = 345 * Pie180
Pt(1, 73) = 40 * Pie180: Pt(2, 73) = 315 * Pie180
Pt(1, 74) = 40 * Pie180: Pt(2, 74) = 280 * Pie180
Pt(1, 75) = 40 * Pie180: Pt(2, 75) = 260 * Pie180
Pt(1, 76) = 40 * Pie180: Pt(2, 76) = 225 * Pie180
Pt(1, 77) = 45 * Pie180: Pt(2, 77) = 170 * Pie180
Pt(1, 78) = 45 * Pie180: Pt(2, 78) = 190 * Pie180
Pt(1, 79) = 50 * Pie180: Pt(2, 79) = 30 * Pie180
Pt(1, 80) = 50 * Pie180: Pt(2, 80) = 10 * Pie180
Pt(1, 81) = 50 * Pie180: Pt(2, 81) = 350 * Pie180
Pt(1, 82) = 50 * Pie180: Pt(2, 82) = 340 * Pie180
Pt(1, 83) = 55 * Pie180: Pt(2, 83) = 100 * Pie180
Pt(1, 84) = 55 * Pie180: Pt(2, 84) = 80 * Pie180
Pt(1, 85) = 60 * Pie180: Pt(2, 85) = 170 * Pie180
Pt(1, 86) = 60 * Pie180: Pt(2, 86) = 15 * Pie180
Pt(1, 87) = 60 * Pie180: Pt(2, 87) = 5 * Pie180
Pt(1, 88) = 60 * Pie180: Pt(2, 88) = 355 * Pie180
Pt(1, 89) = 60 * Pie180: Pt(2, 89) = 345 * Pie180
```

```
    Pt(1, 90) = 60 * Piel80: Pt(2, 90) = 315 * Piel80
    Pt(1, 91) = 60 * Piel80: Pt(2, 91) = 190 * Piel80
    Pt(1, 92) = 70 * Piel80: Pt(2, 92) = 5 * Piel80
    Pt(1, 93) = 70 * Piel80: Pt(2, 93) = 355 * Piel80
    Pt(1, 94) = 80 * Piel80: Pt(2, 94) = 20 * Piel80
    Pt(1, 95) = 80 * Piel80: Pt(2, 95) = 10 * Piel80
    Pt(1, 96) = 80 * Piel80: Pt(2, 96) = 5 * Piel80
    Pt(1, 97) = 80 * Piel80: Pt(2, 97) = 355 * Piel80
    Pt(1, 98) = 80 * Piel80: Pt(2, 98) = 350 * Piel80
    Pt(1, 99) = 80 * Piel80: Pt(2, 99) = 340 * Piel80

Initial                  'INITIALIZE THE INTERUPT ROUTINE AND 8253'S
    Diagnostics              'Determine if machine is working correctly.
    HomePosition
'=====================================================================
'
'                        Begining test
'
'=====================================================================
'
DO
    SelectEye                            'wait for operator responce.
    IF Eye% = 3 THEN GOTO EndTest         'skip test left eye.
    Hill% = 0                            'WE DON'T KNOW WHERE HER HILL IS
    ' BlindSpotTest X&, Y&                '(8pt) find and define blind spot.
    Hill% = HillOfVision(X&, Y&)          '(8pt) find patients hill of vision.
    LOCATE 1, 1: PRINT "HILL OF VISION "; 25 - Hill%; "DB... DEVIATION "; Hill%; "
DB"
    ' TestPts                             'test # of pts. (80)
    Eye% = Eye% XOR 1
LOOP WHILE Eye% = 1
EndTest:
    Character 25, 21
    PlotTest
    GOTO begin
END '=====================================================================
'
'       Function Acos:
'                   calculates the arccosine of a argument.
'
'=====================================================================
'
FUNCTION Acos! (Arg!)
Acos! = ATN(SQR(1 - Arg! * Arg!) / Arg!)
END FUNCTION '=====================================================================
'          PROTOTYPE - "Oscilloscope" program                        '
'                                                                    '
'=====================================================================
SUB Adc

DIM H%(640)
DIM F%(640)

SCREEN 2

BeginG:
T% = 4
GetAdc T%, 640, VARSEG(H%(1)), VARPTR(H%(1))
PSET (0, 199)
Max = 0
```

```
FOR I% = 1 TO 639
    IF H%(I%) > Max THEN Max = H%(I%)
    LINE (I% + 1, F%(I% + 1))-(I%, F%(I%)), 0
    F%(I%) = H%(I%)
    LINE (I% - 1, H%(I% - 1))-(I%, H%(I%))
NEXT
GOTO BeginG
END SUB
```

```
'===========================================================
'
'       Procedure BlindSpotTest:
'                               Assume position of b-spot, if not there then
'                               Searchs for the blind spot with raster
'                               scan patern.
'                               Once center of the blind spot is located,
'                               do kinetic scans along 8 radials.
'                               Store blind spot radial pts (2 for each
'                               line segment) in test point array
'                               (elements 0 to 7)
'
'===========================================================

SUB BlindSpotTest (X&, Y&)

CONST CircleAng = 20 * Pie180      'circle we should be on to test B-Spot
CONST RadialAng = 185 * Pie180     'radial we should be on to test B-Spot
CONST CriticaLength = XP \ 36          'Length to indicate missed pt.
CONST Brightness = 13                  'Brightness of target led.(super threshold)
CONST ScanLine1 = Ycen + XP \ 36       'Y cooradinates of scan line
CONST ScanLine2 = Ycen                 'patern.
CONST ScanLine3 = Ycen + XP \ 13
CONST ScanLine4 = Ycen - XP \ 36
CONST ScanLine5 = Ycen + XP \ 15
CONST XBound2 = 7 * XP \ 18        'For right eye, the RIGHT most position
CONST XBound1 = 5 * XP \ 18        'for the scan lins.(X-components).
CONST DeltaX = XBound2 - XBound1       'Change in X-components.
CONST StpSize = 200                    'The interval step size.
CONST MinTime = 100                    'Min led off time.
CONST MultTime = 170                   'multiple of random #, for led off.
CONST Speed = 1500
CONST MinDegree = 7 * Pie180       'min B-Spot size in (7) deg (ver or hoz)
BSpot:                  'test where you think the blind spot is
    Calculate2 X&, Y&, RadialAng, CircleAng
    RelativeMove (X&), (Y&), Speed, 0              'move to center B-Spot
    RadialMove (X&), (Y&), 4, Speed, Brightness    'move out radial 4
    RadialMove (X&), (Y&), 0, Speed, Brightness    'Move out radial 0
DefineTB:                                          'define top,Bottom of B-spot
    RadialMove (X&), (Y&), 6, Speed, Brightness    'move out radial 6
    RadialMove (X&), (Y&), 2, Speed, Brightness    'Move out radial 2
    'if vertical and horizontal difference is to small
    'then this is not the blind spot
    IF ABS(BlindD2!(Eye%, 6) - BlindD2!(Eye%, 2)) < MinDegree OR ABS(BlindR2!(Eye%, 0) - BlindR2!(Eye%, 4)) < MinDegree THEN GOTO SearchBSpot
    Calculate2 (X&), Y1&, BlindD2!(Eye%, 2), BlindR2!(Eye%, 2)
    Calculate2 (X&), Y2&, BlindD2!(Eye%, 6), BlindR2!(Eye%, 6)
    Y& = (Y1& + Y2&) \ 2
    DefineBlindSpot X&, Y&, Speed, Brightness
EXIT SUB SearchBSpot:            'use scan patern to search for the blind spot.
    Y& = ScanLine1
    X1& = XBound1
    X2& = XBound2
    stepSize% = -StpSize
    Tim& = Time + MinTime
```

```
NextScan:
    RampUp (X2&), (Y&), Speed, 0
    Steps% = 0
DO:
    X& = Steps% + X2&
    RelativeMove (X&), (Y&), Speed, 0
        'target led on
    IF (TargetOn% = 0 AND Tim& < Time) AND Button(1) = 0 THEN
        ERASE Brt%, Group%: Brt%(0) = Brightness
        TargetLeds MaxOnTime
        Tim& = Time
        BSpotX& = X&
        TargetOn% = 1
    END IF
IF (Button(0) > 0 OR ABS(BSpotX& - X&) > 2 * CriticaLength) AND TargetOn% = 1 THE
N
        BSpotX1& = X&
        SetTimer 1              'leds off
        TargetOn% = 0
        IF ABS(BSpotX& - BSpotX1&) > CriticaLength THEN GOTO AssureBSpot
        Tim& = Time + MinTime + RND(1) * MultTime    'next led on time
    END IF
    Steps% = Steps% + stepSize%
LOOP WHILE (ABS(Steps%) < DeltaX OR TargetOn% = 1)
    stepSize% = stepSize% * (-1)                    'move in opposite dirc
    SWAP X1&, X2&                                   'did not find
    IF Y& = ScanLine1 THEN Y& = ScanLine2: GOTO NextScan  'blind spot.
    IF Y& = ScanLine2 THEN Y& = ScanLine3: GOTO NextScan  'move down to
    IF Y& = ScanLine3 THEN Y& = ScanLine4: GOTO NextScan  'next scan line.
    IF Y& = ScanLine4 THEN Y& = ScanLine5: GOTO NextScan
    IF ChangeEye% = 1 THEN                          'can not find blind spot
        FOR I% = 0 TO 7             'already checked other eye
            BlindR1!(Eye%, I%) = 99 'set data so I know there is no
        NEXT                        'blind spot.
        Eye% = Eye% XOR 1
        IF Eye% = 0 THEN Character 27, 29 ELSE Character 21, 29
        EXIT SUB                    'premature exit
    END IF 'Switch eye. (Cannot find blind spot, must be other eye.)
    Eye% = Eye% XOR 1: ChangeEye% = 1
    IF Eye% = 0 THEN Character 27, 29 ELSE Character 21, 29
    GOTO BSpot AssureBSpot:                            'Make sure this is the blind spot.
    TurnAround (X&), (Y&), (stepSize%), 0, Speed
    RelativeMove (BSpotX&), (Y&), Speed, 0    'move back.
    IF stepSize% > 0 THEN                'define other side of B-Spot
        Calculate1 (BSpotX1&), (Y&), BlindD2!(Eye%, 0), BlindR2!(Eye%, 0), BlindTim
&(Eye%, 0), 0
        RadialMove (BSpotX&), (Y&), 4, Speed, Brightness
    ELSE
        Calculate1 (BSpotX1&), (Y&), BlindD2!(Eye%, 4), BlindR2!(Eye%, 4), BlindTim
&(Eye%, 4), 0
        RadialMove (BSpotX&), (Y&), 0, Speed, Brightness
    END IF                  'calculate center b-spot
    Calculate2 X1&, (Y&), BlindD2!(Eye%, 0), BlindR2!(Eye%, 0)
    Calculate2 X2&, (Y&), BlindD2!(Eye%, 4), BlindR2!(Eye%, 4)
    X& = (X1& + X2&) \ 2
    RelativeMove (X&), (Y&), Speed, 0            'move to center
    GOTO DefineTB
END SUB
```

```
'==============================================================
'       FUNCTION BUTTON:
'                       THIS FUNCTION RETURNS THE VALUE WHICH REPRESENTS
'                       THE NUMBER OF TARGETS SEEN BY THE PATIANT.
'                       THE VALUE WILL NOT BE LOST UNTIL THE FUNCTION IS
'                       PASSED A 0, ANY OTHER VALUE WILL PERSERVE THE DATA.
'
'==============================================================
FUNCTION Button% (Bclr%) STATIC
STATIC Vox$
    IF Vox$ = "" THEN Vox$ = INKEY$
    IF Buttons%(1) > 0 OR Vox$ > "" THEN
        IF Buttons%(1) > 0 THEN
            Button% = Buttons%(Bclr%)
        ELSEIF Vox$ >= "1" AND Vox$ <= "4" THEN
            Button% = ASC(Vox$) - 48
            IF Bclr% = 0 THEN Vox$ = ""
        ELSE
            Vox$ = ""
        END IF
    END IF
END FUNCTION
```

```
'================================================================
'               ocedure Calculate1:
'                       Calculates the angle of the eye between the
'                       Target Led and the pursuit Led. It also
'                       Calculates then angle of the eye from the center
'                       of the eye to the pursuit led.
'                       X&,Y& = the current position of the pursuit led
'                       Ang1! = the angle of the radial on which the
'                               target led lies.
'                       Ang2! = the angle of the circle on which the
'                               target led lies.
'                       LtPosX&,LtPosY&
'                             = the position of the led (x,y) to
'                               calculate angles from.
'================================================================
                   ate1 (X&, Y&, Ang1!, Ang2!, Tim&, Light%)
              Time - Tim&                'calculate time to respond
              X& - LightPosX&(Light%)
              Y& - LightPosY&(Light%)
               DLX!) = 0 THEN DLX! = .0001   'if zero then
              = ATN(DLY! / DLX!)             'calculate radial angle
               DLX!) = -1 THEN Ang1! = Ang1! + PIE  'if less then 0
               Ang1!) = -1 THEN Ang1! = Ang1! + Pie2 'if less then 0
              = Pie2 - Ang1!                 'KEEP WITH CONVENTIONAL POLAR COORDINATES
               X! * DLX! + DLY! * DLY!
                       istance2 + Length2&(Light%)
              = Xcen - X&                    'temp variables
              = Ycen - Y&
                   istance2 + (TempX! * TempX!) + (TempY! * TempY!)
                   = Acos((B! + C! - A!) / (SQR(4 * B! * C!)))
```

```
'================================================
'       Procedure Calculate2:
'                       Calculates the position in steps (x,y) from
'                       the angle of the eye between the Target
'                       Led and the pursuit Led and the angle of
'                       the eye from the center of the screen to
'                       the pursuit led.
'
'================================================

SUB Calculate2 (X&, Y&, Ang1!, Ang2!)
   R& = Pdistance * TAN(Ang2!)
   X& = Xcen + R& * COS(Ang1!)
   Y& = Ycen - R& * SIN(Ang1!)
   IF X& > XP OR Y& > YP OR SGN(X&) = -1 OR SGN(Y&) = -1 THEN X& = 0: Y& = 0
END SUB '================================================
'       Procedure Calculate3:
'                       Calculates the position (x,y) for CGA output from
'                       the angle of the eye between the Target
'                       Led and the pursuit Led and the angle of
'                       the eye from the center of the screen to
'                       the pursuit led.
'                       (prototype only)
'
'================================================

SUB Calculate3 (X%, Y%, Ang1!, Ang2!)
CONST XcS = 320
CONST YcS = 99
CONST Ratio = 2.38
   Ang! = Ang2! * 180 / PIE
   X% = XcS + Ang! * COS(Ang1!) * Ratio
   Y% = YcS + Ang! * SIN(Ang1!)
   PSET (X%, Y%)
END SUB
```

```
'================================================
'
'
'
'
'
'================================================

SUB DefineBlindSpot (X&, Y&, Speed%, BRIGHT%)
               'even radials have already been defined
   FOR I% = 1 TO 7 STEP 2           'define old radials (0-7)
      RadialMove (X&), (Y&), (I%), (Speed%), (BRIGHT%)
   NEXT
   X& = X& + 3536        'POSITION OF LAST (7) RADIAL AT FULL DISTANCE
   Y& = Y& - 3536        '5000 * SIN( (7/8) * PIE )
END SUB
```

```
'===========================================================================
'
'        Procedure Diagnostics:
'                            Power-on Diagnostics test of entire system.
'                            Test motor currents (A-D across sample resistor).
'                            Test all leds with light sensor.
'                            Test background lights with light sensor.
'                            If failure then indicate to operator.
'
'===========================================================================
'
SUB Diagnostics                        'just show that lights work! (try this bryan)
CONST Delay = 20
CONST BT = 15                          'constant brightness for test
    Character 32, 29        'display 'wt' wait
    I& = 1
    FOR I& = 65535 TO 1 STEP -200
       LightLevel GroupA, I&
       LightLevel GroupB, I&
       LightLevel GroupC, I&
       LightLevel GroupD, I&
       FOR Y% = 1 TO 10000
          OUT LedSelect, 0
          OUT LedSelect, &H55
          OUT LedSelect, &HAA
          OUT LedSelect, &HFF
       NEXT
    NEXT
FOR I = 1 TO 50
    FOR T% = 0 TO 3
       Brt%(T%) = BT
       Group%(T%) = INT(RND(1) * 4)
    NEXT
    TargetLeds 5000
    FOR Y = 1 TO Delay: NEXT
NEXT
SetTimer 1                    'Turn off leds
END SUB '===========================================================================
'
'        Procedure DisplayResults:
'                            displays the test results on the screen
'                            (prototype only)
'
'===========================================================================
'
SUB DisplayResults CONST XcS = 320
CONST YcS = 99
CONST Ratio = 2.38
CONST Radials = 24
SCREEN 2: CLS
    LOCATE 24, 1: PRINT "Hill of vision:"; Hill%
    LOCATE 1, 60: IF Eye% = 0 THEN PRINT "Right eye" ELSE PRINT "Left eye"
    LOCATE 1, 1: PRINT "x Represents pts not tested"
    LOCATE 2, 3: PRINT "Represents pts tested okay"
    LOCATE 3, 3: PRINT "Represents pts missed"
    LINE (0, 9)-(8, 14), , B
    LINE (0, 18)-(8, 23), , BF
    CIRCLE (XcS, YcS), 90 * Ratio     '90 DEGREES MAX
    FOR I% = 0 TO Radials - 1
       LINE (XcS + 5 * Ratio * COS(Pie2 * I% / Radials), YcS + 5 * SIN(Pie2 * I% /
Radials))-(XcS + 90 * Ratio * COS(Pie2 * I% / Radials), YcS + 90 * SIN(Pie2 * I%
/ Radials)), , , &H1111
    NEXT
    FOR I% = 1 TO 99
       IF PtSaw%(Eye%, I%) = 0 THEN
          LINE (XcS + Ratio * (Pt(1, I%) * 180 / PIE) * COS(Pt(2, I%)) - 2, YcS +
(Pt(1, I%) * 180 / PIE) * SIN(Pt(2, I%)) - 2)-(XcS + Ratio * (Pt(1, I%) * 180 / P
```

```
IE) * COS(Pt(2, I%)) + 2, YcS + (Pt(1, I%) * 180 / PIE) * SIN(Pt(2, I%)) _
+ 2)
            LINE (XcS + Ratio * (Pt(1, I%) * 180 / PIE) * COS(Pt(2, I%)) - 2, YcS +
(Pt(1, I%) * 180 / PIE) * SIN(Pt(2, I%)) + 2)-(XcS + Ratio * (Pt(1, I%) * 180 / P
IE) * COS(Pt(2, I%)) + 2, YcS + (Pt(1, I%) * 180 / PIE) * SIN(Pt(2, I%)) _
- 2)
         ELSE
            IF PtSaw%(Eye%, I%) <> 100 THEN
            LINE (XcS + Ratio * (Pt(1, I%) * 180 / PIE) * COS(Pt(2, I%)) - 2, YcS +
(Pt(1, I%) * 180 / PIE) * SIN(Pt(2, I%)) - 2)-(XcS + Ratio * (Pt(1, I%) * 180 / P
IE) * COS(Pt(2, I%)) + 2, YcS + (Pt(1, I%) * 180 / PIE) * SIN(Pt(2, I%)) _
+ 2), , BF
            ELSE
            LINE (XcS + Ratio * (Pt(1, I%) * 180 / PIE) * COS(Pt(2, I%)) - 2, YcS +
(Pt(1, I%) * 180 / PIE) * SIN(Pt(2, I%)) - 2)-(XcS + Ratio * (Pt(1, I%) * 180 / P
IE) * COS(Pt(2, I%)) + 2, YcS + (Pt(1, I%) * 180 / PIE) * SIN(Pt(2, I%)) _
+ 2), , B
            END IF
         END IF
   NEXT
END SUB '================================================================
'
'        FUNCTION HillOfVision:
'            Test 4 fixed pts, two along each 45 degree radial using
'            static/thresholding procedure to determine patient's
'            deviation from standard hill of vision.
'
'
'
'================================================================
'
FUNCTION HillOfVision% (X&, Y&)
CONST Speed = 1000
CONST Delta = 15 * PIE / 180         'CHANGE IN ANGLE PER STEP
CONST MinStep = 500                  'ONE STEP
CONST MaxStep = 1000
CONST ReactionTime = -200                    'max time for the patient to respond
CONST OnTime = 100                           'max led on time: about (100/244) sec
CONST R = Pdistance * .32492                 'radius = Pdistance*tan(18 Degree)
DIM ThH%(4)                                  ' four pt test for hill of vision
DIM BrightMin%(4)
DIM BrightMax%(4)
FOR T% = 1 TO 4
    BrightMax%(T%) = 18                      'initial max is 18 DB
    BrightMin%(T%) = 26                      'initial min is 26 DB
NEXT
Theata = (7 / 8) * Pie2              'BEGINNING ANGLE
I% = 1                               'START AT ONE (ZERO IS TO CLOSE TO B-SPOT)
DO
   DO
      X1& = Hill&(0, I%)
      Y1& = Hill&(1, I%)
      DO
         X& = X& + MinStep * COS(Theata)
         Y& = Y& + MinStep * SIN(Theata)
         IF SGN(X&) = -1 THEN X& = 0
         IF SGN(Y&) = -1 THEN Y& = 0
         IF X& > XP THEN X& = XP
         IF Y& > YP THEN Y& = YP
         RelativeMove (X&), (Y&), Speed, 0
         DeltaX& = X& - X1&
         DeltaY& = Y& - Y1&
         IF DeltaX& = 0 THEN
         Theata1 = ATN(DeltaY& / .00001)
         ELSE
         Theata1 = ATN(DeltaY& / DeltaX&)
         END IF
         IF DeltaX& > 0 THEN Theata1 = Theata1 + PIE
```

```
            IF (Theatal - Theata) > PIE THEN
        Theatal = Theatal - Pie2
        ELSEIF (Theata - Theatal) > PIE THEN Theatal = Theatal + Pie2
           END IF
           IF ABS(Theata - Theatal) < Delta THEN
        Theata = Theatal
           ELSE
        IF Theata > Theatal THEN
           Theata = Theata - Delta
        ELSE
           Theata = Theata + Delta
        END IF
          END IF
     IF LedOn% <> 0 THEN                    'IF LED IS ON THEN
       IF Button(0) > 0 THEN             'he saw the target
          BrightMax%(LedOn%) = BRIGHT%
          BRIGHT% = (BrightMin%(LedOn%) + BrightMax%(LedOn%)) \ 2
          IF (BrightMax%(LedOn%) + 2) > BrightMin%(LedOn%) THEN
             ThH%(LedOn%) = (BrightMin%(LedOn%) + BrightMax%(LedOn%)) \ 2
          END IF
          LedOn% = 0
          SetTimer 1              'turn leds off
       ELSEIF ReadTimer < ReactionTime THEN    'he did not see the target
          BrightMin%(LedOn%) = BRIGHT%
          BRIGHT% = (BrightMin%(LedOn%) + BrightMax%(LedOn%)) \ 2
          IF (BrightMax%(LedOn%) + 2) > BrightMin%(LedOn%) THEN
             ThH%(LedOn%) = (BrightMin%(LedOn%) + BrightMax%(LedOn%)) \ 2
          END IF
          LedOn% = 0
     END IF
      END IF
       LOOP WHILE ABS(DeltaX&) > MinStep OR ABS(DeltaY&) > MinStep
        IF ThH%(1) = 0 OR ThH%(2) = 0 OR ThH%(3) = 0 OR ThH%(4) = 0 THEN
     LedOn% = Hill&(3, I%)
     IF BRIGHT% < BrightMin%(LedOn%) OR BRIGHT% > BrightMax%(LedOn%) THEN
          BRIGHT% = (BrightMin%(LedOn%) + BrightMax%(LedOn%)) \ 2
     END IF
     ERASE Brt%
     Brt%((Hill&(2, I%) \ 4)) = BRIGHT% ' or 11 to defeat
     Group%((Hill&(2, I%) \ 4)) = Hill&(2, I%) MOD 4
     TargetLeds OnTime
     I% = I% + 1                  'INDEX TO NEXT PT
     IF I% > 17 THEN I% = 0
          END IF
       LOOP WHILE ThH%(1) = 0 OR ThH%(2) = 0 OR ThH%(3) = 0 OR ThH%(4) = 0
     I% = I% + 1
     IF I% < 18 THEN I% = 18 'INDEX TO POSITION READY PT.
LOOP WHILE I% < 20         'POSITION READY FOR TESTPT
HillOfVision = NormalizeHill(ThH%())    ' Normalize hill of vision.
END FUNCTION
'===============================================================
'
'       Procedure HomePosition:
'                             On power up and on every new test
'                             the perimeter home position must be calibrated.
'                             this procedure finds its (0,0) position.
'
'===============================================================
'
SUB HomePosition
CONST Add = 2000                          'additional motion toward home.
     LastY& = 0                           'let it think it is at (0,0)
     LastX& = 0                           'go at least screen length in
                         'direction of home.(it will hit)
     PositionControl -(XP + Add), -(YP + Add), 400, 32
     LastY& = 0                           'it must be at home so
     LastX& = 0                           'give it poisition (0,0)
     RampUp (Xcen), (Ycen), 300, 0        'tell it to go to center scre
en.
     LightLevel Pursuit, UnitLog&(PBright)    'Turn pursuit led on.
END SUB
```

```
'==========================================================================
'
'       Function Length:
'                       Determines the length (distance) between two points
'                       using Pythagorian Theroem.
'
'==========================================================================

FUNCTION Length! (X!, Y!)
Length! = X! * X! + Y! * Y!
END FUNCTION

'==========================================================================
'
'       PROCEDURE MOVE1ANDLED:
'                       This procedure determines if it is time to turn
'                       on led, and if there are possible leds to turn
'                       on. it turns them on then monitors responses
'                       to determine if the targets where seen or not.
'                       (used by procdure testpt [99 pt test])
'
'==========================================================================

SUB MovelandLed (X&, Y&, Speed%, Control%) STATIC
CONST ER = 2000
CONST OnTime = 150
CONST ReactionTime = -350
CONST DelayTime = 100
DIM Saw%(4)
DIM PtNum%(4)
RelativeMove (X&), Y&, Speed%, (Control%)
IF LedOn% = 0 THEN                          'IF LEDS ARE OFF THEN
  IF Tim& < Time THEN
    Test2% = CompArray(1584, X&, Y&, ER, VARSEG(PossibleS&(1, 0)), VARPTR(Possible
S&(1, 0)))
    IF Test2% > 0 THEN
      ERASE Brt%                            'SET BRT% ARRAY EQUAL TO LEDOFF=0
      Temp% = Button(0)                     'CLEAR BUTTON
      Saw%(0) = 110: Saw%(1) = 110: Saw%(2) = 110: Saw%(3) = 110
      FOR I% = 0 TO Test2% - 1
      Index% = PossibleS&(1, I%)
      Group% = PossibleS&(2, I%) \ 4
      IF PtSaw%(Eye%, Index%) <> 1 AND Saw%(Group%) >= PtSaw%(Eye%, Index%) THEN 'TE
ST THE PT WITH THE LOWEST PERCENTAGE
        IF Saw%(Group%) = 110 THEN LedOn% = LedOn% + 1
        Saw%(Group%) = PtSaw%(Eye%, Index%)
        Group%(Group%) = PossibleS&(2, I%) MOD 4    '0 TO 3 THE LED% (TARGETLEDS)
        Brt%(Group%) = BRIGHT%(Index%)
        PtNum%(Group%) = Index%
    END IF
    NEXT
    IF LedOn% > 0 THEN TargetLeds OnTime: PRINT LedOn%, ;
    END IF
  END IF
ELSE                                        'LEDS ARE ON THEN
    IF Button(1) >= LedOn% THEN             'She saw ALL THE targetS
      Temp% = Button(0)
      PRINT Temp%
      FOR I% = 1 TO 3
      PtSaw%(Eye%, PtNum%(I%)) = 100
      NEXT
      Tim& = DelayTime + Time
      LedOn% = 0
      SetTimer 1                            'turn leds off
    ELSE
      IF ReadTimer < ReactionTime THEN      'he did not see the target
      Temp% = Button(0)
      PRINT Temp%
      FOR I% = 0 TO 3: IF PtSaw%(Eye%, PtNum%(I%)) = 100 THEN PtNum%(I%) = 0: I;
dOn% = LedOn% - 1: Temp% = Temp% - 1
      NEXT
      IF Temp% > 0 THEN
        FOR I% = 0 TO 3
```

```
            IF PtNum%(I%) <> 0 THEN PtSaw%(Eye%, PtNum%(I%)) = (Temp% * 100) \ LedOr
              NEXT
            ELSE
              FOR I% = 1 TO 3
              PtSaw%(Eye%, PtNum%(I%)) = 1
              NEXT
            END IF
            Tim& = DelayTime + Time
            LedOn% = 0
          END IF
        END IF
      END IF
    END SUB '===========================================================================
'          Procedure Move2andLed:
'                              this procedure is similar to Move1andLed. The
'                              difference is that it is called by TestMissedPts
'                              it must turn on the pt to be tested plus any
'                              others possible targets that have already been
'                              tested okay.
'
'===========================================================================

SUB Move2andLed (X&, Y&, X1&, Y1&, Speed%, Led%, Index%) STATIC
CONST ER = 2000
CONST OnTime = 150
CONST ReactionTime = -350
CONST Min = 500
DIM Saw%(4)
RelativeMove (X&), (Y&), Speed%, 0
IF LedOn% = 0 THEN                          'IF LEDS ARE OFF THEN
  IF ABS(X1& - X&) < Min AND ABS(Y1& - Y&) < Min THEN     'IF IN RANGE TO TEST PT
    Test2% = CompArray(1584, X&, Y&, ER, VARSEG(PossibleS&(1, 0)), VARPTR(Possible
S&(1, 0)))
      ERASE Brt%, Saw%
      Temp% = Button(0)                          'CLEAR BUTTON
      LedOn% = 1                                 'THE TEST PT
      TestPt% = Index%                           'ACTUAL PT BEING TESTED
      Group% = Led% \ 4
      Saw%(Group%) = 1                           'THIS GROUP HAS A TEST TARGET
      Group%(Group%) = Led% MOD 4                '0 TO 3 THE LED% (TARGETLEDS)
      Brt%(Group%) = BRIGHT%(Index%)
      IF Test2% > 0 THEN
        FOR I% = 0 TO Test2% - 1
      Index% = PossibleS&(1, I%)
      Group% = PossibleS&(2, I%) \ 4
      IF PtSaw%(Eye%, Index%) = 100 AND Saw%(Group%) = 0 THEN           'ADD A PT THAT
IS 100%
        LedOn% = LedOn% + 1
      . Saw%(Group%) = 100
        Group%(Group%) = PossibleS&(2, I%) MOD 4   '0 TO 3 THE LED% (TARGETLEDS)
        Brt%(Group%) = BRIGHT%(Index%)
      END IF
    NEXT
    END IF
    PRINT LedOn%, ;
    TargetLeds OnTime
  END IF
ELSE                                        'LEDS ARE ON THEN
    IF Button(1) >= LedOn% THEN             'She saw ALL THE targets
      Temp% = Button(0)
      PRINT Temp%
      PtSaw%(Eye%, TestPt%) = 100
      LedOn% = 0
      SetTimer 1                            'turn leds off
    ELSE
```

```
      IF ReadTimer < ReactionTime THEN         'he did not see the targets
        Temp% = Button(0)
        PRINT Temp%
        PtSaw%(Eye%, TestPt%) = 101     'MISSED '101
        LedOn% = 0
            END IF
          END IF
      END IF
      END SUB
```

```
'================================================================
'
'       Function NormalizeHill:
'
'                       the Procedure HillOfVision to determine
'                       the patient's deviation from a "normal
'                       hill of vision".
'                       The result is a single numberical value by
'                       which every pt on the "normal hill of vision"
'                       is mult to get the patient's true hill of
'                       vision.
'
'================================================================

FUNCTION NormalizeHill% (ThH%())
Max% = 40                                    'MAX SENSITIVITIY IS 40 DB
FOR I% = 1 TO 4
   IF ThH%(I%) < Max% THEN Max% = ThH%(I%)
   Avg% = Avg% + ThH%(I%)
NEXT
NormalizeHill = 25 - (Avg% - Max%) \ 3    'THE DIFFERENCE BETWEEN 25DB ('NORMAL')
END FUNCTION
```

```
'================================================================
'
'       Procedure PlotTest:
'                       Plot the results of the test,
'                       with or without coordinate system.
'
'================================================================

SUB PlotTest
CONST Speed = 400
CONST Speed2 = Speed * 2
CONST Radius = (3.875 / ScreenWidth) * XP
CONST Xc1 = XP - 11783              'X-CENTER OF PLOT #1
CONST Xc2 = Xc1 - (8.625 / ScreenWidth) * XP          'X-CENTER OF PLOT #2
CONST Yc = 6690                  'Y-CENTER OF PLOTS (#1 AND #2)
CONST Pie5 = PIE / 2
   Eye% = 0
   PositionControl XP, 0, Speed, 0           'go to upper right corner
                   'of perimeter.
   LOCATE 1, 18: PRINT "Waiting for pen to be loaded, Hit any key"
   DO: Q$ = INKEY$: LOOP WHILE Q$ = ""
   LOCATE 1, 18: PRINT "plotting..."; SPC(49);
   FOR I% = 1 TO 99          'RIGHT EYE PLOT
      R = Pt(1, I%) * Radius / Pie5
      IF PtSaw%(0, I%) <> 100 THEN      'DID HE MISS IT
         Square (Xc1 + R * COS(Pt(2, I%))), (Yc - R * SIN(Pt(2, I%))), Speed2
      END IF
   NEXT
   FOR I% = 1 TO 99          'LEFT EYE PLOT
      R = Pt(1, I%) * Radius / Pie5
      IF PtSaw%(1, I%) <> 100 THEN      'DID HE MISS IT
         Square (Xc2 - R * COS(Pt(2, I%))), (Yc - R * SIN(Pt(2, I%))), Speed2
      END IF
   NEXT
END SUB
```

```
'================================================================
'
'        Procedure PositionControl:
'                              Given a new X and Y position and a speed
'                              calculate the number of steps and the step
'                              rate. These parameters are then passed to
'                              Procedure MotorControl
'                              'Control' is for the plotter function
'                              (solenoid) and the low current wait state.
'                   Xpos = is the new absolute x position (in micro steps)
'                   Ypos = is the new absolute Y position (in micro steps)
'                   speed = speed of motion
'                   control = soleniod and low current control byte
'                              (&h30 actives niod  XX actives low current)
'================================================================
'
SUB PositionControl (Xpos&, Ypos&, Speed%, Control%)
    NumStepY& = Ypos& - LastY&           'calculate +-# step y direction.
    NumStepX& = Xpos& - LastX&           'calculate +-# step x direction.
        'The minumum step is 1, so if either is 0 make it 1.
    IF SGN(NumStepY&) = 0 THEN
       NumStepY& = 1
    ELSEIF SGN(NumStepX&) = 0 THEN
       NumStepX& = 1
    END IF
        'if it does not move(x,y steps =0) then exit sub
    IF SGN(NumStepX&) = 0 THEN EXIT SUB
        'Determine the direction in each axis (part of control byte)
    IF SGN(NumStepX&) = -1 THEN Control% = Control% OR 1
    IF SGN(NumStepY&) = 1 THEN Control% = Control% OR 2
        'last() keeps track of the last position.
        'needed for calculation of steps to next position
    LastY& = LastY& + NumStepY&
    LastX& = LastX& + NumStepX&
        'calculate # of steps (x,y) directions
    NumStepX& = ABS(NumStepX&)
    NumStepY& = ABS(NumStepY&)
        'calculate step rate for both x and y motion.
        'make sure it is not more then 16 bits (65535)
    IF NumStepX& > NumStepY& THEN
       StepRateX& = Speed%
       StepRateY& = (Speed% * NumStepX&) \ NumStepY&
       IF StepRateY& > 65535 THEN StepRateY& = 0
    ELSE StepRateY& = Speed%
       StepRateX& = (Speed% * NumStepY&) \ NumStepX&
       IF StepRateX& > 65535 THEN StepRateX& = 0
    END IF
        'An assembly language routine to give the 8253 the info about step
        'size and step rate of each axis.(it will wait if previous motion
        'is not complete or if noid position has changed wait 140 ms).
    CALL MotorControl(NumStepX&, NumStepY&, (StepRateX&), (StepRateY&), Control%)
END SUB
```

```
'==========================================================
'
'          Procedure RadialMove:
'                           Moves out a radial (0-7) 8 in all.
'                                  5 6 7
'                                   \|/
'                                 4- * -0
'                                   /|\
'                                  3 2 1
'                           until the patiant see's the light.
'
'==========================================================
'
SUB RadialMove (X&, Y&, I%, Speed%, BRIGHT%)
CONST MaxSteps = 5000
CONST stepSize = 300
CONST Pie4 = PIE / 4
Calculate1 (X&), (Y&), BlindD1!(Eye%, I%), BlindR1!(Eye%, I%), BlindTim&(Eye%, I%), 0
DO                      'wait until button is depressed
LOOP WHILE (INP(&H300) AND &H12) <> &H12 OR Button(0) > 0
ERASE Brt%, Group%: Brt%(0) = BRIGHT%
TargetLeds MaxOnTime
DO      'move out the radial with a target led on!
    Steps% = Steps% + stepSize
    RelativeMove X& + INT(Steps% * COS(Pie4 * I%)), Y& + INT(Steps% * SIN(Pie4 * I%)), (Speed%), 0
LOOP WHILE (Steps% < MaxSteps) AND Button(1) = 0
EndRadial:      ' led off, turn around, move to center, calculate edge of b-Spot
    SetTimer 1    'led off
    IF I% = 7 THEN  'IF LAST RADIAL THEN NO NEED TO TURN AROUND!
        Calculate1 X& + INT(Steps% * COS(Pie4 * I%)), Y& + INT(Steps% * SIN(Pie4 * I%)), BlindD2!(Eye%, I%), BlindR2!(Eye%, I%), BlindTim&(Eye%, I%), 0
    ELSE
        TurnAround X& + INT(Steps% * COS(Pie4 * I%)), Y& + INT(Steps% * SIN(Pie4 * I%)), stepSize * COS(Pie4 * I%), stepSize * SIN(Pie4 * I%), Speed%
        RelativeMove (X&), (Y&), Speed%, 0               'Move to center
        Calculate1 X& + INT(Steps% * COS(Pie4 * I%)), Y& + INT(Steps% * SIN(Pie4 * I%)), BlindD2!(Eye%, I%), BlindR2!(Eye%, I%), BlindTim&(Eye%, I%), 0
    END IF
END SUB '==========================================================
'
'          Procedure RampUpDown:
'                           Purpose of this procedure is to start and stop
'                           the stepper motors at a speed other than max.
'                           It ramps the speed up at the begining and back
'                           down at the end.
'                           (may not be needed in final design)
'
'==========================================================
SUB RampUp (Xpos&, Ypos&, Speed%, Control%)
CONST beginingSpeed = 2000
CONST RampStep = 50
IF Eye% = 1 THEN Xpos& = XP - Xpos&
LASTX1& = LastX&        'SAVE LAST POSITION
LASTY1& = LastY&
PositionControl (Xpos&), (Ypos&), beginingSpeed, Control%
DeltaY& = ABS(LASTY1& - LastY&)
DeltaX& = ABS(LASTX1& - LastX&)
    'if it does not move then no need to continue.
IF (DeltaY& = 0) OR (DeltaX& = 0) THEN EXIT SUB
    'ramp up
FOR Spd% = beginingSpeed TO Speed% STEP -RampStep
    IF DeltaX& > DeltaY& THEN
        StepRateX& = Spd%
        StepRateY& = ABS((Spd% * DeltaX&) \ DeltaY&)
        IF StepRateY& > 65535 THEN StepRateY& = 0
```

```
      ELSE StepRateY& = Spd%
         StepRateX& = ABS((Spd% * DeltaY&) \ DeltaX&)
         IF StepRateX& > 65535 THEN StepRateX& = 0
      END IF
      LightLevel &H305, StepRateX&     'OUT PORT 305
      LightLevel &H304, StepRateY&     'OUT PORT 304
   NEXT Spd%
END SUB
```

```
'================================================================
'
'       Procedure RelativeMove:
'                        Calculates position relative to which eye
'                        is being tested. (Left eye is a mirror image
'                        about the Y-axis of the right eye)
'                        Moves accordingly.
'
'================================================================

SUB RelativeMove (X&, Y&, Speed%, Control%)
   IF Eye% = 1 THEN
      PositionControl (XP - X&), Y&, Speed%, Control%
   ELSE
      PositionControl X&, Y&, Speed%, Control%
   END IF
END SUB
```

```
'================================================================
'
'       Procedure SelectEye:
'               Determines which eye is to be tested.
'               inp(&h300) bit 1, is operator button bit.
'               buttons function, is not zero if button has been
'               pushed since last time it was cleared (interupt polled).
'
'================================================================

SUB SelectEye
CONST Delay = 200        'ONE SECOND
PositionControl Xcen + 1, Ycen + 1, 400, 32     'low current to the motors.
                'get display right (or left)
BeginWait:
   IF Eye% = 0 THEN Character 27, 29 ELSE Character 21, 29
   X% = Buttons%(0)                             'clear button bit.
   DO                           'COUNTS THE NUMBER OF TIMES THE BUTTON
   LOOP WHILE Buttons%(1) = 0      'pressed (polled by interupt).
   Variable = Time                              'save time value.
                'wait about five seconds.
   DO                                           'or until button is pressed.
   LOOP WHILE (Time < Variable + Delay AND Buttons%(1) < 2)
   IF Buttons%(0) > 1 THEN
      IF Eye% = 0 THEN                          'if right eye
         Eye% = 1                              'Change to left eye
         GOTO BeginWait                        'then wait.
      ELSEIF Eye% = 1 AND BlindR1!(0, 1) = 0 THEN  'if left eye and no
         Eye% = 0                              'data taken on right eye
         GOTO BeginWait                        'then change eye;wait
         ELSE
         Eye% = 3                              'skip left eye test
      END IF                                   'procede to plot
   END IF
END SUB
```

```
'=============================================================
'       Procedure Square:
'                       plots a square on the output plot
'
'=============================================================
SUB Square (X&, Y&, Speed%)
CONST SPEED1 = 1200              'PLOTSPEED
CONST SIZE = 200 \ 2             'SIZE OF SQUARE
    PositionControl (X& - SIZE), (Y& - SIZE), Speed%, 0
    PositionControl (X& + SIZE), (Y& - SIZE), SPEED1, 16
    PositionControl (X& + SIZE), (Y& + SIZE), SPEED1, 16
    PositionControl (X& - SIZE), (Y& + SIZE), SPEED1, 16
    PositionControl (X& - SIZE), (Y& - SIZE), SPEED1, 16
END SUB '=============================================================
'
'       Procedure TargetLeds:
'                       turn on appropriate LEDs at given brightness.
'                       There are four groups of leds in which there
'                       are four leds.
'                       Variables:
'                               Led(n)% - Which led of group (n)
' LEFT EYE TEST IS JUST THE               n={1,2,3,4} is to be
' SAME AS THE RIGHT EYE TEST              turned on
' EXCEPT THAT THE LEDS ARE        level(n)& - the brightness level of
' INVERTED ABOUT THE Y-AXIAS                  led in group (n).(in DBs)
' AND SO IS THE MOTION!           LedOnTime&- the time the leds are to
'                                             be on (time=ledontime/298)
'
'=============================================================
'
SUB TargetLeds (LedOnTime%)
IF Eye% = 0 THEN         'RIGHT EYE
   OUT LedSelect, (Group%(0) + 4 * Group%(1) + 16 * Group%(2) + 64 * Group%(3))
'turn on appropriate leds.
    LightLevel GroupA, -(UnitLog&(Brt%(0) - Hill%) \ RelativeI&(1, Group%(0)))'set
 relative
    LightLevel GroupB, -(UnitLog&(Brt%(1) - Hill%) \ RelativeI&(2, Group%(1)))'bri
ghtness
    LightLevel GroupC, -(UnitLog&(Brt%(2) - Hill%) \ RelativeI&(3, Group%(2)))
    LightLevel GroupD, -(UnitLog&(Brt%(3) - Hill%) \ RelativeI&(4, Group%(3)))
    ELSE                 'LEFT EYE
   OUT LedSelect, (LeftAC%(Group%(0)) + 4 * LeftBD%(Group%(3)) + 16 * LeftAC%(Gro
up%(2)) + 64 * LeftBD%(Group%(1)))
    LightLevel GroupA, -(UnitLog&(Brt%(0) - Hill%) \ RelativeI&(1, LeftAC%(Group%(
0))))'set relative
    LightLevel GroupB, -(UnitLog&(Brt%(3) - Hill%) \ RelativeI&(2, LeftBD%(Group%(
3))))'brightness
    LightLevel GroupC, -(UnitLog&(Brt%(2) - Hill%) \ RelativeI&(3, LeftAC%(Group%(
2))))
    LightLevel GroupD, -(UnitLog&(Brt%(1) - Hill%) \ RelativeI&(4, LeftBD%(Group%(
1))))
END IF
SetTimer LedOnTime%                           'set leds on timer registor.
END SUB '=============================================================
'
'       Procedure TestMissedPts:
'                       Retest pts missed during the 80 pt test.
'                       Test using mult stimulis with seen pts.
'                       the results of this procedure are pts
'                       that are definitely missed.
'                       These are the pts that will be plotted
'                       on the graph.
'
'
'=============================================================
'
SUB TestMissedPts (X&, Y&)
CONST Speed = 1000
```

```
CONST Delta = 15 * PIE / 180
CONST MinStep = 500                    'ONE STEP
CONST MaxStep = 1000
CONST MinDistance = 8000
X1& = X&: Y1& = Y&
MOVE:
DO
Index% = ClosElement(X1&, Y1&, VARSEG(PtSaw%(Eye%, 1)), VARPTR(PtSaw%(Eye%, 1)),
VARSEG(PossibleS&(1, 0)), VARPTR(PossibleS&(1, 0)), MinDistance)
Led% = PossibleS&(1, 0)
IF Index% > 0 THEN
    DO
        X& = X& + MinStep * COS(Theata)
        Y& = Y& + MinStep * SIN(Theata)
        IF SGN(X&) = -1 THEN X& = 0
        IF SGN(Y&) = -1 THEN Y& = 0
        IF X& > XP THEN X& = XP
        IF Y& > YP THEN Y& = YP
        Move2andLed (X&), (Y&), (X1&), (Y1&), Speed, (Led%), (Index%)
        DeltaX& = X& - X1&
        DeltaY& = Y& - Y1&
        IF DeltaX& = 0 THEN
        Theata1 = ATN(DeltaY& / .00001)
        ELSE
        Theata1 = ATN(DeltaY& / DeltaX&)
        END IF
        IF DeltaX& > 0 THEN Theata1 = Theata1 + PIE
        IF (Theata1 - Theata) > PIE THEN
     Theata1 = Theata1 - Pie2
    ELSEIF (Theata - Theata1) > PIE THEN Theata1 = Theata1 + Pie2
        END IF
        IF ABS(Theata - Theata1) < Delta THEN
     Theata = Theata1
        ELSE
        IF Theata > Theata1 THEN
            Theata = Theata - Delta
        ELSE
            Theata = Theata + Delta
        END IF
           END IF
      LOOP WHILE ABS(DeltaX&) > MinStep OR ABS(DeltaY&) > MinStep
      PtSaw%(0, Index%) = 200    'TEMPARAY, SO THAT IT IS NOT PICKED AGAIN
ELSE
    Y1& = 0: X1& = 0           'CHECK TO MAKE SURE THAT WAS THE LAST TEST PT
    Index% = ClosElement(X1&, Y1&, VARSEG(PtSaw%(Eye%, 1)), VARPTR(PtSaw%(Eye%, 1)
), VARSEG(PossibleS&(1, 0)), VARPTR(PossibleS&(1, 0)), MinDistance)
    Y1& = 0: X1& = 0
    IF Index% > 0 THEN
        X& = X& + MinDistance * COS(Theata)
        Y& = Y& + MinDistance * SIN(Theata)
    END IF
END IF
X& = X& + MaxStep * COS(Theata)
Y& = Y& + MaxStep * SIN(Theata)
IF SGN(X&) = -1 THEN X& = 0
IF SGN(Y&) = -1 THEN Y& = 0
IF X& > XP THEN X& = XP
IF Y& > YP THEN Y& = YP
RelativeMove (X&), (Y&), Speed, 0
X1& = X&: Y1& = Y&
LOOP WHILE Index% > 0
END SUB
```

```
'==========================================================
'       Procedure TestPts:
'                       This is the main 80 pt test.
'                       mult stimulis method (from 1 to 4 pts at a time).
'                       each pt is presented at its appropriate brightness
'                       as determined by the patient's hill of vision.
'                       Fixation target is continuously moved in a lobed
'                       pattern.
'                       If possible, missed pts are retested within
'                       this procedure.
'                       The number of pts presented each time is randomized
'                       between 1 through 4
'
'==========================================================
'
SUB TestPts
CONST Speed = 1000
CONST Speed2 = 1500
CONST NumLobe = 8                       'number of lobes
CONST LRMin = Xcen \ 10                 'inside lobe radius (ABOUT 10 DEGREES)
CONST LRMax = LRMin + 15000             'outside lobe radius
CONST stepSize = 300                    'interval step size
CONST LobeSize = 2 / 3
CONST LobeSize2 = (1 - LobeSize) / 2
CONST Var1 = Pie2 / NumLobe
CONST Var2 = Var1 / 2
CONST Var3 = Var1 * LobeSize
CONST RightAngle = 80 * Pie180          'SLIGHTLY LESS THE 90 DEGREES
CONST RightAngle3 = 260 * Pie180        '3 X RIGHT ANGLE
R& = (LRMax * SIN(Var1 * LobeSize)) \ 2
R1& = (LRMin * SIN(Var1 * LobeSize2))
AngleStep = (ATN(stepSize / R&)) * 2
AngleStep1 = -(ATN(stepSize / R1&))
RelativeMove (Xcen - LRMin), (Ycen), Speed, 0   'FIRST MOVE!
FOR I% = 0 TO NumLobe - 1               'lobe patern.
Angle1 = Var1 * I%
Angle2 = Angle1 + Var3
'radial of lobe
   Cos1! = COS(Angle1)
   Sin1! = SIN(Angle1)
   FOR II% = LRMin TO LRMax STEP stepSize
   MovelandLed (Xcen - II% * Cos1!), (Ycen + II% * Sin1!), Speed, 0
   NEXT
'top of lobe
   AveAngle = (Angle1 + Angle2) / 2
   CurveX& = Xcen - LRMax * COS(AveAngle)
   CurveY& = Ycen + LRMax * SIN(AveAngle)
   TempA1 = AveAngle - RightAngle
   TempA2 = AveAngle + RightAngle
   FOR Ang = TempA1 TO TempA2 STEP AngleStep
      MovelandLed (CurveX& - R& * COS(Ang)), (CurveY& + R& * SIN(Ang)), Speed, 0
   NEXT
'Radial of lobe
   Cos2! = COS(Angle2)
   Sin2! = SIN(Angle2)
   FOR II% = LRMax TO LRMin STEP -stepSize
   MovelandLed (Xcen - II% * Cos2!), (Ycen + II% * Sin2!), Speed, 0
   NEXT
'End of lobe
   IF I% = NumLobe - 1 THEN GOTO Ended   'DO NOT DO LAST LOOP AROUND
   AveAngle = AveAngle + Var2
   CurveX& = Xcen - LRMin * COS(AveAngle)
   CurveY& = Ycen + LRMin * SIN(AveAngle)
   TempA1 = AveAngle + RightAngle3
   TempA2 = AveAngle + RightAngle
   FOR Ang = TempA1 TO TempA2 STEP AngleStep1
      MovelandLed (CurveX& - R1& * COS(Ang)), (CurveY& + R1& * SIN(Ang)), Speed2, 0
   NEXT
```

```
NEXT
Ended:
    TestMissedPts (Xcen - LRMin * Cos2!), (Ycen + LRMin * Sin2!)
    DisplayResults
END SUB '===============================================================
'
' Procedure: TurnAround
'
'===============================================================
'
SUB TurnAround (X&, Y&, StepSizeX%, StepSizeY%, Speed%)

CONST MaxSteps = 5

'Ramp down
    FOR I% = 1 TO MaxSteps
        RelativeMove (X& + I% * StepSizeX%), (Y& + I% * StepSizeY%), (Speed% + (Spe
ed% * I%) \ 3), 0
    NEXT 'Ramp up  (much slower then procedure RampUp)
    FOR I% = MaxSteps TO 1 STEP -1
        RelativeMove (X& + I% * StepSizeX%), (Y& + I% * StepSizeY%), (Speed% + (Spe
ed% * I%) \ 3), 0
    NEXT
END SUB
```

APPENDIX 3

DOME PATTERN
FIRST PASS
99 PT. FIELD
FEB 22, 1988

CIRCLE CENTER
X= 10752
Y= 10016

| LEFT EYE | | LEFT EYE TARGET OFFSET | | TARGET POSITION | |
|---|---|---|---|---|---|
| CIRCLE | RADIAL | X | Y | X | Y |
| 5 | 20 | 481 | 175 | 11232 | 10176 |
| 5 | 60 | 256 | 443 | 11008 | 10464 |
| 5 | 110 | -175 | 481 | 10592 | 10496 |
| 5 | 160 | -481 | 175 | 10272 | 10176 |
| 5 | 200 | -481 | -175 | 10272 | 9856 |
| 5 | 250 | -175 | -481 | 10592 | 9536 |
| 5 | 290 | 175 | -481 | 10912 | 9536 |
| 5 | 340 | 481 | -175 | 11232 | 9856 |
| 10 | 15 | 989 | 265 | 11744 | 10272 |
| 10 | 50 | 658 | 784 | 11424 | 10816 |
| 10 | 75 | 265 | 989 | 11008 | 11008 |
| 10 | 105 | -265 | 989 | 10496 | 11008 |
| 10 | 135 | -724 | 724 | 10016 | 10752 |
| 10 | 165 | -989 | 265 | 9760 | 10272 |
| 10 | 195 | -989 | -265 | 9760 | 9760 |
| 10 | 225 | -724 | -724 | 10016 | 9280 |
| 10 | 255 | -265 | -989 | 10496 | 9024 |
| 10 | 285 | 265 | -989 | 11008 | 9024 |
| 10 | 315 | 724 | -724 | 11488 | 9280 |
| 10 | 345 | 989 | -265 | 11744 | 9760 |
| 15 | 10 | 1513 | 267 | 12256 | 10272 |
| 15 | 30 | 1330 | 768 | 12096 | 10784 |
| 15 | 45 | 1086 | 1086 | 11840 | 11104 |
| 15 | 60 | 768 | 1330 | 11520 | 11360 |
| 15 | 80 | 267 | 1513 | 11008 | 11520 |
| 15 | 100 | -267 | 1513 | 10496 | 11520 |
| 15 | 120 | -768 | 1330 | 9984 | 11360 |
| 15 | 135 | -1086 | 1086 | 9664 | 11104 |

| | | | | | |
|---|---|---|---|---|---|
| 15 | 150 | | -1330 | 768 | 9408 | 10784 |
| 15 | 210 | | -1330 | -768 | 9408 | 9248 |
| 15 | 225 | | -1086 | -1086 | 9664 | 8928 |
| 15 | 240 | | -768 | -1330 | 9984 | 8672 |
| 15 | 260 | | -267 | -1513 | 10496 | 8512 |
| 15 | 280 | | 267 | -1513 | 11008 | 8512 |
| 15 | 300 | | 768 | -1330 | 11520 | 8672 |
| 15 | 315 | | 1086 | -1086 | 11840 | 8928 |
| 15 | 330 | | 1330 | -768 | 12096 | 9248 |
| 15 | 350 | | 1513 | -267 | 12256 | 9760 |
| 20 | 10 | | 2017 | 356 | 12768 | 10368 |
| 20 | 30 | | 1774 | 1024 | 12512 | 11040 |
| 20 | 60 | | 1024 | 1774 | 11776 | 11776 |
| 20 | 80 | | 356 | 2017 | 11104 | 12032 |
| 20 | 100 | | -356 | 2017 | 10400 | 12032 |
| 20 | 120 | | -1024 | 1774 | 9728 | 11776 |
| 20 | 150 | | -1774 | 1024 | 8992 | 11040 |
| 20 | 210 | | -1774 | -1024 | 8992 | 8992 |
| 20 | 240 | | -1024 | -1774 | 9728 | 8256 |
| 20 | 260 | | -356 | -2017 | 10400 | 8000 |
| 20 | 280 | | 356 | -2017 | 11104 | 8000 |
| 20 | 300 | | 1024 | -1774 | 11776 | 8256 |
| 20 | 330 | | 1774 | -1024 | 12512 | 8992 |
| 20 | 350 | | 2017 | -356 | 12768 | 9664 |
| 25 | 165 | | -2473 | 663 | 8288 | 10688 |
| 25 | 195 | | -2473 | -663 | 8288 | 9344 |
| 30 | 10 | | 3025 | 533 | 13792 | 10560 |
| 30 | 45 | | 2172 | 2172 | 12928 | 12192 |
| 30 | 80 | | 533 | 3025 | 11296 | 13056 |
| 30 | 100 | | -533 | 3025 | 10208 | 13056 |
| 30 | 135 | | -2172 | 2172 | 8576 | 12192 |
| 30 | 225 | | -2172 | -2172 | 8576 | 7840 |
| 30 | 260 | | -533 | -3025 | 10208 | 6976 |
| 30 | 280 | | 533 | -3025 | 11296 | 6976 |
| 30 | 315 | | 2172 | -2172 | 12928 | 7840 |
| 30 | 350 | | 3025 | -533 | 13792 | 9472 |
| 40 | 45 | | 2896 | 2896 | 13664 | 12928 |
| 40 | 80 | | 711 | 4034 | 11456 | 14048 |
| 40 | 100 | | -711 | 4034 | 10048 | 14048 |
| 40 | 135 | | -2896 | 2896 | 7840 | 12928 |
| 40 | 165 | | -3956 | 1060 | 6784 | 11072 |
| 40 | 175 | * | -4080 | 357 | 6656 | 10368 |
| 40 | 185 | * | -4080 | -357 | 6656 | 9664 |
| 40 | 195 | | -3956 | -1060 | 6784 | 8960 |
| 40 | 225 | | -2896 | -2896 | 7840 | 7104 |
| 40 | 260 | | -711 | -4034 | 10048 | 5984 |
| 40 | 280 | | 711 | -4034 | 11456 | 5984 |
| 40 | 315 | | 2896 | -2896 | 13664 | 7104 |
| 45 | 10 | | 4538 | 800 | 15296 | 10816 |
| 45 | 350 | | 4538 | -800 | 15296 | 9216 |
| 50 | 150 | * | -4434 | 2560 | 6304 | 12576 |
| 50 | 170 | * | -5042 | 889 | 5696 | 10912 |
| 50 | 190 | * | -5042 | -889 | 5696 | 9120 |
| 50 | 200 | * | -4811 | -1751 | 5952 | 8256 |
| 55 | 80 | | 978 | 5546 | 11744 | 15552 |
| 55 | 100 | | -978 | 5546 | 9760 | 15552 |
| 60 | 10 | * | 6051 | 1067 | 16800 | 11072 |
| 60 | 165 | | -5935 | 1590 | 4832 | 11616 |
| 60 | 175 | * | -6121 | 535 | 4640 | 10560 |
| 60 | 185 | * | -6121 | -535 | 4640 | 9472 |
| 60 | 195 | | -5935 | -1590 | 4832 | 8416 |
| 60 | 225 | | -4344 | -4344 | 6400 | 5664 |
| 60 | 350 | * | 6051 | -1067 | 16800 | 8960 |
| 70 | 175 | * | -7141 | 625 | 3616 | 10656 |
| 70 | 185 | * | -7141 | -625 | 3616 | 9376 |
| 80 | 160 | | -7698 | 2802 | 3040 | 12832 |
| 80 | 170 | | -8068 | 1423 | 2688 | 11424 |
| 80 | 175 | | -8161 | 714 | 2592 | 10720 |
| 80 | 185 | | -8161 | -714 | 2592 | 9312 |
| 80 | 190 | | -8068 | -1423 | 2688 | 8608 |
| 80 | 200 | | -7698 | -2802 | 3040 | 7200 |

TABLE 12

PARALLEL PSEUDONOISE SEQUENCIES GENERATOR.

COMPUTATION OF THE TRANSITION MATRIX.( PROGRAM GPSA)
GEORGES ROGER L.D.M. 9/11/88

1) DEGREE OF THE CHARACTERISTIC POLYNOMIAL    (1<P<13)? 7
DEGRE DU POLYNOME CARACTERISTIQUE:  7

INPUT OF THE CHARACTERISTIC POLYNOMIAL.

POLYNOMIALSS ARE WRITTEN AS:
X0 + A1 X1 + A2 X2 + .... + AP-1 XP-1 +XP
 PLEASE GIVE THE RANK OF COEFFICIENTS A1 TO AP-1 EQUAL TO 1,  ONE AFTER THE OTHER.
 (THOSE OF DEGREE 0 AND P ARE  EQUAL TO  1 ALREADY)
  INPUT 0 TO INDICATE THE END OF THE OPERATION.

RANK OF A COEFFICIENT EQUAL TO 1 ? 6
RANK OF A COEFFICIENT EQUAL TO 1 ? 0

CHARACTERISTIC POLYNOMIAL: : Z0  Z6  Z7

OK? :(RETURN=YES, IF NOT, INPUT: N ) Y

PERIODE TROUVEE POUR SEQ1:    127  PERIODE MAX:    127
SEQ1: 1111111000000100000110000101000111100100010110011101010011111101000011100

2) NUMBER OF SIMULTANEOUS BITS    (N>P-1)? 8

OK? :(RETURN=YES, IF NOT, INPUT: N ) Y

*****************************
DEGREE OF CHARACTERISTIC POLYNOMIAL :  7

CHARACTERISTIC POLYNOMIAL : Z0  Z6  Z7

NB OF SIMULTANEOUS BITS:    8

COMPUTING .....
*****************************
SEQ1: 1111111000000100000110000101000111100100010110011101010011111101000011100
SEQ2: 1111111000000100000110000101000111100100010110011101010011111101000011100

JOB TERMINATED.RESULTS IN GPSA.DAT
  DEGREE OF CHARACTERISTIC POLYNOMIAL :   7

CHARACTERISTIC POLYNOMIAL : Z0  Z6  Z7

NB OF SIMULTANEOUS BITS:    8

RN07 : Z5  Z6
 RN06 : Z4  Z5
 RN05 : Z3  Z4
 RN04 : Z2  Z3
 RN03 : Z1  Z2
 RN02 : Z0  Z1
 RN01 : Z5  Z7
 RN00 : Z4  Z6

```
************************************
DEGREE OF CHARACTERISTIC POLYNOMIAL : 7

CHARACTERISTIC POLYNOMIAL  : Z0  Z6  Z7

NB OF SIMULTANEOUS BITS:   8

************************************

MATRIX:

0 0 0 0 0 0 0 0
        0 1 2 3 4 5 6 7

0   - - - - + - + -
    1   - - - - - + - +
    2   + + - - - - - -
    3   - + + - - - - -
    4   - - + + - - - -
    5   - - - + + - - -
    6   - - - - + + - -
    7   - - - - - + + -
```

TABLE 13

```
************************************
DEGREE OF CHARACTERISTIC POLYNOMIAL.: 7

CHARACTERISTIC POLYNOMIAL  : Z0  Z6  Z7

NB OF SIMULTANEOUS BITS:   8

************************************

MATRIX:

0 0 0 0 0 0 0 0
        0 1 2 3 4 5 6 7

0   - - - - + - + -
    1   - - - - - + - +
    2   + + - - - - - -
    3   - + + - - - - -
    4   - - + + - - - -
    5   - - - + + - - -
    6   - - - - + + - -
    7   - - - - - + + -

VERIFICATION O.K.  !!!

RN07 : Z5  Z6
RN06 : Z4  Z5
RN05 : Z3  Z4
RN04 : Z2  Z3
RN03 : Z1  Z2
RN02 : Z0  Z1
RN01 : Z5  Z7
RN00 : Z4  Z6
```

MATRIX:

```
     0 0 0 0 0 0 0 0 0 0 1 1 1 1 1 1
     0 1 2 3 4 5 6 7 8 9 0 1 2 3 4 5

0   - - - - - - - - + - - - + - - -
 1   - - - - - - - - - + - - - + - -
 2   - - - - - - - - - + - - - - + -
 3   - - - - - - - - - - - - - - - +
 4   + - + - - - - - - - - - - - - -
 5   - + - + - - - - - - - - - - - -
 6   - - + - + - - - - - - - - - - -
 7   - - - + - + - - - - - - - - - -
 8   - - - - + - + - - - - - - - - -
 9   - - - - - + - + - - - - - - - -
10   + + - - - - - - - - - - - - - -
11   - + + - - - - - - - - - - - - -
12   - - + + - - - - - - - - - - - -
13   - - - + + - - - - - - - - - - -
14   - - - - + + - - - - - - - - - -
15   - - - - - + + - - - - - - - - -
```

VERIFICATION O.K. !!!

```
RN15 : Z5   Z6
RN14 : Z4   Z5
RN13 : Z3   Z4
RN12 : Z2   Z3
RN11 : Z1   Z2
RN10 : Z0   Z1
RN09 : Z5   Z7
RN08 : Z4   Z6
RN07 : Z3   Z5
RN06 : Z2   Z4
RN05 : Z1   Z3
RN04 : Z0   Z2
RN03 : Z11  Z15
RN02 : Z10  Z14
RN01 : Z9   Z13
RN00 : Z8   Z12

RN23 : Z5   Z6
RN22 : Z4   Z5
RN21 : Z3   Z4
RN20 : Z2   Z3
RN19 : Z1   Z2
RN18 : Z0   Z1
RN17 : Z5   Z7
RN16 : Z4   Z6
RN15 : Z3   Z5
RN14 : Z2   Z4
RN13 : Z1   Z3
RN12 : Z0   Z2
RN11 : Z11  Z15
RN10 : Z10  Z14
RN09 : Z9   Z13
RN08 : Z8   Z12
RN07 : Z7   Z11
RN06 : Z6   Z10
RN05 : Z5   Z9
RN04 : Z4   Z8
RN03 : Z3   Z7
RN02 : Z2   Z6
RN01 : Z1   Z5
RN00 : Z0   Z4
```

MATRIX:

|    | 00 | 01 | 02 | 03 | 04 | 05 | 06 | 07 | 08 | 09 | 10 | 11 | 12 | 13 | 14 | 15 | 16 | 17 | 18 | 19 | 20 | 21 | 22 | 23 |
|----|----|----|----|----|----|----|----|----|----|----|----|----|----|----|----|----|----|----|----|----|----|----|----|----|
| 0  | +  | -  | -  | -  | +  | -  | -  | -  | -  | -  | -  | -  | -  | -  | -  | -  | -  | -  | -  | -  | -  | -  | -  | -  |
| 1  | -  | +  | -  | -  | -  | +  | -  | -  | -  | -  | -  | -  | -  | -  | -  | -  | -  | -  | -  | -  | -  | -  | -  | -  |
| 2  | -  | -  | +  | -  | -  | -  | +  | -  | -  | -  | -  | -  | -  | -  | -  | -  | -  | -  | -  | -  | -  | -  | -  | -  |
| 3  | -  | -  | -  | +  | -  | -  | -  | +  | -  | -  | -  | -  | -  | -  | -  | -  | -  | -  | -  | -  | -  | -  | -  | -  |
| 4  | -  | -  | -  | -  | +  | -  | -  | -  | +  | -  | -  | -  | -  | -  | -  | -  | -  | -  | -  | -  | -  | -  | -  | -  |
| 5  | -  | -  | -  | -  | -  | +  | -  | -  | -  | +  | -  | -  | -  | -  | -  | -  | -  | -  | -  | -  | -  | -  | -  | -  |
| 6  | -  | -  | -  | -  | -  | -  | +  | -  | -  | -  | +  | -  | -  | -  | -  | -  | -  | -  | -  | -  | -  | -  | -  | -  |
| 7  | -  | -  | -  | -  | -  | -  | -  | +  | -  | -  | -  | +  | -  | -  | -  | -  | -  | -  | -  | -  | -  | -  | -  | -  |
| 8  | -  | -  | -  | -  | -  | -  | -  | -  | +  | -  | -  | -  | +  | -  | -  | -  | -  | -  | -  | -  | -  | -  | -  | -  |
| 9  | -  | -  | -  | -  | -  | -  | -  | -  | -  | +  | -  | -  | -  | +  | -  | -  | -  | -  | -  | -  | -  | -  | -  | -  |
| 10 | -  | -  | -  | -  | -  | -  | -  | -  | -  | -  | +  | -  | -  | -  | +  | -  | -  | -  | -  | -  | -  | -  | -  | -  |
| 11 | -  | -  | -  | -  | -  | -  | -  | -  | -  | -  | -  | +  | -  | -  | -  | +  | -  | -  | -  | -  | -  | -  | -  | -  |
| 12 | +  | -  | +  | -  | -  | -  | -  | -  | -  | -  | -  | -  | -  | -  | -  | -  | -  | -  | -  | -  | -  | -  | -  | -  |
| 13 | -  | +  | -  | +  | -  | -  | -  | -  | -  | -  | -  | -  | -  | -  | -  | -  | -  | -  | -  | -  | -  | -  | -  | -  |
| 14 | -  | -  | +  | -  | +  | -  | -  | -  | -  | -  | -  | -  | -  | -  | -  | -  | -  | -  | -  | -  | -  | -  | -  | -  |
| 15 | -  | -  | -  | +  | -  | +  | -  | -  | -  | -  | -  | -  | -  | -  | -  | -  | -  | -  | -  | -  | -  | -  | -  | -  |
| 16 | -  | -  | -  | -  | +  | -  | +  | -  | -  | -  | -  | -  | -  | -  | -  | -  | -  | -  | -  | -  | -  | -  | -  | -  |
| 17 | -  | -  | -  | -  | -  | +  | -  | +  | -  | -  | -  | -  | -  | -  | -  | -  | -  | -  | -  | -  | -  | -  | -  | -  |
| 18 | +  | +  | -  | -  | -  | -  | -  | -  | -  | -  | -  | -  | -  | -  | -  | -  | -  | -  | -  | -  | -  | -  | -  | -  |
| 19 | -  | +  | +  | -  | -  | -  | -  | -  | -  | -  | -  | -  | -  | -  | -  | -  | -  | -  | -  | -  | -  | -  | -  | -  |
| 20 | -  | -  | +  | +  | -  | -  | -  | -  | -  | -  | -  | -  | -  | -  | -  | -  | -  | -  | -  | -  | -  | -  | -  | -  |
| 21 | -  | -  | -  | +  | +  | -  | -  | -  | -  | -  | -  | -  | -  | -  | -  | -  | -  | -  | -  | -  | -  | -  | -  | -  |
| 22 | -  | -  | -  | -  | +  | +  | -  | -  | -  | -  | -  | -  | -  | -  | -  | -  | -  | -  | -  | -  | -  | -  | -  | -  |
| 23 | -  | -  | -  | -  | -  | +  | +  | -  | -  | -  | -  | -  | -  | -  | -  | -  | -  | -  | -  | -  | -  | -  | -  | -  |

VERIFICATION O.K. !!!

```
RN31 : Z5   Z6
RN30 : Z4   Z5
RN29 : Z3   Z4
RN28 : Z2   Z3
RN27 : Z1   Z2
RN26 : Z0   Z1
RN25 : Z5   Z7
RN24 : Z4   Z6
RN23 : Z3   Z5
RN22 : Z2   Z4
RN21 : Z1   Z3
RN20 : Z0   Z2
RN19 : Z11  Z15
RN18 : Z10  Z14
RN17 : Z9   Z13
RN16 : Z8   Z12
RN15 : Z7   Z11
RN14 : Z6   Z10
RN13 : Z5   Z9
RN12 : Z4   Z8
RN11 : Z3   Z7
RN10 : Z2   Z6
RN09 : Z1   Z5
RN08 : Z0   Z4
RN07 : Z1   Z18
RN06 : Z0   Z17
RN05 : Z8   Z26
RN04 : Z7   Z25
RN03 : Z6   Z24
RN02 : Z5   Z23
RN01 : Z4   Z22
RN00 : Z3   Z21
```

MATRIX:

```
          0 0 0 0 0 0 0 0 0 0 1 1 1 1 1 1 1 1 1 1 2 2 2 2 2 2 2 2 2 2 3 3
          0 1 2 3 4 5 6 7 8 9 0 1 2 3 4 5 6 7 8 9 0 1 2 3 4 5 6 7 8 9 0 1
    0     - - - + - - - - - - - - - - - - - - - - - + - - - - - - - - - -
    1     - - - - + - - - - - - - - - - - - - - - - - + - - - - - - - - -
    2     - - - - - + - - - - - - - - - - - - - - - - - + - - - - - - - -
    3     - - - - - - + - - - - - - - - - - - - - - - - - + - - - - - - -
    4     - - - - - - - + - - - - - - - - - - - - - - - - - + - - - - - -
    5     - - - - - - - - + - - - - - - - - - - - - - - - - - + - - - - -
    6     + - - - - - - - - - - - - - - - + - - - - - - - - - - - - - - -
    7     - + - - - - - - - - - - - - - - - + - - - - - - - - - - - - - -
    8     + - - - - - - - - - - - - - - - - - + - - - - - - - - - - - - -
    9     - + - - - + - - - - - - - - - - - - - + - - - - - - - - - - - -
   10     - - + - - - + - - - - - - - - - - - - - + - - - - - - - - - - -
   11     - - - + - - - + - - - - - - - - - - - - - + - - - - - - - - - -
   12     - - - - + - - - + - - - - - - - - - - - - - + - - - - - - - - -
   13     - - - - - + - - - + - - - - - - - - - - - - - + - - - - - - - -
   14     - - - - - - + - - - + - - - - - - - - - - - - - + - - - - - - -
   15     - - - - - - - + - - - + - - - - - - - - - - - - - + - - - - - -
   16     - - - - - - - - + - - - + - - - - - - - - - - - - - + - - - - -
   17     - - - - - - - - - + - - - + - - - - - - - - - - - - - + - - - -
   18     - - - - - - - - - - + - - - + - - - - - - - - - - - - - + - - -
   19     - - - - - - - - - - - + - - - + - - - - - - - - - - - - - + - -
   20     + - + - - - - - - - - - - - - - - - - - - - - - - - - - - - - -
   21     - + - + - - - - - - - - - - - - - - - - - - - - - - - - - - - -
   22     - - + - + - - - - - - - - - - - - - - - - - - - - - - - - - - -
   23     - - - + - + - - - - - - - - - - - - - - - - - - - - - - - - - -
   24     - - - - + - + - - - - - - - - - - - - - - - - - - - - - - - - -
   25     - - - - - + - + - - - - - - - - - - - - - - - - - - - - - - - -
   26     - - - - - - + - + - - - - - - - - - - - - - - - - - - - - - - -
   27     - + + - - - - - - - - - - - - - - - - - - - - - - - - - - - - -
   28     - - + + - - - - - - - - - - - - - - - - - - - - - - - - - - - -
   29     - - - + + - - - - - - - - - - - - - - - - - - - - - - - - - - -
   30     - - - - + + - - - - - - - - - - - - - - - - - - - - - - - - - -
   31     - - - - - + + - - - - - - - - - - - - - - - - - - - - - - - - -
```

VERIFICATION O.K. !!!

```
RN63 : Z5   Z6
RN62 : Z4   Z5
RN61 : Z3   Z4
RN60 : Z2   Z3
RN59 : Z1   Z2
RN58 : Z0   Z1
RN57 : Z5   Z7
RN56 : Z4   Z6
RN55 : Z3   Z5
RN54 : Z2   Z4
RN53 : Z1   Z3
RN52 : Z0   Z2
RN51 : Z11  Z15
RN50 : Z10  Z14
RN49 : Z9   Z13
RN48 : Z8   Z12
RN47 : Z7   Z11
RN46 : Z6   Z10
RN45 : Z5   Z9
RN44 : Z4   Z8
RN43 : Z3   Z7
RN42 : Z2   Z6
RN41 : Z1   Z5
RN40 : Z0   Z4
RN39 : Z1   Z18
RN38 : Z0   Z17
RN37 : Z8   Z26
RN36 : Z7   Z25
RN35 : Z6   Z24
RN34 : Z5   Z23
RN33 : Z4   Z22
RN32 : Z3   Z21
RN31 : Z2   Z20
RN30 : Z1   Z19
RN29 : Z0   Z18
RN28 : Z13  Z18
RN27 : Z12  Z17
RN26 : Z11  Z16
RN25 : Z10  Z15
RN24 : Z9   Z14
RN23 : Z8   Z13
RN22 : Z7   Z12
RN21 : Z6   Z11
RN20 : Z5   Z10
RN19 : Z4   Z9
RN18 : Z3   Z8
RN17 : Z2   Z7
RN16 : Z1   Z6
RN15 : Z0   Z5
RN14 : Z10  Z13

RN13 : Z9   Z12
RN12 : Z8   Z11
RN11 : Z7   Z10
RN10 : Z6   Z9
RN09 : Z5   Z8
RN08 : Z4   Z7
RN07 : Z3   Z6
RN06 : Z2   Z5
RN05 : Z1   Z4
RN04 : Z0   Z3
RN03 : Z15  Z26
RN02 : Z14  Z25
RN01 : Z13  Z24
RN00 : Z12  Z23
```

13-10

What is claimed is:

1. A reverse kinetic perimetry method of examining the visual sensitivity of a patient's eye comprising:
moving an illuminated first light in order that it may be substantially continuously followed by, and substantially continuously visually fixed to the fovea of, a patient's moving eye;

illuminating at least one second light while it assumes various distances of separation from, and angles relative to, the moving first light;

querying the patient to indicate periods that he/she does and does not visually detect the at least one second light while fixedly visually following the first light, each change in either sense between periods of detection and periods of non-detection constituting a temporal juncture;

computing relative positions, in both distances of separation and relative angles, of the first and of the at least one second lights upon at least some of the temporal junctures; and recording the computed relative positions;

wherein the aggregate recorded relative positions indicate the visual sensitivity of the patient's eye.

2. A modified reverse kinetic perimetry method of examining the visual sensitivity of a patient's eye comprising:

moving an illuminated first light in order that it may be substantially continuously followed by, and substantially continuously visually fixed to the fovea of, a patient's moving eye;

illuminating momentarily at times at least one second light, the at least one second light being at predetermined distances of separation from, and angles relative to, the first light at the times of its momentary illuminations;

querying the patient regarding his/her visual detection or non-detection of the at least one second light upon each of the times of its momentary illumination;

correlating the detections and non-detections with the corresponding distances of separation and angles between the at least one second light and the first light in order to determine a visual sensitivity of the patient's eye to the illuminations.

3. A method of modified reverse kinetic perimetry by successive approximations to determine a point of visual sensitivity upon an island of vision of a patient's eye, the method comprising:

moving an illuminated first light in order that it may be substantially continuously followed by, and substantially continuously visually fixed to the fovea of, a patient's moving eye;

illuminating momentarily at times at least one second light, the at least one second light being at a predetermined distance of separation from, and angle relative to, the first light at the times of its momentary illuminations;

varying the illumination intensity of the at least one second light upon the times of its momentary illuminations to be in successive approximations both suprathreshold and subthreshold to the visual sensitivity of the patient's eye;

querying the patient regarding his/her visual detection or non-detection of the at least one second light upon each of the times of its momentary illumination;

correlating the detections and non-detections with the distance of separation and angle between the first light and that at least one second light at the times of its momentary illuminations each at a successively approximated illumination intensity in order to determine by the correlating a visual sensitivity at a point upon an island of vision of the patient's eye.

4. The method according to claim 1 or claim 2 or claim 3 further expanded for mapping the visual field of the patient's eye, the expanded method comprising:

generating a map of the visual field of the patient's eye by an apparatus that moves a marker;

wherein the same apparatus that moves the marker is used, otherwise and at other times from moving the marker, for the moving of the illuminated first light source.

5. The method according to claim 1 or claim 2 or claim 3 wherein the first light is a single unitary light; and consequently wherein the moving is physically of the single unitary light.

6. The method according to claim 1 or claim 2 or claim 3 wherein the moving is substantially continuous during the recording.

7. The method according to claim 1 or claim 2 or claim 3 wherein the moving is substantially continuous and is substantially uniform in velocity.

8. The method according to claim 2 or claim 3 wherein the momentary illuminatings of the second light are sufficient in numbers and occurring at sufficient different positions relative to the first light so as to adequately survey the entire visual field to the non-seeing boundaries thereof.

9. The method according to claim 2 or claim 3 wherein the illuminating momentarily is simultaneously of a plurality n of second lights; and wherein the querying is of the numbers zero through n of the plurality of second lights which are detected by the patient upon each simultaneous momentary illumination of the plurality n of second lights.

10. The method according to claim 2 or claim 3 wherein the illuminating momentarily is simultaneously of a plurality n of second lights; and wherein the querying is of the numbers zero through n of the plurality of second lights which are detected by the patient upon each simultaneous momentary illumination of the plurality n of second lights; and that after the querying further comprises:

determining if less than the total n of the simultaneous momentary illuminatings of the plurality n of second lights has been detected by the patient and IF all n have been detected THEN continuing with successive simultaneous momentary illuminatings ELSE IF less than n have been detected THEN conducting a binary search by successively momentarily illuminating less than n of the plurality of second lights, each still at the same relative position to the first source of light, until the individual visual detections or non-detections of each of the n second lights are known and recorded.

11. The method according to claim 1 or claim 2 or claim 3 which before the moving further comprises:

calibrating the light output of the at least one second source of light.

12. A reverse kinetic perimetry method of examining the visual sensitivity of a patient's eye comprising:

arranging a plurality of individual light sources at a visual angular separation sufficient to allow a patient's eye having a blind spot at the fovea to fixate upon a geometric center of the plurality of individual light sources:

moving the collective plurality of individual light sources in order that it may be substantially continuously followed by, and substantially continuously visually fixed to the fovea of, a patient's moving eye;

wherein the patient's eye substantially continually fixates the geometric center of the plurality of individual light sources to the fovea even though the patient's eye exhibits a blind spot at this foveal location;

illuminating at least one second light while it assumes various distances of separation from, and angles relative to, the moving plurality of individual light sources;

querying the patient to indicate periods that he/she does and does not visually detect the at least one second light while fixedly visually following the plurality of individual light source, each change in either sense between periods of detection and periods of non-detection constituting a temporal juncture;

computing relative positions, in both distances of separation and relative angles, of the geometric center of the plurality of individual light sources and of the at least one second lights upon at least some of the temporal junctures; and recording the computed relative positions;

wherein the aggregate recorded relative positions indicate the visual sensitivity of the patient's eye.

13. A reverse kinetic perimetry method of examining the visual sensitivity of a patient's eye comprising:

establishing a matrix of a multiplicity of positionally fixed lights;

moving an illuminated first light by stepwise by successively illuminating the multiplicity of lights, the moving of the illuminated first light being so that it maybe substantially continuously followed by, and substantially continuously visually fixed to the fovea of, a patient's moving eye;

illuminating at least one second light while it assumes various distances of separation from, and angles relative to, the moving first light;

querying the patient to indicate periods that he/she does and does not visually detect the at least one second light while fixedly visually following the first light, each change in either sense between periods of detection and periods of non-detection constituting a temporal juncture;

computing relative positions, in both distances of separation and relative angles, of the first and of the at least one second lights upon at least some of the temporal junctures; and recording the computed relative positions;

wherein the aggregate recorded relative positions indicate the visual sensitivity of the patient's eye.

14. An improvement to the kinetic method of surveying and mapping a visual field of a patient's eye by advancing a moving, kinetic, test target from a non-seeing area outside the visual field into the visual field until it is first detected by the patient, defining thereby a location of a visual threshold point, successively repeating the advancing from various directions toward the center of the visual field in order to define a multiplicity of visual threshold point locations, mapping the multiplicity of visual threshold point locations in distance and in angle relative to the center of the visual field for a particular test object, and joining the visual threshold point locations to form an isopter, the improvement comprising:

moving the center of the visual field between successive repeatings; and wherein each of the multiplicity of visual threshold point locations is defined in true distance and in true angle relative to the center of the visual field before the mapping.

15. The improvement to the kinetic method of surveying and mapping the visual field according to claim 14 wherein the center of the visual field is demarked by an illuminated source of light.

16. The improvement to the kinetic method of surveying and mapping the visual field according to claim 15 wherein the source of light is a single unitary light; and consequently wherein the moving is physically of the single unitary light.

17. The improvement to the kinetic method of surveying and mapping the visual field according to claim 15 wherein the source of light is a matrix of a multiplicity of positionally fixed lights; and consequently wherein the moving is stepwise by successive illuminatings amongst the multiplicity of lights.

18. The improvement to the kinetic method of surveying and mapping the visual field according to claim 14 wherein the mapping of the visual threshold points is accomplished by a same apparatus, otherwise and otherwhiles employed, that is used for the moving of the center of the visual field.

19. In a method of performing ocular threshold perimetry by fixing a patient's eye upon a first light source while increasing the intensity of a second light source, located at different times at various distances of separation and various angles relative to the first light source, until either the patient indicates that the second light source is incipiently detected or else, the second light source being outside of the field of vision or within a blind spot of the patient's eye, that the second light source is undetectable no matter how bright, and plotting the intensity of the second light source at its incipient detections versus the relative distances of separation and relative angles relative to the first light source at all such incipient detections as a representation of the visual acuity of the patient's eye, an improvement comprising:

locating the second light source at its various distances of separation at its various angels upon the different times by an action of moving the first light source, and by a corresponding action of moving the patient's eye fixation thereto, instead of by any action of moving the second light source; and wherein the locating of the second light source relative to first light source by the action of moving the first light source is automated, meaning that the patient does not have to move his/her fixation from a one first source to a next in order to simulate movement thereof, and neither is the patient required to participate in moving the first light source, but rather the patient need only visually fixate the first light source, which first light source physically moves under automated control.

20. A reversal of the kinetic perimetry method of visual field examination wherein a test target stimulus is moved into the visual field of a patient's eye that is fixating on a positionally fixed reference stimulus, the reversed method comprising:

fixing the position of a test target stimulus, and moving a reference stimulus so that it followed by and visually fixed by a patient's moving eye;

wherein the target stimulus is initially outside a visual field of the patient's eye at an initial position of the reference stimulus but moves into the visual field during moving of the reference stimulus;

wherein the fixing and the moving permit testing to at least 60° in the nasal direction despite the presence of the patient's nose, to at least 60° superiorly despite the presence of the patient's brow, and to at least 75° inferiorly despite the presence of the patient's cheek.

21. The reversed kinetic perimetry method of visual field examination according to claim 20 wherein the fixing and the moving allow testing of at least 90° in each of the nasal, superior, and inferior directions despite the presence of the patient's nose, brow, and cheek.

22. The reversed kinetic perimetry method of visual field examination according to claim 20 wherein the moving is automated.

23. The reversed kinetic perimetry method of visual field examination according to claim 20 wherein the test target stimulus is fixed and the reference target stimulus is moved on a target plane.

24. A modified kinetic perimetry method of visual field examination that is not limited in a determination of the maximum extent of a patient's visual field in the nasal direction by the patient's nose, nor in the superior direction by the patient's brow, nor in the interior direction by the patient's cheek, the modified kinetic method of determining the maximum extent of a patient's visual field despite the patient's facial anatomy comprising:

fixing a target stimulus of separate times at respective (i) nasal, (ii) superior, and (iii) inferior points;

moving a reference stimulus that is fixated by the patient's eye respectively (i) from a temporal position whereat the nasal stimulus point is not within the patient's visual field due to the patient's nose in a nasal direction until the patient's visual field crosses into the nasal stimulus point, (ii) from an inferior position whereat the superior stimulus point is not within the patient's visual field due to the patient's brow in a superior direction until the patient's visual field crosses into the superior stimulus point, and (iii) from a superior position whereat the inferior stimulus point is not within the patient's visual field due to the patient's cheek in an inferior direction until the patient's visual field crosses into the inferior stimulus point;

wherein the angular operation of the respective stimulus points and the reference stimulus at the respective crossings represent the maximum extent of the patient's visual field respectively in the nasal, superior, and inferior directions.

25. The modified kinetic perimetry method according to claim 24 wherein the moving is automated.

26. The modified kinetic perimetry method according to claim 24 wherein each target stimulus and the reference stimulus is upon a plane.

27. An instrument for testing the human visual field comprising:

a first light illuminated and moving so as to be followed by a patient's eye;

at least one second light selectively illuminating at various positions relative to the first light;

a stimuli response recorder for recording the response of the patient that, while fixating on the moving first light source with the eye, each selective illumination of the at least one second light source either was or was not seen;

wherein the cumulative recorded stimuli responses are indicative of the visual field of the patient's eye.

28. The instrument according to claim 27 wherein the first light and the at least one second light are rear projected upon a tangent screen.

29. The instrument according to claim 27 further comprising:

a computer controlling both the first light's moving and the second light's selective illumination.

30. An apparatus for visual field examination comprising:

a means for fixing a test target stimulus; and a means for moving a reference stimulus so that is followed by a patient's moving eye;

wherein the target stimulus is initially fixed by the fixing means outside the visual field from the initial reference stimulus position but is moved by the moving means into the visual field during moving of the reference stimulus;

wherein the means for fixing and the means for moving allow testing to at least 60° in the nasal direction despite the presence of the patient's nose, to at least 60° superiorly despite the presence of the patient's brow, and to at least 75° inferiorly despite the presence of the patient's cheek.

31. The apparatus for visual field examination according to claim 30 wherein the means for fixing and the means for moving allow testing to at least 90° in each of the nasal, superior, and inferior directions despite the presence of the patient's nose, brow, and cheek.

32. The apparatus for visual field examination according to claim 30 wherein the means for moving is automated under computer control.

33. The apparatus for visual field examination according to claim 30 further comprising:

a tangent plane upon which the test target stimulus is fixed by the means for fixing, and upon which the reference target stimulus is moved by the means for moving.

34. The apparatus for visual field examination according to claim 30 wherein the means for fixing the test target stimuli comprises:

a plurality of light sources positionally fixed by a frame; and wherein the means for moving the reference stimulus comprises:

a light source moved relative to the frame by an x-y plotter.

35. An apparatus for visual field examination that is not limited in a determination of the maximum extent of a patient's visual field in the nasal direction by the patient's nose nor in the superior direction by the patient's brow, nor in the inferior direction by the patient's cheek, the apparatus for determining the maximum extent of a patient's visual field despite the patient's facial anatomy comprising:

inanimate means for fixing a target stimulus at separate times at respective (i) nasal, (ii) superior, and (iii) inferior points;

inanimate means for moving a reference stimulus that is fixated by the patient's eye respectively (i) from a temporal position whereat the nasal stimulus point is not within the patient's visual field due to the patient's nose in a nasal direction until the patient's visual field crosses into the nasal stimulus point, (ii) from an inferior position whereat the superior stimulus point is not within the patient's visual field due to the patient's brow in a superior direction until the patient's visual field crosses into the superior stimulus point, and (iii) from a superior position whereat the inferior stimulus point is not within the patient's visual field due to the patient's cheek in an inferior direction until the patient's visual field crosses into the inferior stimulus point;

wherein the angular operations of the respective stimulus points and the reference stimulus at the respective crossings represent the maximum extent of the patient's visual field respectively in the nasal, superior, and interior directions.

36. The apparatus according to claim 35 further comprising:

a computer automating the moving of the reference stimulus by the means for moving.

37. The apparatus according to claim 35 wherein the means for fixing a target stimulus comprises:

a plurality of light sources; and a frame positionally fixing the plurality of light sources;

wherein the fixing of the target stimulus is by the illumination of a selected one of the plurality of positionally fixed light sources.

38. The apparatus according to claim 35 wherein the means for moving a reference stimulus comprises:

a light source; and an x-y plotter for moving the light source as its positionally moveable element.

39. A method of examining the visual sensitivity of the eye comprising:

simultaneously presenting a plurality of illuminated light sources at positions and intensities that are potentially detectable within the visual field of a patient's eye; and querying the patient for his/her voiced response as to the number of the plurality of simultaneously illuminated light sources that the patient visually detects;

interpreting the voiced response in a voice recognition system to produce a digital quantity representative of the particular number spoken;

computing in a digital computer in consideration of the positions and intensities of the presented light sources, and the digital quantity of the number of such light sources, the visual field of the patient's eye.

40. An apparatus for examining the visual sensitivity of a patient's eye comprising:

a first source of light;

means for moving the first light in order that it may be substantially continuously followed by, and substantially continuously visually fixed to the fovea of, the patient's moving eye;

a second source of light assuming various distances of separation from, and angles relative to, the moving first source of light;

means for querying the patient to indicate periods that he/she does and does not visually detect the second light source while fixedly visually following the first light source, each change in either sense between periods of detection and periods of non-detection constituting a temporal juncture;

computer means, connected to the means for querying to receive the temporal juncture information and to the means for moving in order to know the position of the first light source, for calculating the relative positions, in both distances of separation and relative angles, of the first and of the second sources of light upon at least some of the temporal junctures;

recording means, connected to the computer means to receive the calculated relative positions, for recording the relative positions;

wherein the aggregate recorded relative positions indicate the visual sensitivity of the patient's eye.

41. An apparatus for examining the visual sensitivity of a patient's eye comprising:

a first source of light;

means for controllably moving the first source of light in order that it may be substantially continuously followed by, and substantially continuously visually fixed to the fovea of, the patient's moving eye;

a second source of light controllable for illuminating momentarily at times means for detecting the visual detection or non-detection by the patient of the second light upon each of the times of its momentary illumination;

computer means, connected to the means for controllably moving and to the second source of light and to the means for detecting, for controlling the means for controllably moving so that the position of the first source of light is known, for controlling the momentary illuminating of the second source of light at times when it is at predetermined distances of separation from, and angles relative to, the moving first source of light, and for calculating in consideration of the visual detections or non-detections at the times of the momentary illuminatings at the predetermined distances of separation, and angles, of the second source of light relative to the first source of light the visual sensitivity of the patient's eye;

recording means, connected to the computer for receiving the calculated visual sensitivity, for recording the calculated visual sensitivity.

42. An apparatus for determining a point of visual sensitivity upon the island of vision, the apparatus comprising:

a first source of light;

means for moving the first source of light in order that it may be substantially continuously followed by, and substantially continuously visually fixed to the fovea of, the patient's moving eye;

at least one second light illuminating momentarily at times, the second light being at a predetermined distance of separation from, and predetermined angle relative to, the first source of light at the times of its momentary illuminations;

control means connected to the at least one second light, for varying the illumination intensity of the at least one second light upon the times of its momentary illuminations to be in successive approximations both suprathreshold and subthreshold to the visual field of the patient'eye;

means for sensing the visual detection or non-detection by the patient of the at least one second light upon each of the times of its momentary illumination;

computer means, connected to the means for moving in order to know the position of the moving first source of light and to the control means in order to know the illumination intensity of the at least one second souree of light and to the means for sensing in order to know the patient's detection or non-detection, for correlating the recorded detections and non-detections with the distance of separation and angle between the at least one second light and the first source of light at the times of the momentary illuminations at each of the successively approximated illumination intensities in order to determine a visual sensitivity of the patient's eye at a point upon the island of vision of such patient's eye; and recording means, connected to the computer means for receiving the calculated visual sensitivity of the patient's eye, for recording the calculated visual sensitivity.

43. The apparatus according to claim 40 or claim 41 or claim 42 wherein the first source of light comprises:
a single unitary light;
wherein the means for moving is physically moving the single unitary light.

44. The apparatus according to claim 42 wherein the first source of light comprises:
a plurality of individual light sources at a visual angular separation sufficient to allow a patient's eye having a blind spot at the fovea to fixate upon a geometric center of the plurality of individual light sources;
wherein the means for moving is collectively moving the plurality of individual light sources;
wherein the patient's eye substantially continually fixates the geometric center of the first light to the fovea even though the patient's eye exhibits a blind spot at this foveal location.

45. The apparatus according to claim 42 wherein the first source of light comprises:
matrix of a multiplicity of positionally fixed lights;
wherein the means for moving is stepwise successively illuminating ones of the multiplicity of lights.

46. The apparatus according to claim 42 further comprising:
means for calibrating the light output of the second source of light.

47. Apparatus for determining a point of visual sensitivity upon the island of vision; and for mapping the visual field of the patient's eye, the apparatus comprising:
a first source of light;
means for moving the first source of light in order that it may be substantially continuously followed by, and substantially continuously visually fixed to the fovea of, the patient's moving eye;
at least one second light illuminating momentarily at times the second light being at a predetermined distance of separation from, and angle relative to, the first source of light at the times of its momentary illuminations;

control means connected to the at least one second light, for varying the illumination intensity of the at least one second light upon the times of its momentary illuminations to be in successive approximations both suprathreshold and subthreshold to the visual field of the patient's eye;

means for sensing the visual detection of non-detection by the patient of the at least one second light upon each of the times of its momentary illumination;

computer means, connected to the means for moving for knowing the position of the moving first source of light and to the control means for knowing the illumination intensity of the at least one second source of light and to the means for sensing for knowing the patient's detection or non-detection, for correlating the recorded detections and non-detections with the distance of separation and angle between the at least one second light and the first source of light at the times of the momentary illuminations at the successively approximated illumination intensities in order to determine a visual sensitivity of the patient's eye at a point upon the island of vision of such patient's eye; and display means, connected to the computer means for receiving the visual sensitivity of the patient's eye, for generating a map of the visual field of the patient's eye, by the same means for moving, otherwise and at other times employed, that is used for moving the illuminated first source of light.

48. A perimeter apparatus for visual field examination comprising:
means for locating a reference stimulus that is fixated by a patient's eye at a succession of points displaced one from the next, the patient's eye moving in order to follow the displacement of the reference stimulus;
means for momentarily displaying a plurality of target stimuli at various angles and distances of separation from the reference stimulus, the momentarily displaying transpiring at certain separate, different, displaced ones of the points at which the reference stimulus is variously located; and
means for receiving from the patient those ones of the plurality of momentarily-displayed target stimuli that are visually detected by the patient's eye at each time, and at each certain reference stimulus location point, that the plurality of target stimuli are displayed; and
means for recording the various angles and distances of separation between detected ones of the plurality of target stimuli and each certain reference stimulus location point as an indication of a visual field of the patient's eye.

49. A method of perimetry comprising:
locating a reference stimulus that is fixated by a patient's eye at a succession of points displaced one from the next so that the patient's eye must move in order to follow the displacement of the reference stimulus;
momentarily displaying a plurality of target stimuli at various angles and distances of separation from the reference stimulus, the momentarily displaying transpiring at certain separate, different, displaced ones of the points at which the reference stimulus is variously located; and receiving from the patient those ones of the plurality of momentarily-displayed target stimuli that are visually detected by the patient's eye at each time, and at each certain reference stimulus location point, that the plurality of target stimuli are displayed; and recording the various angles and distances of separation between detected ones of the plurality of target stimuli and each certain reference stimulus location point as an indication of a visual field of the patient's eye.

50. A modified reverse kinetic perimetry method of examining the visual sensitivity of a patient's eye comprising:

moving an illuminated first light in order that it may be substantially continuously followed by, and substantially continuously visually fixed to the fovea of, a patient's moving eye;

simultaneously illuminating momentarily at times a plurality n of second lights, the plurality of second lights each being at some predetermined distance of separation from, and some angle relative to, the first light at the times of the collective momentary simultaneous illumination;

querying the patient regarding his/her visual detection or non-detection of the numbers zero through n of the plurality of second lights which are visually detected by the patient upon each simultaneous momentary illumination of the plurality n of second lights;

determining if less than the total n of the simultaneous momentary illuminatings of the plurality n of second lights has been detected by the patient and IF all n have been detected THEN continuing with successive simultaneous momentary illuminatings ELSE IF less than n have been detected THEN conducting a binary search by successively momentarily illuminating less than n of the plurality of second lights, each still at the same relative position to the first source of light, until the individual visual detections or non-detections of each of the n second lights are known and recorded.

correlating the detections and non-detections with the corresponding distances of separation and angles between the at least one second light and the first light in order to determine a visual sensitivity of the patient's eye to the illuminations.

51. A method of modified reverse kinetic perimetry by successive approximations to determine a point of visual sensitivity upon an island of vision of a patient's eye, the method comprising:

moving an illuminated first light in order that it may be substantially continuously followed by, and substantially continuously visually fixed to the fovea of, a patient's moving eye;

simultaneously illuminating momentarily at times a plurality n of second lights each being at some predetermined distance of separation from, and same angle relative to, the first light at the times of their collective momentary simultaneous illumination;

varying the illumination intensity of the plurality n of second lights upon the times of their simultaneous momentary illuminations so as to be in successive approximations both suprathreshold and subthreshold to the visual sensitivity of the patient's eye;

querying the patient regarding his/her visual detection or non-detection of the numbers zero through n of the plurality of second lights which are visually detected by the patient upon each simultaneous momentary illumination of the plurality n of second lights;

determining if less than the total n of the simultaneous momentary illuminatings of the plurality n of second lights has been detected by the patient and IF all n have been detected THEN continuing with successive simultaneous momentary illuminatings ELSE IF less than n have been detected THEN conducting a binary search by successively momentarily illuminating less than n of the plurality of second lights, each still at the same relative position to the first source of light, until the individual visual detections or non-detections of each of the n second lights are known; and correlating the detections and non-detections with the distance of separation and angle between the first light and the at least one second light at the times of its momentary illuminations each at a successively approximated illumination intensity in order to determine by the correlating a visual sensitivity at a point upon an island of vision of the patient's eye.

52. An apparatus for examining the visual sensitivity of a patient's eye comprising:

a plurality of individual first light sources at a visual angular separation sufficient to allow a patient's eye having a blind spot at the fovea to fixate upon a geometric center of the plurality of individual first light sources;

means for controllably moving the plurality of individual first light sources collectively so that the patient's eye substantially continually fixes the geometric center of the plurality of first light sources to the fovea even though the patient's eye exhibits a blind spot at this foveal location;

a second source of light assuming various distances of separation from, and angles relative to, the moving first plurality of light sources;

means for querying the patient to indicate periods that he/she does and does not visually detect the second light source while fixedly visually following the moving plurality of first light sources, each change in either sense between periods of detection and periods of non-detection constituting a temporal juncture;

computer means, connected to the means for querying to receive the temporal juncture information and to the means for moving in order to know the position of the moving plurality of first light sources, for calculating the relative positions, in both distances of separation and relative angles, of the geometric center of the plurality of first light sources and of the second sources of light upon at least some of the temporal junctures;

recording means, connected to the computer means to receive the calculated relative positions, for recording the relative positions;

wherein the aggregate recorded relative positions indicate the visual sensitivity of the patient's eye.

53. An apparatus for examining the visual sensitivity of a patient's eye comprising:

a plurality of individual first light sources at a visual angular separation sufficient to allow a patient's eye having a blind spot at the fovea to fixate upon a geometric center of the plurality of individual first light sources;

means for controllably moving the plurality of individual first light sources collectively so that the patient's eye substantially continually fixes the geometric center of the plurality of first light sources to the fovea even though the patient's eye exhibits a blind spot at this foveal location;

a second source of light controllable for illuminating momentarily at times;

means for detecting the visual detection or non-detection by the patient of the second light upon each of the times of its momentary illumination;

computer means connected to the means for controllably moving and to the second source of light and to the means for detecting, for controlling the means for controllably moving so that the position of the plurality of first light sources is known, for controlling the momentary illuminating of the second source of light at times when it is at predetermined distances of separation from, and angles relative to, the moving plurality of first light sources, and for calculating in consideration of the visual detections or non-detections at the times of the momentary illuminatings at the predetermined distances of separation, and angles, of the second source of light relative to the geometric center of the plurality of first light sources, the visual sensitivity of the patient's eye; and recording means, connected to the computer for receiving the calculated visual sensitivity, for recording the calculated visual sensitivity.

54. An apparatus for examining the visual sensitivity of a patient's eye comprising:
a first source of light;
means for moving the first light in order that it may be substantially continuously followed by, and substantially continuously visually fixed to the fovea of, the patient's moving eye;
a second source of light assuming various distances of separation from, and angles relative to, the moving first source of light;
means for calibrating the light output of the second source of light;
means for querying the patient to indicate periods that he/she does and does not visually detect the second light source while fixedly visually following the first light source, each change in either sense between periods of detection and periods of non-detection constituting a temporal juncture;
computer means, connected to the means for querying to receive the temporal juncture information and to the means for moving in order to know the position of the first light source, for calculating the relative positions, in both distances of separation and relative angles, of the first and of the second sources of light upon at least some of the temporal junctures; and
recording means, connected to the computer means to receive the calculated relative positions, for recording the relative positions;
wherein the aggregate recorded relative positions indicate the visual sensitivity of the patient's eye.

55. An apparatus for examining the visual sensitivity of a patient's eye comprising:
a first source of light;
means for controllably moving the first source of light in order that it may be substantially continuously followed by, and substantially continuously visually fixed to the fovea of, the patient's moving eye;
a second source of light controllable for illuminating momentarily at times;
means for calibrating the light output of the second source of light;
means for detecting the visual detection or non-detection by the patient of the second light upon each of the times of its momentary illumination;
computer means, connected to the means for controllably moving and to the second source of light and to the means for detecting,
for controlling the means for controllably moving so that the position of the first source of light is known,
for controlling the momentary illuminating of the second source of light at times when it is at predetermined distances of separation from, and angles relative to, the moving first source of light, and
for calculating in consideration of the visual detections or non-detections at the times of the momentary illuminatings at the predetermined distances of separation, and angles, of the second source of light relative to the first source of light the visual sensitivity of the patient's eye;
recording means, connected to the computer for receiving the calculated visual sensitivity, for recording the calculated visual sensitivity.

56. A modified reverse kinetic perimetry method of examining the visual sensitivity of a patient's eye comprising:
arranging a plurality of individual light sources at a visual angular separation sufficient to allow a patient's eye having a blind spot at the fovea to fixate upon a geometric center of the plurality of individual light sources;
moving the collective plurality of individual light sources in order that it may be substantially continuously followed by, and substantially continuously visually fixed to the fovea of, a patient's moving eye;
wherein the patient's eye substantially continually fixes the geometric center of the plurality of individual light sources to the fovea even though the patient'eye exhibits a blind spot at this foveal location;
illuminating momentarily at times at least one second light, the at least one second light being at predetermined distances of separation from, and angles relative to, the first light at the times of its momentary illuminations;
querying the patient regarding his/her visual detection or non-detection of the at least one second light upon each of the times of its momentary illumination;
correlating the detections and non-detections with the corresponding distances of separation and angles between the at least one second light and the first light in order to determine a visual sensitivity of the patient's eye to the illuminations.

57. A method of modified reverse kinetic perimetry by successive approximations to determine a point of visual sensitivity upon an island of vision of a patient's eye, the method comprising:
arranging a plurality of individual light sources at a visual angular separation sufficient to allow a patient's eye having a blind spot at the fovea to fixate upon a geometric center of the plurality of individual light sources;

moving the collective plurality of individual light sources in order that it may be substantially continuously followed by, and substantially continuously visually fixed to the fovea of, a patient's moving eye;

wherein the patient's eye substantially continually fixes the geometric center of the plurality of individual light sources to the fovea even though the patient's eye exhibits a blind spot at this foveal location;

illuminating momentarily at times at least one second light, the at least one second light being at a predetermined distance of separation from, and angle relative to, the first light at the times of its momentary illuminations;

varying the illumination intensity of the at least one second light upon the times of its momentary illuminations to be in successive approximations both suprathreshold and subthreshold to the visual sensitivity of the patient's eye;

querying the patient regarding his/her visual detection or non-detection of the at least one second light upon each of the times of its momentary illumination;

correlating the detections and non-detections with the distance of separation and angle between the first light and the at least one second light at the times of its momentary illuminations each at a successively approximated illumination intensity in order to determine by the correlating a visual sensitivity at a point upon an island of vision of the patient's eye.

58. A modified reverse kinetic perimetry method of examining the visual sensitivity of a patient's eye comprising:

establishing a matrix of a multiplicity of positionally fixed lights;

moving an illuminated first light by stepwise by successively illuminating the multiplicity of lights, the moving of the illuminated first light being so that it may be substantially continuously followed by, and substantially continuously visually fixed to the fovea of, a patient's moving eye;

illuminating momentarily at times at least one second light, the at least one second light being at predetermined distances of separation from, and angles relative to, the first light at the times of its momentary illuminations;

querying the patient regarding her/her visual detection or non-detection of the at least one second light upon each of the times of its momentary illumination;

correlating the detections and non-detections with the corresponding distances of separation and angles between the at least one second light and the first light in order to determine a visual sensitivity of the patient's eye to the illuminations.

59. A method of modified reverse kinetic perimetry by successive approximations to determine a point of visual sensitivity upon an island of vision of a patient's eye, the method comprising:

establishing a matrix of a multiplicity of positionally fixed lights;

moving an illuminated first light by stepwise by successively illuminating the multiplicity of lights, the moving of the illuminated first light being so that it may be substantially continuously followed by, and substantially continuously visually fixed to the fovea of, a patient's moving eye;

illuminating momentarily at times at least one second light, the at least one second light being at a predetermined distance of separation from, and angle relative to, the first light at the times of its momentary illuminations;

varying the illumination intensity of the at least one second light upon the times of its momentary illuminations to be in successive approximations both suprathreshold and subthreshold to the visual sensitivity of the patient's eye;

querying the patient regarding his/her visual detection or non-detection of the at least one second light upon each of the times of its momentary illumination;

correlating the detections and non-detections with the distance of separation and angle between the first light and the at least one second light at the times of its momentary illuminations each at a successively approximated illumination intensity in order to determine by the correlating a visual sensitivity at a point upon an island of vision of the patient's eye.

60. A modified reverse kinetic perimetry method of examining the visual sensitivity of a patient's eye comprising:

moving an illuminated first light in order that it may be substantially continuously followed by, and substantially continuously visually fixed to the fovea of, a patient's moving eye;

illuminating momentarily at times a plurality n of second lights, each second light being at a predetermined distance of separation from, and angle relative to, the first light at the times of its momentary illuminations;

querying the patient regarding her/her visual detection or non-detection of the number 0 through n of the plurality of second lights upon each of the times of their momentary illumination;

correlating the detections and non-detections with the corresponding distances of separation and angles between each of the plurality of second lights and the first light in order to determine a visual sensitivity of the patient's eye to the illuminations.

61. A method of modified reverse kinetic perimetry by successive approximations to determine a point of visual sensitivity upon an island of vision of a patient's eye, the method comprising:

moving an illuminated first light in order that it may be substantially continuously followed by, and substantially continuously visually fixed to the fovea of, a patient's moving eye;

illuminating momentarily at times a plurality n of second lights, each second light being at a predetermined distance of separation from, and angle relative to, the first light at the times of its momentary illuminations;

varying the illumination intensity of the plurality of second lights upon the times of their momentary illuminations to be in successive approximations both suprathreshold and subthreshold to the visual sensitivity of the patient's eye;

querying the patient regarding his/her visual detection or non-detection of the number 0 through n of the plurality of second lights upon each of the times of their momentary illuminations;

correlating the detections and non-detections with the corresponding distances of separation and angle between the first light and the plurality of second lights at the times of their momentary illuminations, each at a successively approximated illumination intensity, in order to determine by the correlating a visual sensitivity at a point upon an island of vision of the patient's eye.

* * * * *